US007527962B2

(12) United States Patent
Gimeno et al.

(10) Patent No.: US 7,527,962 B2
(45) Date of Patent: May 5, 2009

(54) HUMAN DIACYLGLYCEROL ACYLTRANSFERASE 2 (DGAT2) FAMILY MEMBERS AND USES THEREFOR

(75) Inventors: Ruth E. Gimeno, Wellesley, MA (US); Zhidan Wu, Boston, MA (US); Rosana Kapeller-Libermann, Chestnut Hill, MA (US); Brian K. Hubbard, Beverly, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 35 days.

(21) Appl. No.: 11/296,615

(22) Filed: Dec. 7, 2005

(65) Prior Publication Data

US 2006/0183210 A1    Aug. 17, 2006

Related U.S. Application Data

(62) Division of application No. 10/324,618, filed on Dec. 19, 2002, now abandoned.

(60) Provisional application No. 60/411,859, filed on Sep. 19, 2002, provisional application No. 60/341,947, filed on Dec. 19, 2001.

(51) Int. Cl.
*C12N 9/10* (2006.01)
*C12N 1/20* (2006.01)
*C12P 15/70* (2006.01)
*C07H 21/04* (2006.01)

(52) U.S. Cl. ............... 435/252.3; 435/193; 435/320.1; 536/23.2

(58) Field of Classification Search ............... 435/193, 435/6, 15, 69.1, 134, 320.1, 252.3, 257.2; 536/23.2
See application file for complete search history.

(56) References Cited

U.S. PATENT DOCUMENTS

| | | | |
|---|---|---|---|
| 4,522,811 A | 6/1985 | Eppstein et al. | |
| 4,676,980 A | 6/1987 | Segal et al. | |
| 4,683,202 A | 7/1987 | Mullis | |
| 4,868,103 A | 9/1989 | Stavrianopoulos et al. | |
| 4,873,316 A | 10/1989 | Meade et al. | |
| 4,987,071 A | 1/1991 | Cech et al. | |
| 5,093,246 A | 3/1992 | Cech et al. | |
| 5,116,742 A | 5/1992 | Cech et al. | |
| 5,272,057 A | 12/1993 | Smulson et al. | |
| 5,272,071 A | 12/1993 | Chappel | |
| 5,283,317 A | 2/1994 | Saifer et al. | |
| 5,328,470 A | 7/1994 | Nabel et al. | |
| 5,459,039 A | 10/1995 | Modrich et al. | |
| 5,498,531 A | 3/1996 | Jarrell | |
| 5,545,806 A | 8/1996 | Lonberg et al. | |
| 5,569,825 A | 10/1996 | Lonberg et al. | |
| 5,625,126 A | 4/1997 | Lonberg et al. | |
| 5,631,169 A | 5/1997 | Lakowicz et al. | |
| 5,633,425 A | 5/1997 | Lonberg et al. | |
| 5,661,016 A | 8/1997 | Lonberg et al. | |
| 5,854,033 A | 12/1998 | Lizardi | |
| 5,866,336 A | 2/1999 | Nazarenko et al. | |
| 5,876,930 A | 3/1999 | Livak et al. | |
| 6,033,862 A | 3/2000 | Matsuda et al. | |
| 6,344,548 B1 * | 2/2002 | Farese et al. ............... | 536/23.2 |
| 2002/0119138 A1 | 8/2002 | Cases et al. | |
| 2003/0152574 A1 * | 8/2003 | Logan et al. ............. | 424/146.1 |
| 2003/0161831 A1 * | 8/2003 | Cases et al. ............. | 424/146.1 |
| 2006/0127892 A1 | 6/2006 | Busjahn et al. | |

FOREIGN PATENT DOCUMENTS

| | | |
|---|---|---|
| EP | 0 264 166 | 8/1996 |
| WO | 88/09810 | 12/1988 |
| WO | 89/10134 | 11/1989 |
| WO | 91/06667 | 5/1991 |
| WO | 94/10300 | 5/1994 |
| WO | 0005367 * | 2/2000 |
| WO | WO 01/90329 A2 | 11/2001 |
| WO | WO 02/068595 A2 | 9/2002 |

OTHER PUBLICATIONS

Wakimoto et al. GenBank Acession No. BAB40641 (created April 3, 2001).*
Cases et al. "Cloning of DGAT2, a second mammalian diacylglycerol acyltransferase, and related family members", J. Biol. Chem. 276: 38870-38876, Oct. 2001.*
Cases et al. GenBank Acession No. AAK84176 (created Aug. 8, 2001).*
Cheng et al. "Human acyl-CoA:diacylglycerol acyltransferase is a tetrameric protein", Biochem. J. 359: 707-714, Nov. 2001.*
Watanabe, K., et al., "Hypothetical Protein FLJ22644," Mar. 1, 2001, (sequence), EMBL Database [online], Hinxton, Cambridge, U.K., European Bioinformatics Institute, EMBL Accession No. Q9H630.
Kato, S., et al., "Human Protein Clone HP02485," June 12, 2000, (sequence) GenBank [online] Bethesda, MD, USA: National Center for Biotechnology, GenBank Accession No. AAY94889.
Baker, K.P., et al., "Human PRO Polypeptide Sequence #168," Dec. 18, 2001, (sequence) GenBank [online] Bethesda, MD, USA: National Center for Biotechnology Information, GenBank Accession No. AAU29191.

(Continued)

Primary Examiner—Nashaat T Nashed
Assistant Examiner—Iqbal H Chowdhury

(57) ABSTRACT

The present invention relates to compositions and methods for the diagnosis and treatment of obesity and related metabolic disorders. The invention provides isolated nucleic acids molecules, designated DGAT2 family member nucleic acid molecules, which encode diacylglycerol acyltransferase family members. The invention also provides recombinant expression vectors containing DGAT2 family member nucleic acid molecules, host cells into which the expression vectors have been introduced, and nonhuman transgenic animals in which a DGAT2 family member gene has been introduced or disrupted. The invention still further provides isolated DGAT2 family member proteins, fusion proteins, antigenic peptides and anti-DGAT2 family member antibodies. Methods of use of the provided DGAT2 family member compositions for screening, diagnostic and therapeutic methods in connection with obesity disorders are also disclosed.

15 Claims, No Drawings

OTHER PUBLICATIONS

Nishina, P. M. et al., Metab. 43:554-558 (1994).
Grundy, S. M. & Barnett, J. P., Dis. Mon. 36:641-731 (1990).
Friedman, J. M. et al., Mammalian Gene 1:130-144 (1991).
Stunkard, N. Eng. J. Med. 322:1483-1487 (1990).
Moll et al., Am. J. Hum. Gen. 49:1243-1255 (1991).
Kahn, Nature Genetics 25:6-7 (2000).
Palou et al., Eur. J. Nutr. 39:127-144 (2000).
Smith, Nature Genetics 25:87 (2000).
Lodish et al. (1995) Molecular Cell Biology (Scientific American Books Inc., New York, N.Y.).
Stryer, (1988) Biochemistry, (W. H. Freeman, New York, N.Y.).
Sonnhammer et al., Protein 28:405-420 (1997).
Zagotta W. N. et al., Annual Rev. Neuronsci. 19:235-263 (1996).
Lardizabal, K. K. et al., J. Biol. Chem. 276:38862-38869 (2001).
Cases, S. et al., J. Biol. Chem. 276:38870-38876 (2001).
Hlongwane, C. et al., Rapid Commun. Mass Spectrom. 15:2027-2034 (2001).
Ayorinde, F. O. et al., Rapid Commun. Mass Spectrom. 13:1762-1769 (1999).
Byrdwell, W. C. et al., R. O. Lipids. 31:919-935 (1996).
Bierbach, H., Digestion 28:138-147 (1983).
Storey, B. T. et al., Mol. Reprod. Dev. 49:400-407 (1998).
Wright, S. K. et al., Anal. Biochem. 265:8-14 (1998).
Stryer L. et al., Proc. Natl Acad Sci USA 58:719-726 (1967).
Selvin P. R., Methods Enzymol 246:300-334 (1995).
Trotter, Pamela J. et al., Journal of Lipid Research 32:293-304 (1991).
Bhaumik, Mantu, et al., "Cloning and chromosomal mapping of the mouse *Mgat*3 gene encoding *N*-acetylglucosaminyltransferase III," *Gene*, vol. 164, No. 2 (1995) pp. 295-300.
Cases, Sylvaine, et al., "Identification of a gene encoding an acyl CoA:diacylglycerol acyltransferase, a key enzyme in triacylglycerol synthesis," *Proceedings of the National Academy of Science USA*, vol. 95 (Oct. 1998) pp. 13018-13023.
Altschul, S.F., et al., "Basic Local Alignment Search Tool", *J. Mol. Biol.*, 215:403-410 (1990).
Altschul, S.F., et al., "Gapped BLAST and PSI-BLAST: a new generation of protein database search programs", *Nucleic Acids Research*, 25(17):3389-3402 (1997).
Ansell, R.J.,et al., "Molecularly imprinted polymers for bioanalysis: chromatography, binding assays and iomimeic sensors", *Curr. Opin. In Biotech.*, 7:89-94 (1996).
Arkin, A.P. & Youvan, D.C., "An algorithm for protein engineering: Simulations of recursive ensemble mutagenesis", *Proc. Natl. Acad. Sci. USA*, 89(16):7811-7815 (1992).
Ayorinde, F.O., et al., "Matrix-assisted Laser Desorption/Ionization Time-of-flight Mass Spectrometry of Cod Liver Oil and the Effect of Analyte/Matrix Concentration on Signal Intensities", *Rapid Comm. In Mass Spectrometry*, 13:1762-1769 (1999).
Banerji, J., et al., "A Lymphocyte-Specific Cellular Enhancer Is Located Downstream of the Joining Region in Immunoglobulin Heavy Chain Genes", *Cell*, 33:729-740 (1983).
Barany, F., "Genetic disease detection and DNA amplification using cloned thermostable ligase", *Proc. Natl. Acad. Sci. USA*, 88(1):189-193 (1991).
Bartel, P., et al., "Elimination of False Positives That Arise in Using the Two-Hybrid System", *BioTechniques*, 14(6):920-024 (1993).
Bartel, D.P. & Szostak, J.W., "Isolation of New Robozymes from a Large Pool of Random Sequences", *Science*, 261:1411-1418 (1993).
Berg, J.M., et al.,*Biochemistry*, 5th Ed.:Table of Contents.
Bhattacharya-Chatterjee, M. & Foon, K.A., "Anti-idiotype antibody vaccine therapies of cancer", *Cancer Treat Res*.94:51-68 (1998).
Bierbach, H., "Traicylglycerol Biosynthesis in Human Small Intestinal Mucosa. Acyl-CoA:Monoglyceride Acyltransferase", *Digestion*, 28:138-147 (1983).
Börjeson, M., "The Aetiology of Obesity in Children", *Acta Paediatr. Scand.*, 65:279-287 (1976).
Byrdwell, W.C., et al., "Quantitative Analysis of Triglycerides Using Atmospheric Pressure Chemical Ionization-Mass Spectrometry", *Lipids*, 31:919-935 (1996).

Byrne, G.W. & Ruddle, F.H., "Multiplex gene regulation: A two-tiered approach to transgene regulation in transgenic mice", *Proc. Natl. Acad. Sci. USA*, 86(14):5473-5477 (1989).
Calame, K. & Eaton, S., "Transcriptional Controlling Elements in the Immunoglobulin and T Cell Receptor Loci", *Adv. Immunol.*, 43:235-275 (1988).
Camper, S.A. & Tilghman, S.M., "Postnatal repression of the α-fetoprotein gene is enhancer independent", *Genes & Devel.*, 3:537-546 (1989).
Carell, T., et al., "A Novel Procedure for the Synthesis of Libraries Containing Small Organic Molecules",*Angew. Chem. Int. Ed. Engl.*, 33(20):2059-2061 (1994).
Carell, T., et al. "A Solution-Phase Screening Procedure for the Isolation of Active Compounds from a Libarry of Molecules", *Angew. Chem. Int. Ed. Engl*, 33(20):2061-2064 (1994).
Cases, S., et al., "Cloning of DGAT2, a Second Mammalian Diacylglycerol Acyltransferase, and Related Family Members", *J. of Biol. Chem.*, 276(42):38870-38876 (2001).
Chen, S.-H., et al., "Gene therapy for brain tumors: Regression of experimental gliomas by adenovirus-mediated gene transfer in vivo", *Proc. Nat. Acad. Sci. USA*, 91(8):3054-3057 (1994).
Colcher, D., et al., "Single-Chain Antibodies in Pancreatic Cancer", *Ann. N.Y. Acad. Sci.*, 30*880):263-280 (1999).
Cotton, R.G.H., et al., "Reactivity of cytosine and thymine in single-base-pair mismatches with hydroxylamine and osmium tetroxide and its application to the study of mutations", *Proc. Natl. Acad. Sci. USA*, 85(12):4397-4401 (1988).
Cotton, R.G.H., "Current methods of mutation detection", *Mut. Res.*, 285(1):125-144 (1993).
Cronin, M.T., "Cystic Fibrosis Mutation Detection by Hybridization to Light-Generated DNA Probe Arrays", *Human Mut.*, 7:244-255 (1996).
Cruiksbank, W.W., et al., "A Lipidated Anti-Tat Antibody Enters Living Cells and Blocks HIV-1 Viral Replication", *J. of Acq. Imm. Def. Syndromes & Hum. Retrovirology*, 14:193-203 (1997).
Cull, M.G., et al., "Screening for receptor ligands using large libraries of peptides linked to the C terminus of the *lac* repressor", *Proc. Nat. Acad. Sci. USA*, 89(5):1865-1869 (1992).
Cwirla, S.E., et al., "Peptides on phage: A vast library of peptides for identifying ligands", *Proc. Natl. Acad. Sci. USA*, 87(16):6378-6382 (1990).
D'Eustachio, P. & Ruddle, F.H., "Somatic Cell Genetics and Gene Families", *Science*, 220:919-924 (1983).
Delagrave, S., et al., "Recursive ensemble mutagenesis", *Protein Engin.*, 6(3):327-331 (1993).
Devlin, J.J., et al., "Random Peptide Libraries: A Source of Specific Protein Binding Molecules", *Science*, 249:404-406 (1990).
DeWitt, S.H., et al., ""Diversomers": An Approach to nonpeptide, nonoligomeric chemical diversity", *Proc. Natl. Acad. Sci. USA*. 99(15):6909-6913 (1993).
Edlund, T., et al., "Cell-Specific Expression of the Rat Insulin Gene: Evidence for Role of Two Distinct 5' Flanking Elements", *Science*, 230:912-916 (1985).
Egeland, J.A., et al., "Bipolar affective disorders linked to DNA markers on chromosome 11", *Nature*, 325:783-787 (1987).
Eichelbaum, M. & Evert, B., "Influence of Pharmacogenetics on Drug Dispositoin and Response", *Clin. & Exp. Pharmacology & Physiol.*, 23:983-985 (1996).
Erb, E., et al., "Recursive deconvolution of combinatorial chemicval libraries", *Proc. Natl. Acad. Sci. USA*, 91(24):11422-11426 (1994).
Fan, Y.-S., et al., "Mapping small DNA sequences by fluorescence in situ hybridization directly on banded metaphase chromosomes", *Proc. Natl. Acad. Sci. USA*, 87(16):6223-6227 (1990).
Felici, F., "Selection of Antibody Ligands from a Large Library of Oligopeptides Expressed on a Multivalent Expositoin Vector", *J. Mol. Biol.*, 222:301-310 (1991).
Fodor, S.P.A., et al., "Multiplexed biochemical assays with biological chips", *Nature*, 364:555-556 (1993).
Friedman, J.M., et al., "Molecular mapping of obesity genes", *Mamm. Genome.*, 1:130-144 (1991).
Gallop, M.A., et al., "Applications of Combinatorial Technologies to Drug Discovery. 1. Background and Peptide Combinatorial Libraries", *J. of Medic. Chem.*, 37(9):1233-1251 (1994).

Gasparini, P., et al., "Restriction site generating-polymerase chain reaction (RG-PCR) for the probeless detection of hidden genetic variation: application to the study of some common cystic fibrosis mutations", *Mol. And Cell. Probes*. 6:1-7 (1992).

Gautier, C., et al., "α-DNA IV: α-anormeric and β-anomeric tetrathymidylates covalently linked to intercalating oxazolopyridocarbazole. Synthesis, physicochemical properties and poly (rA) binding", *Nucl. Acids Res.*, 15(16):6625-6641 (1987).

Gibbs, R.A., et al., "Detection of single DNA base differences by competitive oligonucleotide priming", *Nucl. Acids Res.*, 17(7):2437-2448 (1989).

Goeddel, D.V., "Systems for Heterologous Gene Expression", *Meth. In Enzymology*, 185:3-7 (1990).

Gottesman, S., "Minimizing Proteolysis in *Escherichia coli*: Genetic Solutions", *Meth. In Enzymology*, 185:119-129 (1990).

Grundy, S.M. & Barnett, J.P., "Metabolic and Health Complications of Obesity", *Dis. Mon.*, 36:641-731 (1990).

Guatelli, J.C., "Isothermal, in vitro amplification of nucleic acids by a multienzyme reaction modeled after retroviral replication", *Proc. Natl. Acad. Sci. USA*, 87(5):1874-1878 (1990).

Hage, D.S. & Tweed, S.A., "Recent advances in chromatographic and electrophoretic methods for the study of drug-protein interactins", *J. of Chromatography B*, 699:499-525 (1997).

Harlow, E. & Lane, D., *Antibodies: A Laboratory Manual*, Table of Contents (1988).

Haseloff, J. & Gerlach, W.L., "Simple RNA Enzymes with new and highly specific endoribonuclease activities", *Nature*, 334:585-591 (1988).

Hayashi, K., "PCR-SSCP: A Method for Detection of Mutations", *GATA*, 9*3):73-79 (1992).

Hattis, D., "Use of Biological Markers and Pharmacokinetics in Human Health Risk Assessment", *Env. Health Persp.*, 90:229-238 (1991).

Heegaard, N.H.H., "Capillary electrophoresis for the study of affinity interactions", *J. of Molec. Recog.*, 11:141-148 (1998).

Hélène, C., "The anti-gene strategy: control of gene expression by triplex-forming-oligonucleotides", *Anti-Cancer Drug Des.*, 6:569-584 (1991).

Helene, C., et al., "Control of Gene Expression by Triple Helix-Foring Oligonucleotides", *Ann. N.Y. Acad. Of Sci.*, 660:27-38 (1992).

Herlyn, D. & Birebent, B., "Advances in cancer vaccine development", *Ann. Med.*, 31:66-78 (1999).

Hlongwane, C., et al., "Comparative quantitative fatty acid analysis of triacylglycerols using matrix-assisted laser desorption/ionization time-of-flight mass spectrometry and gas chromatography", *Rapid Comm. In Mass Spectrometry*. 15:2027-2034 (2001).

Houghten, R.A., et al., "The Use of Synthetic Peptide Combinatorial Libraries for the Identification of Bioactive Peptides", *BioTechniques*, 13(3):412-421 (1992).

Hsu, I.-C., et al., "Detection of DNA point mutations with DNA mismatch repair enzymes", *Carcinogenesis*, 15(8):1657-1662 (1994).

Hyrup, B. & Nielsen, P.E., "Peptide Nucleic Acids (PNA): Synthesis, Properties and Potential Applications", *Bioorg. & Medic. Chem.*, 4(1):5-23 (1996).

Inoue, H., et al., "Sequence-dependent hydrolysis of RNA using modified oligonucleotide splints and R Nase H", *FEB*, 215(2):327-330 (1987).

Inoue, H., et al., "Synthesis and hybridization studies on two complementary nona(2'-O-methyl)ribocucleotides", *Nucl. Acids Res.*, 15(15):6131-6148 (1987).

Iwabuchi, K., et al., "Use of the two-hybrid system to identify the domain of p53 involved in oligomerization", *Oncogene*, 8:1693-1696 (1993).

James, J.S., ""Surrogate Markers": Current Status, Future Directions (Part 1)", *Aids Treatment News Arch.*, 209:1-8 (1994).

Jespers, L.S., et al., "Guiding the Selection of Human Antibodies from Phage Display Repertoires to a Single Epitope of an Antigen", *Bio/Technology*, 12:899-903 (1994).

Kahn, C. R., "Triglycerides and toggling the tummy", *Nature Genetics*, 25:6-7 (2000).

Keen, J., et al, "Rapid detection of single base mismatches as heteroduplexes on Hydrolink gels", *Trends Genet.*, 7(1):5 (1991).

Kessel, M. & Gruss, P., "Murine Developmental Control Genes", *Science*, 249:347-379 (1990).

Koomen, J.M. et al., "Mapping of surrogate markers of cellular components and structures using laser desorption/ionization mass spectrometry", *J. of Mass Spectrometry*, 35:258-264 (2000).

Kozal, M.J., et al., "Extensive polymorphisms observed in HIV-1 clade B protease gene using high-density oligonucleotide arrays", *Nature Medicine*, 2(7):753-759 (1996).

Kriz, D., et al., "Introducing Biomimetic Sensors Based on Molecularly Imprinted Polymers as Recognition Elements", *Anal. Chem.*, 67:2142-2144 (1995).

Kwoh, D.Y., et al., "Transcription-based amplification system and detection of amplified human immunodeficiency virus type I with a bead-based sandwixh hybridization format", *Proc. Natl. Acad. Sci. USA*, 86(4):1173-1177 (1989).

Lam, K.S., et al., "A new type of synthetic peptide library for identifying ligand-binding activity", *Nature*, 354:82-84 (1991).

Lam, K.S., "Application of combinatorial library methods in cancer research and drug discovery",*Anti-Cancer Drug Design*, 12:145-167 (1997).

Langmuir, M.E., et al., "New Thiol Active Fluorophores for Intracellular Thiols and Glutathione Measurement," *Fluorescence Microscopy & Fluorescent Probes*, 229-233 (1996).

Lardizabal, K.D., et al., "DGAT2 Is a New Diacylglycerol Acyltransferase Gene Family", *J. of Biol. Chem.*, 276(42):38862-38869 (2001).

Lemaitre, M., et al., "Specific antiviral activity of a poly9L-lysine)-conjugated oligodeoxyribonucleotide sequence complementary to vesicular stomatitis virus N protein mRNA initiation site", *Proc. Natl. Acad. Sci. USA*, 84(3):648-652 (1987).

Letsinger, R.L., et al., "Cholesteryl-conjugated oligonucleotides: Synthesis, properties, and activity as inhibitors of replication of human immunodeficiency virus in cell culture", *Proc. Natl. Acad. Sci. USA*, 86(17):6553-6556 (1989).

Linder, M.W., et al., "Pharmacogenetics: a laboratory tool for optimizing therapeutic efficiency", *Clin. Chem.*, 43(2):254-266 (1997).

Lizardi, P.M., et al., Exponential Amplification of Recombinant-RNA Hybridization Probes, *Bio/Technology*, 6:1197-1202 (1988).

Lodish, H., et al., *Molecular Cell Biology*, 3rd Ed.:Table of Contents (1995).

Lonberg, N. & Huszar D., "Human Antibodies from Transgenic Mice", *Intern. Rev. Immunol.*, 13:65-93 (1995).

Madura, K., et al., "N-recognin/UBC2 Interactions in the N-end Rule Pathway", *J. of Biol. Chem.*, 268(16):12046-12054 (1993).

Maher, III, L.J., "DNA Triple-Helix Formation: An Approach to Artificial Gene Repressors?", *BioEssays*, 14(12):807-815 (1992).

Marasco, W.A., et al., "Design, intracellular expression, and activity of a human anti-human immunodeficiency virus type 1 gp120 single-chain antibody", *Proc. Natl. Acad. Sci. USA*, 90(16):7889-7893 (1993).

McLeod, H.L., "Selection of Markers to Predict Tumour Response Or Survival: Description of a Novel Approach", *Eur. J. of Cancer*, 35(12):1650-1652 (1999).

Myers, E.W. & Miller, W., "Optimal alignments in linear space", *CABIOS*, 4(1):11-17 (1988).

Myers, R.M., et al., "Detection of single base substitutions in total genomic DNA", *Nature*, 313:495-498 (1985).

Myers, R.M., et al., "Detectoin of Single Base Substitutions by Ribonuclease Cleavage at Mismatches in RNA:DNA Duplexes", *Science*, 230:1242-1246 (1985).

Naeve, C.W., "Accuracy of Automated DNA Sequencing: A Multi-Laboratory Comparison of Sequencing Results", *BioTechniques*, 19(3):448-453 (1995).

Needleman, S.B. & Wunsch, C.D., "A General Method Applicable to the Search for Siilarities in the Amino Acid Sequence of Two Proteins", *J. Mol. Biol.*, 48:443-453 (1970).

Nicolau, D.P., "Using pharmacodynamic and pharmacokinetic surrogate markers in clinical practice: Optimizing antimicrobial therapy in respiratory-tract infections", *Am. J. Health-Syst. Pharm.*, 56(15)-Suppl. 3:S16-S20 (1999).

Nishina, P.M., et al., Atherosciersosis in Genetically Obese Mice: The Mutants Obese, Diabetes, Fat, Tubby, and Lethal Yellow, *Metabolism*, 43(5):554-558 (1994).

Orita, M., et al., "Detection of polymorphisms of human DNA by gel electrophoresis as single-strand conformation polymorphisms", *Proc. Natl. Acad. Sci. USA*, 86(8):2766-2770 (1989).

Osborne, S.E., et al., "Aptamers as therapeutic and diagnostic reagents: problems and prospects", *Curr. Opin. In Chem. Biol.*, 1:5-9 (1997).

Palou, A., et al., "Obesity: molecular bases of a multifactorial problem", *Eur. J. Nutr.*, 39:127-144 (2000).

Patel, D.J., "Structural analysis of nucleic acid aptamers", *Curr. Opin. In Chem. Biol.*, 1:32-46 (1997).

Perry-O'Keefe, H., et al., "Peptide nucleic acid pre-gel hybridization: An alternative to Southern hybridization", *Proc. Natl. Acad. Sci. USA*, 93(25):14670-14675 (1996).

Pinkert, C.A., et al., "An albumin enhancer located 10 kb upstream functions along with its promoter to direct efficient, liver-specific expression in transgenic mice", *Genes & Devel.*, 1:268-276 (1987).

Prosser, J., "Detecting single-base mutations", *Tibech*, 11:238-246 (1993).

Queen, C. & Baltimore, D., "Immunoglobulin Gene Transcription Is Activated by Downstream Sequence Elements", *Cell*. 33:741-748 (1983).

Reiter Y & Pastan, I., "Antibody Engineering of Recombinant Fv Immunotoxins for Improved Targeting of Cancer: Disulfide-stabilized Fv Immunotoxins", *Clin. Canc. Res.*, 2(2):245-252 (1996).

Rivas, G. & Minton, A.P., "New developments in the study of biomolecular associations via sedimentation equilibrium", *Trends Biochem. Sci.*, 18(8):284-287 (1993).

Rosenbaum, V. & Riesner D., "Temperature-gradient gel electrophoresis", *Biophys. Chem.*, 26:235-246 (1987).

Saiki, R.K., et al., "Analysis of enzymatically amplified β-globin and HLA-DQα DNA with allele-specific oligonucleotide probes", *Nature*, 324:163-166 (1986).

Saiki, R.K., et al., Genetic analysis of amplified DNA with immobilized sequence-specific oligonucleotide probes, *Proc. Natl. Acad. Sci. USA*, 86(16):6230-6234 (1989).

Saleeba, J.A., & Cotton, R.G.H., "Chemical Cleavage of Mismatch to Detect Mutations", *Meth. In Enzymology*, 217:286-295 (1993).

Sambrook, J., et al., *Molecular Cloning*, 2$^{nd}$ Ed.:Table of Contents (1989).

Schentag, J.J., "Pharmacokinetic and pharmacodynamic surrogate markers" Studies with fluoroquinolones in patients, *Am. J. Health-Syst. Pharm.*, 56(Suppl. 3):S21-S24 (1999).

Scott, J.K. & Smith G.P., "Searching for Peptide Ligands with an Epitope Library", *Science*, 249:386-390 (1990).

Selvin, P.R., "Fluorescence Resonance Engergy Transfer", *Meth. In Enzymology*, 246:300-334 (1995).

Shea, K.J., "Molecular Imprinting of Synthetic Network Polymers: The De Novo Synthesis of Macromolecular Binding and Catalytic Sites", *Trends in Polymar Sci.*, 2(5):166-173 (1994).

Sjölander, S. & Urbaniczky, C., "Integrated Fluid Handling System for Biomolecular Interaction Analysis", *Anal. Chem.*, 63:2338-2345 (1991).

Smith, D.B. & Johnson, K.S., "Single-step purification of polypeptides expressed in *Escherichia coli* as fusions with glutathione S-transferase", *Gene*, 67:31-40 (1988).

Smith, S.J., "Obesity resistance and multiple mechanisms of triglyceride synthesis in mice lacking Dgat",*Nature Genetics*, 25:87-90 (2000).

Storey, B.T., et al., Human Sperm Glutathione Reductase Activity in Situ Reveals Limitation in the Glutathione Antioxidant Defense System Due to Supply of NADPH, *Mol. Reprod. Dev.*, 49:400-407 (1998).

Strauss, W.M., "Hybridization with Radioactives Probes", *Curr. Prot. In Mol. Biol.*, Suppl. 24:Sec. 11(6.3-6.3.6) (1989).

Stryer, L. & Haugland, R.P., "Energy Transfer: A Spectroscopic Ruler", *Proc.Natl. Acad. Sci. USA*, 58(2):719-726 (1967).

Stunkard, A.J., et al., "The Body-Mass Index of Twins Who Have Been Reared Apart", *N. Eng. J. Med.*, 322(21):1483-1487 (1990).

Szabo, A., et al., "Surface plasmon resonance and its use in biomolecualr interaction analysis (BIA)", *Curr. Opin in Struct. Biol.*, 5:699-705 (1995).

Trotter, P.J. & Storch, J., "Fatty acid uptake and metabolism in a human intestinal cell line (Caco-2): comparison of apical and basolateral incubation", *J. of Lipid Res.*, 32:293-304 (1991).

van der Krol, A.R., et al., "Modulation of Eukaryotic Gene Expression by omplementary RNA or DNA Sequences", *BioTechniques*, 6(10):958-976 (1988).

Verma, R.S. & Babu, A., *Human Chromosomes: Manual of Basic Techniques*, Tabl. of Cont., (1988).

Vlatakis, G., et al., "Drug assay using antibody mimics made by molecular imprinting", *Nature*, 361:645-647 (1993).

Wada, K-n., et al., "Codon usage tabulated from the GenBank genetic sequence data", *Nucl. Acids Res.*, 20(Suppl.):2111-2118 (1992).

Weintraub, H., et al., "Anti-sense RNA as a molecular tool for genetic analysis", *Rev. in Trends in Genetics*, 1(1):22-25 (1985).

Winoto, A. & Baltimore, D., "A novel, inducible and T cell-specific enhancer located at the 3' end of the T cell receptor α locus", *The EMBO J.*, 8(3):729-733 (1989).

*World Review of Nutrition and Dietetics*, 63:Tabl. of Cont. (1989).

Wright, S.K. & Viola, R.E., "Evaluation of Methods for the Quantitation of Cysteines in Proteins", *Analy. Biochem.*, 265:8-14 (1988).

Zervos, A.S., et al., "Mxil, a Protein That Specifically Interacts with Max to Bind Myc-Max Recognition Sites", *Cell*, 72:223-232 (1993).

Zon, G., "Oligonucleotide Analogues as otential Chemotherapeutic Agents", *Pharm. Res.*, 5(9):539-549 (1988).

Zuckermann, R.N., et al., "Discovery of Nanomolar Ligands for 7-Transmembrane G-Protein-Coupled Receptors from a Diverse *N*-(Substituted)glycine Peptoid Library", *J. Med. Chem.*, 37:2678-2685 (1994).

* cited by examiner

SEQUENCE LISTING

```
<160> NUMBER OF SEQ ID NOS: 65

<210> SEQ ID NO 1
<211> LENGTH: 1005
<212> TYPE: DNA
<213> ORGANISM: human
<220> FEATURE:
<221> NAME/KEY: CDS
<222> LOCATION: (1)...(1005)

<400> SEQUENCE: 1 atg gta gag ttc gcg ccc ttg ttt atg ccg tgg gag cgc agg ctg cag      48
Met Val Glu Phe Ala Pro Leu Phe Met Pro Trp Glu Arg Arg Leu Gln
 1               5                  10                  15
```

-continued

```
aca ctt gct gtc cta cag ttt gtc ttc tcc ttc ttg gca ctg gcc gag      96
Thr Leu Ala Val Leu Gln Phe Val Phe Ser Phe Leu Ala Leu Ala Glu
         20                  25                  30 atc tgc act gtg ggc ttc ata gcc ctc ctg ttt aca aga ttc tgg ctc     144
Ile Cys Thr Val Gly Phe Ile Ala Leu Leu Phe Thr Arg Phe Trp Leu
 35                  40                  45 ctc act gtc ctg tat gcg gcc tgg tgg tat ctg gac cga gac aag cca     192
Leu Thr Val Leu Tyr Ala Ala Trp Trp Tyr Leu Asp Arg Asp Lys Pro
         50                  55                  60 cgg cag ggg ggc cgg cac atc cag gcc atc agg tgc tgg act ata tgg     240
Arg Gln Gly Gly Arg His Ile Gln Ala Ile Arg Cys Trp Thr Ile Trp
 65                  70                  75                  80 aag tac atg aag gac tat ttc ccc atc tcg ctg gtc aag act gct gag     288
Lys Tyr Met Lys Asp Tyr Phe Pro Ile Ser Leu Val Lys Thr Ala Glu
                 85                  90                  95 ctg gac ccc tct cgg aac tac att gcg ggc ttc cac ccc cat gga gtc     336
Leu Asp Pro Ser Arg Asn Tyr Ile Ala Gly Phe His Pro His Gly Val
        100                 105                 110 ctg gca gtc gga gcc ttt gcc aac ctg tgc act gag agc aca ggc ttc     384
Leu Ala Val Gly Ala Phe Ala Asn Leu Cys Thr Glu Ser Thr Gly Phe
        115                 120                 125 tct tcg atc ttc ccc ggt atc cgc ccc cat ctg atg atg ctg acc ttg     432
Ser Ser Ile Phe Pro Gly Ile Arg Pro His Leu Met Met Leu Thr Leu
130                 135                 140 tgg ttc cgg gcc ccc ttc ttc aga gat tac atc atg tct gca ggg ttg     480
Trp Phe Arg Ala Pro Phe Phe Arg Asp Tyr Ile Met Ser Ala Gly Leu
145                 150                 155                 160 gtc aca tca gaa aag gag agt gct gct cac att ctg aac agg aag ggt     528
Val Thr Ser Glu Lys Glu Ser Ala Ala His Ile Leu Asn Arg Lys Gly
                165                 170                 175 ggc gga aac ttg ctg ggc atc att gta ggg ggt gcc cag gag gcc ctg     576
Gly Gly Asn Leu Leu Gly Ile Ile Val Gly Gly Ala Gln Glu Ala Leu
        180                 185                 190 gat gcc agg cct gga tcc ttc acg ctg tta ctg cgg aac cga aag ggc     624
Asp Ala Arg Pro Gly Ser Phe Thr Leu Leu Leu Arg Asn Arg Lys Gly
        195                 200                 205 ttc gtc agg ctc gcc ctg aca cac ggg gca ccc ctg gtg cca atc ttc     672
Phe Val Arg Leu Ala Leu Thr His Gly Ala Pro Leu Val Pro Ile Phe
        210                 215                 220 tcc ttc ggg gag aat gac cta ttt gac cag att ccc aac tct tct ggc     720
Ser Phe Gly Glu Asn Asp Leu Phe Asp Gln Ile Pro Asn Ser Ser Gly
225                 230                 235                 240 tcc tgg tta cgc tat atc cag aat cgg ttg cag aag atc atg ggc atc     768
Ser Trp Leu Arg Tyr Ile Gln Asn Arg Leu Gln Lys Ile Met Gly Ile
                245                 250                 255 tcc ctc cca ctc ttt cat ggc cgt ggt gtc ttc cag tac agc ttt ggt     816
Ser Leu Pro Leu Phe His Gly Arg Gly Val Phe Gln Tyr Ser Phe Gly
        260                 265                 270 tta ata ccc tac cgc cgg ccc atc acc act gtg gtg ggg aag ccc atc     864
Leu Ile Pro Tyr Arg Arg Pro Ile Thr Thr Val Val Gly Lys Pro Ile
        275                 280                 285 gag gta cag aag acg ctg cat ccc tcg gag gag gag gtg aac cag ctg     912
Glu Val Gln Lys Thr Leu His Pro Ser Glu Glu Glu Val Asn Gln Leu
        290                 295                 300 cac cag cgt tat atc aaa gag ctg tgc aac ctc ttc gag gcc cac aaa     960
His Gln Arg Tyr Ile Lys Glu Leu Cys Asn Leu Phe Glu Ala His Lys
305                 310                 315                 320 ctt aag ttc aac atc cct gct gac cag cac ttg gag ttc tgc tga        1005
Leu Lys Phe Asn Ile Pro Ala Asp Gln His Leu Glu Phe Cys *
                325                 330
```

<210> SEQ ID NO 2
<211> LENGTH: 334
<212> TYPE: PRT
<213> ORGANISM: human

<400> SEQUENCE: 2

Met Val Glu Phe Ala Pro Leu Phe Met Pro Trp Glu Arg Arg Leu Gln
1               5                   10                  15

Thr Leu Ala Val Leu Gln Phe Val Phe Ser Phe Leu Ala Leu Ala Glu
            20                  25                  30

Ile Cys Thr Val Gly Phe Ile Ala Leu Leu Phe Thr Arg Phe Trp Leu
        35                  40                  45

Leu Thr Val Leu Tyr Ala Ala Trp Trp Tyr Leu Asp Arg Asp Lys Pro
    50                  55                  60

Arg Gln Gly Gly Arg His Ile Gln Ala Ile Arg Cys Trp Thr Ile Trp
65                  70                  75                  80

Lys Tyr Met Lys Asp Tyr Phe Pro Ile Ser Leu Val Lys Thr Ala Glu
                85                  90                  95

Leu Asp Pro Ser Arg Asn Tyr Ile Ala Gly Phe His Pro His Gly Val
            100                 105                 110

Leu Ala Val Gly Ala Phe Ala Asn Leu Cys Thr Glu Ser Thr Gly Phe
        115                 120                 125

Ser Ser Ile Phe Pro Gly Ile Arg Pro His Leu Met Met Leu Thr Leu
    130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Arg Asn Arg Lys Gly
        195                 200                 205

Phe Val Arg Leu Ala Leu Thr His Gly Ala Pro Leu Val Pro Ile Phe
    210                 215                 220

Ser Phe Gly Glu Asn Asp Leu Phe Asp Gln Ile Pro Asn Ser Ser Gly
225                 230                 235                 240

Ser Trp Leu Arg Tyr Ile Gln Asn Arg Leu Gln Lys Ile Met Gly Ile
                245                 250                 255

Ser Leu Pro Leu Phe His Gly Arg Gly Val Phe Gln Tyr Ser Phe Gly
            260                 265                 270

Leu Ile Pro Tyr Arg Arg Pro Ile Thr Thr Val Val Gly Lys Pro Ile
        275                 280                 285

Glu Val Gln Lys Thr Leu His Pro Ser Glu Glu Val Asn Gln Leu
    290                 295                 300

His Gln Arg Tyr Ile Lys Glu Leu Cys Asn Leu Phe Glu Ala His Lys
305                 310                 315                 320

Leu Lys Phe Asn Ile Pro Ala Asp Gln His Leu Glu Phe Cys
                325                 330

<210> SEQ ID NO 3
<211> LENGTH: 855
<212> TYPE: DNA
<213> ORGANISM: human
<220> FEATURE:
<221> NAME/KEY: CDS
<222> LOCATION: (1)...(855)

```
<400> SEQUENCE: 3 atg gta gag ttc gcg ccc ttg ttt atg ccg tgg gag cgc agg ctg cag      48
Met Val Glu Phe Ala Pro Leu Phe Met Pro Trp Glu Arg Arg Leu Gln
 1               5                  10                  15 aca ctt gct gtc cta cag ttt gtc ttc tcc ttc ttg gca ctg gcc gag      96
Thr Leu Ala Val Leu Gln Phe Val Phe Ser Phe Leu Ala Leu Ala Glu
            20                  25                  30 atc tgc act gtg ggc ttc ata gcc ctg ctg ttt aca aga ttc tgg ctc     144
Ile Cys Thr Val Gly Phe Ile Ala Leu Leu Phe Thr Arg Phe Trp Leu
        35                  40                  45 ctc act gtc ctg tat gcg gcc tgg tgg tat ctg gac cga gac aag cca     192
Leu Thr Val Leu Tyr Ala Ala Trp Trp Tyr Leu Asp Arg Asp Lys Pro
    50                  55                  60 cgg cag ggg ggc cgg cac atc cag gcc atc agg tgc tgg act ata tgg     240
Arg Gln Gly Gly Arg His Ile Gln Ala Ile Arg Cys Trp Thr Ile Trp
65                  70                  75                  80 aag tac atg aag gac tat ttc ccc atc tcg ctg gtc aag act gct gag     288
Lys Tyr Met Lys Asp Tyr Phe Pro Ile Ser Leu Val Lys Thr Ala Glu
                85                  90                  95 ctg gac ccc tct cgg aac tac att gcg ggc ttc cac ccc cat gga gtc     336
Leu Asp Pro Ser Arg Asn Tyr Ile Ala Gly Phe His Pro His Gly Val
            100                 105                 110 ctg gca gtc gga gcc ttt gcc aac ctg tgc act gag agc aca ggc ttc     384
Leu Ala Val Gly Ala Phe Ala Asn Leu Cys Thr Glu Ser Thr Gly Phe
        115                 120                 125 tct tcg atc ttc ccc ggt atc cgc ccc cat ctg atg atg ccg acc ttg     432
Ser Ser Ile Phe Pro Gly Ile Arg Pro His Leu Met Met Pro Thr Leu
    130                 135                 140 tgg ttc cgg gcc ccc ttc ttc aga gat tac atc atg tct gca ggg ttg     480
Trp Phe Arg Ala Pro Phe Phe Arg Asp Tyr Ile Met Ser Ala Gly Leu
145                 150                 155                 160 gtc aca tca gaa aag gag agt gct gct cac att ctg aac agg aag ggt     528
Val Thr Ser Glu Lys Glu Ser Ala Ala His Ile Leu Asn Arg Lys Gly
                165                 170                 175 ggc gga aac ttg ctg ggc atc att gta ggg ggt gcc cag gag gcc ctg     576
Gly Gly Asn Leu Leu Gly Ile Ile Val Gly Gly Ala Gln Glu Ala Leu
            180                 185                 190 gat gcc agg cct gga tcc ttc acg ctg tta ctg cgg aac cga aag ggc     624
Asp Ala Arg Pro Gly Ser Phe Thr Leu Leu Leu Arg Asn Arg Lys Gly
        195                 200                 205 ttc gtc agg ctc gcc ctg aca cac ggg tat caa gcc tct ggg aag agc     672
Phe Val Arg Leu Ala Leu Thr His Gly Tyr Gln Ala Ser Gly Lys Ser
    210                 215                 220 act ctg ggt tca gtt ggc aat tgg caa gga ttt tat ttt ggt ggg aag     720
Thr Leu Gly Ser Val Gly Asn Trp Gln Gly Phe Tyr Phe Gly Gly Lys
225                 230                 235                 240 atg gca gag acg aat gca gat tct att ttg gta gag att ttc agt cca     768
Met Ala Glu Thr Asn Ala Asp Ser Ile Leu Val Glu Ile Phe Ser Pro
                245                 250                 255 ttc aca att aag att ata ttt tgg tgt ctt atg ccc aaa tac cta gaa     816
Phe Thr Ile Lys Ile Ile Phe Trp Cys Leu Met Pro Lys Tyr Leu Glu
            260                 265                 270 aag ttt cca caa cgg aga ctc agt gat cta aga aac tag                 855
Lys Phe Pro Gln Arg Arg Leu Ser Asp Leu Arg Asn *
        275                 280

<210> SEQ ID NO 4
<211> LENGTH: 284
<212> TYPE: PRT
<213> ORGANISM: human
```

```
<400> SEQUENCE: 4

Met Val Glu Phe Ala Pro Leu Phe Met Pro Trp Glu Arg Arg Leu Gln
  1               5                  10                  15

Thr Leu Ala Val Leu Gln Phe Val Phe Ser Phe Leu Ala Leu Ala Glu
             20                  25                  30

Ile Cys Thr Val Gly Phe Ile Ala Leu Leu Phe Thr Arg Phe Trp Leu
             35                  40                  45

Leu Thr Val Leu Tyr Ala Ala Trp Trp Tyr Leu Asp Arg Asp Lys Pro
         50                  55                  60

Arg Gln Gly Gly Arg His Ile Gln Ala Ile Arg Cys Trp Thr Ile Trp
 65                  70                  75                  80

Lys Tyr Met Lys Asp Tyr Phe Pro Ile Ser Leu Val Lys Thr Ala Glu
                 85                  90                  95

Leu Asp Pro Ser Arg Asn Tyr Ile Ala Gly Phe His Pro His Gly Val
                100                 105                 110

Leu Ala Val Gly Ala Phe Ala Asn Leu Cys Thr Glu Ser Thr Gly Phe
            115                 120                 125

Ser Ser Ile Phe Pro Gly Ile Arg Pro His Leu Met Met Pro Thr Leu
130                 135                 140

Trp Phe Arg Ala Pro Phe Phe Arg Asp Tyr Ile Met Ser Ala Gly Leu
145                 150                 155                 160

Val Thr Ser Glu Lys Glu Ser Ala Ala His Ile Leu Asn Arg Lys Gly
                165                 170                 175

Gly Gly Asn Leu Leu Gly Ile Ile Val Gly Gly Ala Gln Glu Ala Leu
            180                 185                 190

Asp Ala Arg Pro Gly Ser Phe Thr Leu Leu Leu Arg Asn Arg Lys Gly
            195                 200                 205

Phe Val Arg Leu Ala Leu Thr His Gly Tyr Gln Ala Ser Gly Lys Ser
        210                 215                 220

Thr Leu Gly Ser Val Gly Asn Trp Gln Gly Phe Tyr Phe Gly Gly Lys
225                 230                 235                 240

Met Ala Glu Thr Asn Ala Asp Ser Ile Leu Val Glu Ile Phe Ser Pro
                245                 250                 255

Phe Thr Ile Lys Ile Ile Phe Trp Cys Leu Met Pro Lys Tyr Leu Glu
                260                 265                 270

Lys Phe Pro Gln Arg Arg Leu Ser Asp Leu Arg Asn
            275                 280

<210> SEQ ID NO 5
<211> LENGTH: 1748
<212> TYPE: DNA
<213> ORGANISM: mus musculus
<220> FEATURE:
<221> NAME/KEY: CDS
<222> LOCATION: (254)...(1012)
<220> FEATURE:
<221> NAME/KEY: misc_feature
<222> LOCATION: (1)...(1748)
<223> OTHER INFORMATION: n = A,T,C or G

<400> SEQUENCE: 5
ccacgcgtcc gtggagttcg cccccctgtt ggtaccatgg gagcgcaggt tacagacctt      60
cgcggtcctt cagtgggtct tctccttcct ggccttggcc cagctctgca tcgtcatctt     120
cgtaggcctc ctattcacaa ggttctggct cttctctgtc ctgtatgcca cctggtggta    180
cctggactgg gacaagccgc ggcagggagg ccggcccatc cagttcttca gacgcttggc    240
```

-continued

| | |
|---|---|
| catatggaag tac atg aag gat tat ttc cct gtc tct ttg gtc aag aca<br>               Met Lys Asp Tyr Phe Pro Val Ser Leu Val Lys Thr<br>                1               5                    10 | 289 |
| gct gag ctg gac cct tcc cgg aac tac atc gcg ggc ttc cac ccc cat<br>Ala Glu Leu Asp Pro Ser Arg Asn Tyr Ile Ala Gly Phe His Pro His<br>       15                    20                  25 | 337 |
| gga gtc cta gca gct gga gcc ttt ctt aac ctg tgc act gaa agc acg<br>Gly Val Leu Ala Ala Gly Ala Phe Leu Asn Leu Cys Thr Glu Ser Thr<br>    30                    35                  40 | 385 |
| ggc ttt acc tcg ctt ttc ccg ggc atc cgc tcc tat ctg atg atg ctg<br>Gly Phe Thr Ser Leu Phe Pro Gly Ile Arg Ser Tyr Leu Met Met Leu<br>45                    50                  55                  60 | 433 |
| act gtg tgg ttc cgg gcc ccc ttc ttc cga gat tac atc atg tct ggg<br>Thr Val Trp Phe Arg Ala Pro Phe Phe Arg Asp Tyr Ile Met Ser Gly<br>             65                    70                  75 | 481 |
| ggg ctg gtc tca tca gaa aag gtg agt gcc gat cac att ctg tcc agg<br>Gly Leu Val Ser Ser Glu Lys Val Ser Ala Asp His Ile Leu Ser Arg<br>          80                    85                  90 | 529 |
| aag ggc ggc ggg aac ttg ctt gcc atc atc gtt ggg ggc gcg cag gag<br>Lys Gly Gly Gly Asn Leu Leu Ala Ile Ile Val Gly Gly Ala Gln Glu<br>       95                  100               105 | 577 |
| gca ctg gac gcc agg cct gga gcc tac agg ctg ctg ctg aag aat cgc<br>Ala Leu Asp Ala Arg Pro Gly Ala Tyr Arg Leu Leu Leu Lys Asn Arg<br>110                   115               120 | 625 |
| aag ggc ttc atc atg ctc gcc ctg atg cat ggg gca gct ctt tgt gca<br>Lys Gly Phe Ile Met Leu Ala Leu Met His Gly Ala Ala Leu Cys Ala<br>125                   130               135               140 | 673 |
| atc ttc tcc ttt gga gaa aac aac ctg ttc aac cag gtt gag aac acc<br>Ile Phe Ser Phe Gly Glu Asn Asn Leu Phe Asn Gln Val Glu Asn Thr<br>               145               150               155 | 721 |
| cct ggt acc tgg ctg cgc tgg atc cag aac cgg cta cag aag atc atg<br>Pro Gly Thr Trp Leu Arg Trp Ile Gln Asn Arg Leu Gln Lys Ile Met<br>           160               165               170 | 769 |
| ggc atc tcc ctc cct ctc ttc cac ggc aga ggt gtc ttc cag tac agc<br>Gly Ile Ser Leu Pro Leu Phe His Gly Arg Gly Val Phe Gln Tyr Ser<br>175                   180               185 | 817 |
| ttt ggc ctc atg ccc ttc cgc cag ccc atc acc acc ata gtg ggg aag<br>Phe Gly Leu Met Pro Phe Arg Gln Pro Ile Thr Thr Ile Val Gly Lys<br>    190                    195               200 | 865 |
| ccc atc gag gtg cag atg aca cca cag ccc tca agg gag gag gtg gac<br>Pro Ile Glu Val Gln Met Thr Pro Gln Pro Ser Arg Glu Glu Val Asp<br>205                   210               215               220 | 913 |
| cgg ctt cac cag cgc tat atc aag gag ctc tgc aag ctc ttt gag gag<br>Arg Leu His Gln Arg Tyr Ile Lys Glu Leu Cys Lys Leu Phe Glu Glu<br>               225               230               235 | 961 |
| cac aaa ctc aag ttc aac gtc cct gag gac cag cat ctg gag ttc tgc<br>His Lys Leu Lys Phe Asn Val Pro Glu Asp Gln His Leu Glu Phe Cys<br>           240               245               250 | 1009 |
| taa gtgtctccag ccggaagaca gctgcatctg agcgcctgca ggagtgtggg<br>* | 1062 |
| attagggga cttccacagc caccagacac tcctacaaac ctagccacaa ctgccaagat | 1122 |
| ggaagagggg gcagctccta atcctgggat ttgaacctgc agccaaagct ctgaggtctc | 1182 |
| cctgtccttg gcctgtctgc acatctgtag aatgggggaa aagcaggcag agagaaattc | 1242 |
| ctgaggtctc ttcccacagt tgtaatgtca ttcaaacatg accaaaggac aaacagggag | 1302 |
| aaagagaaca aaactgttct tcatctaccc ttgagggaca gtgcaagaga agccagcacc | 1362 |
| ccaggcctcc ctgtgcatgg tccctgatgc tgcttcttcc ctctgaggca gagacgggga | 1422 |

-continued

```
gccaagtctg ccctggcacc tactctatgt ttcttcagat tctgggtcct ctgagctatg   1482
ataccaaagg agcccagaag gcagataagg agggcagggg tcactgacta tgaccgaggg   1542
taggtctcct tcccatatcc tgagcctcag tttcccccacc cttaatgacc tgggagcgcc   1602
acactgctca ccacagaggc tccaccagag accctcttac tcatgctttc tagtgaactc   1662
cagcctcttt cttggcactg aagggcagca ctgtacatgt tacctcaata aatgaaagga   1722
gtctgtctta aannnnnnnn nnnnnn                                        1748
```

<210> SEQ ID NO 6
<211> LENGTH: 252
<212> TYPE: PRT
<213> ORGANISM: mus musculus

<400> SEQUENCE: 6

```
Met Lys Asp Tyr Phe Pro Val Ser Leu Val Lys Thr Ala Glu Leu Asp
 1               5                  10                  15

Pro Ser Arg Asn Tyr Ile Ala Gly Phe His Pro His Gly Val Leu Ala
             20                  25                  30

Ala Gly Ala Phe Leu Asn Leu Cys Thr Glu Ser Thr Gly Phe Thr Ser
         35                  40                  45

Leu Phe Pro Gly Ile Arg Ser Tyr Leu Met Met Leu Thr Val Trp Phe
     50                  55                  60

Arg Ala Pro Phe Phe Arg Asp Tyr Ile Met Ser Gly Gly Leu Val Ser
 65                  70                  75                  80

Ser Glu Lys Val Ser Ala Asp His Ile Leu Ser Arg Lys Gly Gly Gly
                 85                  90                  95

Asn Leu Leu Ala Ile Ile Val Gly Gly Ala Gln Glu Ala Leu Asp Ala
            100                 105                 110

Arg Pro Gly Ala Tyr Arg Leu Leu Leu Lys Asn Arg Lys Gly Phe Ile
        115                 120                 125

Met Leu Ala Leu Met His Gly Ala Ala Leu Cys Ala Ile Phe Ser Phe
    130                 135                 140

Gly Glu Asn Asn Leu Phe Asn Gln Val Glu Asn Thr Pro Gly Thr Trp
145                 150                 155                 160

Leu Arg Trp Ile Gln Asn Arg Leu Gln Lys Ile Met Gly Ile Ser Leu
                165                 170                 175

Pro Leu Phe His Gly Arg Gly Val Phe Gln Tyr Ser Phe Gly Leu Met
            180                 185                 190

Pro Phe Arg Gln Pro Ile Thr Thr Ile Val Gly Lys Pro Ile Glu Val
        195                 200                 205

Gln Met Thr Pro Gln Pro Ser Arg Glu Glu Val Asp Arg Leu His Gln
    210                 215                 220

Arg Tyr Ile Lys Glu Leu Cys Lys Leu Phe Glu Glu His Lys Leu Lys
225                 230                 235                 240

Phe Asn Val Pro Glu Asp Gln His Leu Glu Phe Cys
                245                 250
```

<210> SEQ ID NO 7
<211> LENGTH: 1263
<212> TYPE: DNA
<213> ORGANISM: human
<220> FEATURE:
<221> NAME/KEY: CDS
<222> LOCATION: (171)...(1196)

<400> SEQUENCE: 7

```
cccactcaca cacctmmska wmrsrmgyyr myccacgcgt ccgtttgcga cttagccagg        60 ccccaaagc tgggctcctg tagggagaaa gtctgcccag gtccacatcc aagccttcat       120
cgtttgtcct ccgggttctg ggatcctgct ggaagagggg agcttctgca atg gga         176
                                                        Met Gly
                                                          1 gtt gcc aca acc ctg cag ccc cca acc act tcc aaa acc ttg cag aag        224
Val Ala Thr Thr Leu Gln Pro Pro Thr Thr Ser Lys Thr Leu Gln Lys
        5                  10                  15 cag cat cta gaa gca gtg ggc gcc tac caa tat gtg ctc act ttc ctc        272
Gln His Leu Glu Ala Val Gly Ala Tyr Gln Tyr Val Leu Thr Phe Leu
 20                  25                  30 ttc atg ggc cct ttc ttc tcc ctt ctt gtc ttt gtc ctc ctc ttc acg        320
Phe Met Gly Pro Phe Phe Ser Leu Leu Val Phe Val Leu Leu Phe Thr
 35                  40                  45                  50 tca ctc tgg ccc ttc tct gtt ttt tac ttg gtg tgg ctc tat gtg gac        368
Ser Leu Trp Pro Phe Ser Val Phe Tyr Leu Val Trp Leu Tyr Val Asp
                 55                  60                  65 tgg gac aca ccc aac caa ggt gga agg cgt tcg gag tgg ata agg aac        416
Trp Asp Thr Pro Asn Gln Gly Gly Arg Arg Ser Glu Trp Ile Arg Asn
             70                  75                  80 cgg gca att tgg aga caa cta agg gat tat tat cct gtc aag ctg gtg        464
Arg Ala Ile Trp Arg Gln Leu Arg Asp Tyr Tyr Pro Val Lys Leu Val
         85                  90                  95 aaa aca gca gag ctg ccc ccg gat cgg aac tac gtg ctg ggc gcc cac        512
Lys Thr Ala Glu Leu Pro Pro Asp Arg Asn Tyr Val Leu Gly Ala His
100                 105                 110 cct cat ggg atc atg tgt aca ggc ttc ctc tgt aat ttc tcc acc gag        560
Pro His Gly Ile Met Cys Thr Gly Phe Leu Cys Asn Phe Ser Thr Glu
115                 120                 125                 130 agc aat ggc ttc tcc cag ctc ttc ccg ggg ctc cgg ccc tgg tta gcc        608
Ser Asn Gly Phe Ser Gln Leu Phe Pro Gly Leu Arg Pro Trp Leu Ala
                135                 140                 145 gtg ctg gct ggc ctc ttc tac ctc ccg gtc tat cgc gac tac atc atg        656
Val Leu Ala Gly Leu Phe Tyr Leu Pro Val Tyr Arg Asp Tyr Ile Met
            150                 155                 160 tcc ttt gga ctc tgt ccg gtg agc cgc cag agc ctg gac ttc atc ctg        704
Ser Phe Gly Leu Cys Pro Val Ser Arg Gln Ser Leu Asp Phe Ile Leu
        165                 170                 175 tcc cag ccc cag ctc ggg cag gcc gtg gtc atc atg gtg ggg ggt gcg        752
Ser Gln Pro Gln Leu Gly Gln Ala Val Val Ile Met Val Gly Gly Ala
180                 185                 190 cac gag gcc ctg tat tca gtc ccc ggg gag cac tgc ctt acg ctc cag        800
His Glu Ala Leu Tyr Ser Val Pro Gly Glu His Cys Leu Thr Leu Gln
195                 200                 205                 210 aag cgc aaa ggc ttc gtg cgc ctg gcg ctg agg cac ggg gcg tcc ctg        848
Lys Arg Lys Gly Phe Val Arg Leu Ala Leu Arg His Gly Ala Ser Leu
                215                 220                 225 gtg ccc gtg tac tcc ttt ggg gag aat gac atc ttt aga ctt aag gct        896
Val Pro Val Tyr Ser Phe Gly Glu Asn Asp Ile Phe Arg Leu Lys Ala
            230                 235                 240 ttt gcc aca ggc tcc tgg cag cat tgg tgc cag ctc acc ttc aag aag        944
Phe Ala Thr Gly Ser Trp Gln His Trp Cys Gln Leu Thr Phe Lys Lys
        245                 250                 255 ctc atg ggc ttc tct cct tgc atc ttc tgg ggt cgc ggt ctc ttc tca        992
Leu Met Gly Phe Ser Pro Cys Ile Phe Trp Gly Arg Gly Leu Phe Ser
260                 265                 270
```

```
gcc acc tcc tgg ggc ctg ctg ccc ttt gct gtg ccc atc acc act gtg    1040
Ala Thr Ser Trp Gly Leu Leu Pro Phe Ala Val Pro Ile Thr Thr Val
275                 280                 285                 290 gtg ggc cgc ccc atc ccc gtc ccc cag cgc ctc cac ccc acc gag gag    1088
Val Gly Arg Pro Ile Pro Val Pro Gln Arg Leu His Pro Thr Glu Glu
            295                 300                 305 gaa gtc aat cac tat cac gcc ctc tac atg acg gcc ctg gag cag ctc    1136
Glu Val Asn His Tyr His Ala Leu Tyr Met Thr Ala Leu Glu Gln Leu
        310                 315                 320 ttc gag gag cac aag gaa agc tgt ggg gtc ccc gct tcc acc tgc ctc    1184
Phe Glu Glu His Lys Glu Ser Cys Gly Val Pro Ala Ser Thr Cys Leu
    325                 330                 335 acc ttc atc tag gcctggccgc ggcctttcgc tgagcccctg agcccaaggc        1236
Thr Phe Ile *
    340 actgagacct ccacccactg tggactc                                      1263

<210> SEQ ID NO 8
<211> LENGTH: 341
<212> TYPE: PRT
<213> ORGANISM: human

<400> SEQUENCE: 8

Met Gly Val Ala Thr Thr Leu Gln Pro Pro Thr Thr Ser Lys Thr Leu
1               5                   10                  15

Gln Lys Gln His Leu Glu Ala Val Gly Ala Tyr Gln Tyr Val Leu Thr
            20                  25                  30

Phe Leu Phe Met Gly Pro Phe Phe Ser Leu Leu Val Phe Leu Leu
        35                  40                  45

Phe Thr Ser Leu Trp Pro Phe Ser Val Phe Tyr Leu Val Trp Leu Tyr
    50                  55                  60

Val Asp Trp Asp Thr Pro Asn Gln Gly Gly Arg Arg Ser Glu Trp Ile
65                  70                  75                  80

Arg Asn Arg Ala Ile Trp Arg Gln Leu Arg Asp Tyr Tyr Pro Val Lys
                85                  90                  95

Leu Val Lys Thr Ala Glu Leu Pro Pro Asp Arg Asn Tyr Val Leu Gly
            100                 105                 110

Ala His Pro His Gly Ile Met Cys Thr Gly Phe Leu Cys Asn Phe Ser
        115                 120                 125

Thr Glu Ser Asn Gly Phe Ser Gln Leu Phe Pro Gly Leu Arg Pro Trp
    130                 135                 140

Leu Ala Val Leu Ala Gly Leu Phe Tyr Leu Pro Val Tyr Arg Asp Tyr
145                 150                 155                 160

Ile Met Ser Phe Gly Leu Cys Pro Val Ser Arg Gln Ser Leu Asp Phe
                165                 170                 175

Ile Leu Ser Gln Pro Gln Leu Gly Gln Ala Val Val Ile Met Val Gly
            180                 185                 190

Gly Ala His Glu Ala Leu Tyr Ser Val Pro Gly Glu His Cys Leu Thr
        195                 200                 205

Leu Gln Lys Arg Lys Gly Phe Val Arg Leu Ala Leu Arg His Gly Ala
    210                 215                 220

Ser Leu Val Pro Val Tyr Ser Phe Gly Glu Asn Asp Ile Phe Arg Leu
225                 230                 235                 240

Lys Ala Phe Ala Thr Gly Ser Trp Gln His Trp Cys Gln Leu Thr Phe
                245                 250                 255
```

```
                Lys Lys Leu Met Gly Phe Ser Pro Cys Ile Phe Trp Gly Arg Gly Leu
                            260                 265                 270

Phe Ser Ala Thr Ser Trp Gly Leu Leu Pro Phe Ala Val Pro Ile Thr
                        275                 280                 285

Thr Val Val Gly Arg Pro Ile Pro Val Pro Gln Arg Leu His Pro Thr
                    290                 295                 300

Glu Glu Glu Val Asn His Tyr His Ala Leu Tyr Met Thr Ala Leu Glu
                305                 310                 315                 320

Gln Leu Phe Glu Glu His Lys Glu Ser Cys Gly Val Pro Ala Ser Thr
                                325                 330                 335

Cys Leu Thr Phe Ile
                            340

<210> SEQ ID NO 9
<211> LENGTH: 2428
<212> TYPE: DNA
<213> ORGANISM: human
<220> FEATURE:
<221> NAME/KEY: CDS
<222> LOCATION: (220)...(1386)

<400> SEQUENCE: 9
agcgggctgc ggctgccgcc tctgctgggg tctaggctgt ttctctcgcg ccaccactgg        60
ccgccggccg cagctccagg tgtcctagcc gcccagcctc gacgccgtcc cgggaccccc       120
gtgctctgcg cgaagccctg gccccggggg ccggggcatg gccaggggc gcggggtgaa        180 gcggcttccc gcggggccgt gactgggcgg gcttcagcc atg aag acc ctc ata          234
                                            Met Lys Thr Leu Ile
                                              1               5 gcc gcc tac tcc ggg gtc ctg cgc ggc gag cgt cag gcc gag gct gac          282
Ala Ala Tyr Ser Gly Val Leu Arg Gly Glu Arg Gln Ala Glu Ala Asp
             10                  15                  20 cgg agc cag cgc tct cac gga gga cct gcg ctg tcg cgc gag ggg tct          330
Arg Ser Gln Arg Ser His Gly Gly Pro Ala Leu Ser Arg Glu Gly Ser
         25                  30                  35 ggg aga tgg ggc act gga tcc agc atc ctc tcc gcc ctc cag gac ctc          378
Gly Arg Trp Gly Thr Gly Ser Ser Ile Leu Ser Ala Leu Gln Asp Leu
     40                  45                  50 ttc tct gtc acc tgg ctc aat agg tcc aag gtg gaa aag cag cta cag          426
Phe Ser Val Thr Trp Leu Asn Arg Ser Lys Val Glu Lys Gln Leu Gln
 55                  60                  65 gtc atc tca gtg ctc cag tgg gtc ctg tcc ttc ctt gta ctg gga gtg          474
Val Ile Ser Val Leu Gln Trp Val Leu Ser Phe Leu Val Leu Gly Val
 70                  75                  80                  85 gcc tgc agt gcc atc ctc atg tac ata ttc tgc act gat tgc tgg ctc          522
Ala Cys Ser Ala Ile Leu Met Tyr Ile Phe Cys Thr Asp Cys Trp Leu
                 90                  95                 100 atc gct gtg ctc tac ttc act tgg ctg gtg ttt gac tgg aac aca ccc          570
Ile Ala Val Leu Tyr Phe Thr Trp Leu Val Phe Asp Trp Asn Thr Pro
            105                 110                 115 aag aaa ggt ggc agg agg tca cag tgg gtc cga aac tgg gct gtg tgg          618
Lys Lys Gly Gly Arg Arg Ser Gln Trp Val Arg Asn Trp Ala Val Trp
        120                 125                 130 cgc tac ttt cga gac tac ttt ccc atc cag ctg gtg aag aca cac aac          666
Arg Tyr Phe Arg Asp Tyr Phe Pro Ile Gln Leu Val Lys Thr His Asn
    135                 140                 145 ctg ctg acc acc agg aac tat atc ttt gga tac cac ccc cat ggt atc          714
Leu Leu Thr Thr Arg Asn Tyr Ile Phe Gly Tyr His Pro His Gly Ile
150                 155                 160                 165
```

```
atg ggc ctg ggt gcc ttc tgc aac ttc agc aca gag gcc aca gaa gtg      762
Met Gly Leu Gly Ala Phe Cys Asn Phe Ser Thr Glu Ala Thr Glu Val
            170                 175                 180 agc aag aag ttc cca ggc ata cgg cct tac ctg gct aca ctg gca ggc      810
Ser Lys Lys Phe Pro Gly Ile Arg Pro Tyr Leu Ala Thr Leu Ala Gly
        185                 190                 195 aac ttc cga atg cct gtg ttg agg gag tac ctg atg tct gga ggt atc      858
Asn Phe Arg Met Pro Val Leu Arg Glu Tyr Leu Met Ser Gly Gly Ile
            200                 205                 210 tgc cct gtc agc cgg gac acc ata gac tat ttg ctt tca aag aat ggg      906
Cys Pro Val Ser Arg Asp Thr Ile Asp Tyr Leu Leu Ser Lys Asn Gly
            215                 220                 225 agt ggc aat gct atc atc atc gtg gtc ggg ggt gcg gct gag tct ctg      954
Ser Gly Asn Ala Ile Ile Ile Val Val Gly Gly Ala Ala Glu Ser Leu
230                 235                 240                 245 agc tcc atg cct ggc aag aat gca gtc acc ctg cgg aac cgc aag ggc     1002
Ser Ser Met Pro Gly Lys Asn Ala Val Thr Leu Arg Asn Arg Lys Gly
                250                 255                 260 ttt gtg aaa ctg gcc ctg cgt cat gga gct gac ctg gtt ccc atc tac     1050
Phe Val Lys Leu Ala Leu Arg His Gly Ala Asp Leu Val Pro Ile Tyr
            265                 270                 275 tcc ttt gga gag aat gaa gtg tac aag cag gtg atc ttc gag gag ggc     1098
Ser Phe Gly Glu Asn Glu Val Tyr Lys Gln Val Ile Phe Glu Glu Gly
            280                 285                 290 tcc tgg ggc cga tgg gtc cag aag aag ttc cag aaa tac att ggt ttc     1146
Ser Trp Gly Arg Trp Val Gln Lys Lys Phe Gln Lys Tyr Ile Gly Phe
            295                 300                 305 gcc cca tgc atc ttc cat ggt cga ggc ctc ttc tcc tcc gac acc tgg     1194
Ala Pro Cys Ile Phe His Gly Arg Gly Leu Phe Ser Ser Asp Thr Trp
310                 315                 320                 325 ggg ctg gtg ccc tac tcc aag ccc atc acc act gtt gtg gga gag ccc     1242
Gly Leu Val Pro Tyr Ser Lys Pro Ile Thr Thr Val Val Gly Glu Pro
                330                 335                 340 atc acc atc ccc aag ctg gag cac cca acc cag caa gac atc gac ctg     1290
Ile Thr Ile Pro Lys Leu Glu His Pro Thr Gln Gln Asp Ile Asp Leu
            345                 350                 355 tac cac acc atg tac atg gag gcc ctg gtg aag ctc ttc gac aag cac     1338
Tyr His Thr Met Tyr Met Glu Ala Leu Val Lys Leu Phe Asp Lys His
            360                 365                 370 aag acc aag ttc ggc ctc ccg gag act gag gtc ctg gag gtg aac tga     1386
Lys Thr Lys Phe Gly Leu Pro Glu Thr Glu Val Leu Glu Val Asn  *
375                 380                 385 gccagccttc ggggccaatt ccctggagga accagctgca aatcactttt ttgctctgta   1446
aatttggaag tgtcatgggt gtctgtgggt tatttaaaag aaattataac aattttgcta   1506
aaccattaca atgttaggtc ttttttaaga aggaaaagt cagtatttca agttctttca    1566
cttccagctt gccctgttct aggtggtggc taaatctggg cctaatctgg gtggctcagc   1626
taacctctct tcttcccttc ctgaagtgac aaaggaaact cagtcttctt ggggaagaag   1686
gattgccatt agtgacttgg accagttaga tgattcactt tttgcccctca gggatgagag   1746
gcgaaagcca cttctcatac aagcccctt attgccacta ccccacgctc gtctagtcct    1806
gaaactgcag gaccagtttc tctgccaagg ggaggagttg gagagcacag ttgccccgtt   1866
gtgtgagggc agtagtaggc atctggaatg ctccagtttg atctcccttc tgccaccct    1926
acctcacccc tagtcactca tatcggagcc tggactggcc tccaggatga ggatgggggt   1986
ggcaatgaca ccctgcaggg gaaggactg ccccccatgc accattgcag ggaggatgcc    2046
gccaccatga gctaggtgga gtaactggtt tttcttgggt ggctgatgac atggatgcag   2106
```

-continued

```
cacagactca gccttggcct ggagcacatg cttactggtg gcctcagttt accttcccca    2166
gatcctagat tctggatgtg aggaagagat ccctcttcag aaggggcctg gccttctgag    2226
cagcagatta gttccaaagc aggtggcccc cgaacccaag cctcactttt ctgtgccttc    2286
ctgagggggt tgggccgggg aggaaaccca accctctcct gtgtgttctg ttatctcttg    2346
atgagatcat tgcaccatgt cagacttttg tatatgcctt gaaataaat gaaagtgaga     2406 atccaaaaaa aaaaaaaaaa aa                                              2428
```

<210> SEQ ID NO 10
<211> LENGTH: 388
<212> TYPE: PRT
<213> ORGANISM: human

<400> SEQUENCE: 10

```
Met Lys Thr Leu Ile Ala Ala Tyr Ser Gly Val Leu Arg Gly Glu Arg
  1               5                  10                  15

Gln Ala Glu Ala Asp Arg Ser Gln Arg Ser His Gly Gly Pro Ala Leu
             20                  25                  30

Ser Arg Glu Gly Ser Gly Arg Trp Gly Thr Gly Ser Ser Ile Leu Ser
         35                  40                  45

Ala Leu Gln Asp Leu Phe Ser Val Thr Trp Leu Asn Arg Ser Lys Val
     50                  55                  60

Glu Lys Gln Leu Gln Val Ile Ser Val Leu Gln Trp Val Leu Ser Phe
 65                  70                  75                  80

Leu Val Leu Gly Val Ala Cys Ser Ala Ile Leu Met Tyr Ile Phe Cys
                 85                  90                  95

Thr Asp Cys Trp Leu Ile Ala Val Leu Tyr Phe Thr Trp Leu Val Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
    130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Ser Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Arg Asn Arg Lys Gly Phe Val Lys Leu Ala Leu Arg His Gly Ala Asp
            260                 265                 270

Leu Val Pro Ile Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320
```

```
Ser Ser Asp Thr Trp Gly Leu Val Pro Tyr Ser Lys Pro Ile Thr Thr
            325                 330                 335

Val Val Gly Glu Pro Ile Thr Ile Pro Lys Leu Glu His Pro Thr Gln
            340                 345                 350

Gln Asp Ile Asp Leu Tyr His Thr Met Tyr Met Glu Ala Leu Val Lys
            355                 360                 365

Leu Phe Asp Lys His Lys Thr Lys Phe Gly Leu Pro Glu Thr Glu Val
    370                 375                 380

Leu Glu Val Asn
385

<210> SEQ ID NO 11
<211> LENGTH: 2262
<212> TYPE: DNA
<213> ORGANISM: mus musculus
<220> FEATURE:
<221> NAME/KEY: CDS
<222> LOCATION: (207)...(1373)

<400> SEQUENCE: 11
```

| | |
|---|---|
| ggtggccgcg cttcgctggc tttctgctca tctagggtgg cagcggctac ctacctcagc | 60 |
| tctcgccctg ctgccgccac ggcctgggcg ctgtccctca gctcccggag ctcagcgcga | 120 |
| agccctggcc ccggcggccg ggcatgggt caggggcgcg gcgtgaggcg gctttctgca | 180 |
| cggccgtgac gtgcattggc ttcagc atg aag acc ctc atc gcc gcc tac tcc | 233 |
|     Met Lys Thr Leu Ile Ala Ala Tyr Ser | |
|     1               5 | |
| ggg gtc ctg cgg ggt gag cgt cgg gcg gaa gct gcc cgc agc gaa aac | 281 |
| Gly Val Leu Arg Gly Glu Arg Arg Ala Glu Ala Ala Arg Ser Glu Asn | |
| 10              15                  20                  25 | |
| aag aat aaa gga tct gcc ctg tca cgc gag ggg tct ggg cga tgg ggc | 329 |
| Lys Asn Lys Gly Ser Ala Leu Ser Arg Glu Gly Ser Gly Arg Trp Gly | |
|             30                  35                  40 | |
| act ggc tcc agc atc ctc tca gcc ctc caa gac atc ttc tct gtc acc | 377 |
| Thr Gly Ser Ser Ile Leu Ser Ala Leu Gln Asp Ile Phe Ser Val Thr | |
|         45                  50                  55 | |
| tgg ctc aac aga tct aag gtg gaa aaa cag ctg cag gtc atc tca gta | 425 |
| Trp Leu Asn Arg Ser Lys Val Glu Lys Gln Leu Gln Val Ile Ser Val | |
|     60                  65                  70 | |
| cta caa tgg gtc cta tcc ttc ctg gtg cta gga gtg gcc tgc agt gtc | 473 |
| Leu Gln Trp Val Leu Ser Phe Leu Val Leu Gly Val Ala Cys Ser Val | |
| 75                  80                  85 | |
| atc ctc atg tac acc ttc tgc aca gac tgc tgg ctg ata gct gtg ctc | 521 |
| Ile Leu Met Tyr Thr Phe Cys Thr Asp Cys Trp Leu Ile Ala Val Leu | |
| 90                  95                  100                 105 | |
| tac ttc acc tgg ctg gca ttt gac tgg aac acg ccc aag aaa ggt ggc | 569 |
| Tyr Phe Thr Trp Leu Ala Phe Asp Trp Asn Thr Pro Lys Lys Gly Gly | |
|             110                 115                 120 | |
| agg aga tcg cag tgg gtg cga aac tgg gcc gtg tgg cgc tac ttc cga | 617 |
| Arg Arg Ser Gln Trp Val Arg Asn Trp Ala Val Trp Arg Tyr Phe Arg | |
|         125                 130                 135 | |
| gac tac ttt ccc atc cag ctg gtg aag aca cac aac ctg ctg acc acc | 665 |
| Asp Tyr Phe Pro Ile Gln Leu Val Lys Thr His Asn Leu Leu Thr Thr | |
|     140                 145                 150 | |
| agg aac tat atc ttt gga tac cac ccc cat ggc atc atg ggc ctg ggt | 713 |
| Arg Asn Tyr Ile Phe Gly Tyr His Pro His Gly Ile Met Gly Leu Gly | |
| 155                 160                 165 | |
| gcc ttc tgt aac ttc agc aca gag gct act gaa gtc agc aag aag ttt | 761 |
| Ala Phe Cys Asn Phe Ser Thr Glu Ala Thr Glu Val Ser Lys Lys Phe | |
| 170                 175                 180                 185 | |

```
cct ggc ata agg ccc tat ttg gct acg ttg gct ggt aac ttc cgg atg          809
Pro Gly Ile Arg Pro Tyr Leu Ala Thr Leu Ala Gly Asn Phe Arg Met
            190                 195                 200 cct gtg ctt cgc gag tac ctg atg tct gga ggc atc tgc cct gtc aac          857
Pro Val Leu Arg Glu Tyr Leu Met Ser Gly Gly Ile Cys Pro Val Asn
            205                 210                 215 cga gac acc ata gac tac ttg ctc tcc aag aat ggg agt ggc aat gct          905
Arg Asp Thr Ile Asp Tyr Leu Leu Ser Lys Asn Gly Ser Gly Asn Ala
            220                 225                 230 atc atc atc gtg gtg gga ggt gca gct gag tcc ctg agc tcc atg cct          953
Ile Ile Ile Val Val Gly Gly Ala Ala Glu Ser Leu Ser Ser Met Pro
            235                 240                 245 ggc aag aac gca gtc acc ctg aag aac cgc aaa ggc ttt gtg aag ctg         1001
Gly Lys Asn Ala Val Thr Leu Lys Asn Arg Lys Gly Phe Val Lys Leu
250                 255                 260                 265 gcc ctg cgc cat gga gct gat ctg gtt ccc act tat tcc ttt gga gag         1049
Ala Leu Arg His Gly Ala Asp Leu Val Pro Thr Tyr Ser Phe Gly Glu
            270                 275                 280 aat gag gta tac aag cag gtg atc ttt gag gag ggt tcc tgg ggc cga         1097
Asn Glu Val Tyr Lys Gln Val Ile Phe Glu Glu Gly Ser Trp Gly Arg
            285                 290                 295 tgg gtc cag aag aag ttc cag aag tat att ggt ttc gcc ccc tgc atc         1145
Trp Val Gln Lys Lys Phe Gln Lys Tyr Ile Gly Phe Ala Pro Cys Ile
            300                 305                 310 ttc cat ggc cga ggc ctc ttc tcc tct gac acc tgg ggg ctg gtg ccc         1193
Phe His Gly Arg Gly Leu Phe Ser Ser Asp Thr Trp Gly Leu Val Pro
            315                 320                 325 tac tcc aag ccc atc acc acc gtc gtg ggg gag ccc atc act gtc ccc         1241
Tyr Ser Lys Pro Ile Thr Thr Val Val Gly Glu Pro Ile Thr Val Pro
330                 335                 340                 345 aag ctg gag cac ccg acc cag aaa gac atc gac ctg tac cat gcc atg         1289
Lys Leu Glu His Pro Thr Gln Lys Asp Ile Asp Leu Tyr His Ala Met
            350                 355                 360 tac atg gag gcc ctg gtg aag ctc ttt gac aat cac aag acc aaa ttt         1337
Tyr Met Glu Ala Leu Val Lys Leu Phe Asp Asn His Lys Thr Lys Phe
            365                 370                 375 ggc ctt cca gag act gag gtg ctg gag gtg aac tga cccagccctc              1383
Gly Leu Pro Glu Thr Glu Val Leu Glu Val Asn  *
            380                 385 gcgtgccagc tcctgggagg gacgactgca gatccttttc taccgagttc ttgagtgcat       1443
tttgttctgt aaatttggaa gcgtcatggg tgtctgtggg ttatttaaaa gaaattataa       1503
tgtgttaaac cattgcaatg ttagatgttt ttttaagaag ggaagagtca gtattttaag       1563
ctcacttcta gtgtgtcctg ctcaaggtgg aggctgatat ttatgggcct tggtggtttc       1623
ttacccaccc cttctagcgt tccccagacg acagacactt ggccctggct agctgggcaa       1683
gggcagtcct tagtgactcc agggattctt gagaggcaga ggccatgtcc cacccgtggc       1743
tgcaggtcgg gttcctcgta ccaagggag gctgagggca cagctggccc cacttgggga       1803
gggtagataa catctggact gcccggcttg gtctctgct cctcacccta gccctcttct        1863
ccaatctgag cctaccctgg cctcctgtct cctggctagg gacacggctg tcccacaggt       1923
gccgtcttgg gttatctcgc tgctgttggc tggtttcact ctggaggttg gcaccatgga       1983
cacagctcag cgttgctctg gcgcatatcc tcctgagcca caccccaagt ctggtgtgag       2043
gaagggcttc tcttctcttc acagaggtgc ctggcttcct gtgcagcaca ctgggtccag       2103
gacaggaggc cccccccca aaccaagcct cacgtgtgtg cctttatgag gcgttgggag        2163
```

```
aaagctaccc tcctgtgtat tctgttttct ccatgagatt gttgtgccat gtcacacttt    2223
tgtatattcc tagactaata aatggaaaca agaacagcc                           2262
```

<210> SEQ ID NO 12
<211> LENGTH: 388
<212> TYPE: PRT
<213> ORGANISM: mus musculus

<400> SEQUENCE: 12

```
Met Lys Thr Leu Ile Ala Ala Tyr Ser Gly Val Leu Arg Gly Glu Arg
 1               5                  10                  15

Arg Ala Glu Ala Ala Arg Ser Glu Asn Lys Asn Lys Gly Ser Ala Leu
                20                  25                  30

Ser Arg Glu Gly Ser Gly Arg Trp Gly Thr Gly Ser Ser Ile Leu Ser
            35                  40                  45

Ala Leu Gln Asp Ile Phe Ser Val Thr Trp Leu Asn Arg Ser Lys Val
        50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
    210                 215                 220

Leu Ser Lys Asn Gly Ser Gly Asn Ala Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Val Pro Lys Leu Glu His Pro Thr Gln
            340                 345                 350
```

```
Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
    370                 375                 380

Leu Glu Val Asn
385

<210> SEQ ID NO 13
<211> LENGTH: 1279
<212> TYPE: DNA
<213> ORGANISM: human
<220> FEATURE:
<221> NAME/KEY: CDS
<222> LOCATION: (42)...(1028)

<400> SEQUENCE: 13
actgttctga gatctttgcc tccctcaggc tcccgagaat c atg gct cat tcc aag      56
                                            Met Ala His Ser Lys
                                              1               5 cag cct agt cac ttc cag agt ctg atg ctt ctg cag tgg cct ttg agc      104
Gln Pro Ser His Phe Gln Ser Leu Met Leu Leu Gln Trp Pro Leu Ser
             10                  15                  20 tac ctt gcc atc ttt tgg atc ttg cag cca ttg ttc gtc tac ctg ctg      152
Tyr Leu Ala Ile Phe Trp Ile Leu Gln Pro Leu Phe Val Tyr Leu Leu
         25                  30                  35 ttt aca tcc ttg tgg ccg cta cca gtg ctt tac ttt gcc tgg ttg ttc      200
Phe Thr Ser Leu Trp Pro Leu Pro Val Leu Tyr Phe Ala Trp Leu Phe
     40                  45                  50 ctg gac tgg aag acc cca gag cga ggt ggc agg cgt tcg gcc tgg gta      248
Leu Asp Trp Lys Thr Pro Glu Arg Gly Gly Arg Arg Ser Ala Trp Val
 55                  60                  65 agg aac tgg tgt gtc tgg acc cac atc agg gac tat ttc ccc att acg      296
Arg Asn Trp Cys Val Trp Thr His Ile Arg Asp Tyr Phe Pro Ile Thr
 70                  75                  80                  85 atc ctg aag aca aag gac cta tca cct gag cac aac tac ctc atg ggg      344
Ile Leu Lys Thr Lys Asp Leu Ser Pro Glu His Asn Tyr Leu Met Gly
             90                  95                 100 gtt cac ccc cat ggc ctc ctg acc ttt ggc gcc ttc tgc aac ttc tgc      392
Val His Pro His Gly Leu Leu Thr Phe Gly Ala Phe Cys Asn Phe Cys
        105                 110                 115 act gag gcc aca ggc ttc tcg aag acc ttc cca ggc atc act cct cac      440
Thr Glu Ala Thr Gly Phe Ser Lys Thr Phe Pro Gly Ile Thr Pro His
        120                 125                 130 ttg gcc aca ctg tcc tgg ttc ttc aag atc ccc ttt gtt agg gag tac      488
Leu Ala Thr Leu Ser Trp Phe Phe Lys Ile Pro Phe Val Arg Glu Tyr
135                 140                 145 ctc atg gcc aaa ggt gtg tgc tct gtg agc cag cca gcc atc aac tat      536
Leu Met Ala Lys Gly Val Cys Ser Val Ser Gln Pro Ala Ile Asn Tyr
150                 155                 160                 165 ctg ctg agc cat ggc act ggc aac ctc gtg ggc att gta gtg gga ggt      584
Leu Leu Ser His Gly Thr Gly Asn Leu Val Gly Ile Val Val Gly Gly
                170                 175                 180 gtg ggt gag gcc ctg caa agt gtg ccc aag acc acc acc ctc atc ctc      632
Val Gly Glu Ala Leu Gln Ser Val Pro Lys Thr Thr Thr Leu Ile Leu
            185                 190                 195 cag aag cgc aag ggg ttc gtg cgc aca gcc ctc cag cat ggg gct cat      680
Gln Lys Arg Lys Gly Phe Val Arg Thr Ala Leu Gln His Gly Ala His
        200                 205                 210 ctg gtc ccc acc ttc act ttt ggg gaa act gag gtg tat gat cag gtg      728
Leu Val Pro Thr Phe Thr Phe Gly Glu Thr Glu Val Tyr Asp Gln Val
        215                 220                 225
```

-continued

```
ctg ttc cat aag gat agc agg atg tac aag ttc cag agc tgc ttc cgc     776
Leu Phe His Lys Asp Ser Arg Met Tyr Lys Phe Gln Ser Cys Phe Arg
230                 235                 240                 245 cgt atc ttt ggt ttc tac tgt tgt gtc ttc tat gga caa agc ttc tgt     824
Arg Ile Phe Gly Phe Tyr Cys Cys Val Phe Tyr Gly Gln Ser Phe Cys
                250                 255                 260 caa ggc tcc act ggg ctc ctg cca tac tcc agg cct att gtc act gtg     872
Gln Gly Ser Thr Gly Leu Leu Pro Tyr Ser Arg Pro Ile Val Thr Val
265                 270                 275 gtt ggg gag cct ctg cca ctg ccc caa att gaa aag cca agc cag gag     920
Val Gly Glu Pro Leu Pro Leu Pro Gln Ile Glu Lys Pro Ser Gln Glu
        280                 285                 290 atg gtg gac aaa tac cat gca ctt tat atg gat gct ctg gac aaa ctg     968
Met Val Asp Lys Tyr His Ala Leu Tyr Met Asp Ala Leu Asp Lys Leu
295                 300                 305 ttc gac cag cat aag acc cac tat ggc tgc tca gag acc caa aag ctg    1016
Phe Asp Gln His Lys Thr His Tyr Gly Cys Ser Glu Thr Gln Lys Leu
310                 315                 320                 325 ttt ttc ctg tga atgaaggtac tgcatgccca ggagcacagg agtgcctgcc        1068
Phe Phe Leu  * tttgaagaag aagaatcatc tggcataacc aaagacaggc aggagatgga gggaggtata  1128
tgtggtaggg gagggcatga ggaattcctt ctttgccttc ttgccacagg gtccttacag  1188
gaaattcttt ctgaagagct gcacacagtc attcctcaaa ggagggcatt ctagtgcccc  1248
tcatgctggg gcctgatgcc tgtcatcatt g                                 1279
```

<210> SEQ ID NO 14
<211> LENGTH: 328
<212> TYPE: PRT
<213> ORGANISM: human

<400> SEQUENCE: 14

Met Ala His Ser Lys Gln Pro Ser His Phe Gln Ser Leu Met Leu Leu
1               5                   10                  15

Gln Trp Pro Leu Ser Tyr Leu Ala Ile Phe Trp Ile Leu Gln Pro Leu
            20                  25                  30

Phe Val Tyr Leu Leu Phe Thr Ser Leu Trp Pro Leu Pro Val Leu Tyr
        35                  40                  45

Phe Ala Trp Leu Phe Leu Asp Trp Lys Thr Pro Glu Arg Gly Gly Arg
    50                  55                  60

Arg Ser Ala Trp Val Arg Asn Trp Cys Val Trp Thr His Ile Arg Asp
65                  70                  75                  80

Tyr Phe Pro Ile Thr Ile Leu Lys Thr Lys Asp Leu Ser Pro Glu His
                85                  90                  95

Asn Tyr Leu Met Gly Val His Pro His Gly Leu Leu Thr Phe Gly Ala
            100                 105                 110

Phe Cys Asn Phe Cys Thr Glu Ala Thr Gly Phe Ser Lys Thr Phe Pro
        115                 120                 125

Gly Ile Thr Pro His Leu Ala Thr Leu Ser Trp Phe Phe Lys Ile Pro
    130                 135                 140

Phe Val Arg Glu Tyr Leu Met Ala Lys Gly Val Cys Ser Val Ser Gln
145                 150                 155                 160

Pro Ala Ile Asn Tyr Leu Leu Ser His Gly Thr Gly Asn Leu Val Gly
                165                 170                 175

Ile Val Val Gly Gly Val Gly Glu Ala Leu Gln Ser Val Pro Lys Thr
            180                 185                 190

```
Thr Thr Leu Ile Leu Gln Lys Arg Lys Gly Phe Val Arg Thr Ala Leu
        195                 200                 205

Gln His Gly Ala His Leu Val Pro Thr Phe Thr Phe Gly Glu Thr Glu
    210                 215                 220

Val Tyr Asp Gln Val Leu Phe His Lys Asp Ser Arg Met Tyr Lys Phe
225                 230                 235                 240

Gln Ser Cys Phe Arg Arg Ile Phe Gly Phe Tyr Cys Cys Val Phe Tyr
                245                 250                 255

Gly Gln Ser Phe Cys Gln Gly Ser Thr Gly Leu Leu Pro Tyr Ser Arg
            260                 265                 270

Pro Ile Val Thr Val Gly Glu Pro Leu Pro Leu Pro Gln Ile Glu
            275                 280                 285

Lys Pro Ser Gln Glu Met Val Asp Lys Tyr His Ala Leu Tyr Met Asp
    290                 295                 300

Ala Leu Asp Lys Leu Phe Asp Gln His Lys Thr His Tyr Gly Cys Ser
305                 310                 315                 320

Glu Thr Gln Lys Leu Phe Phe Leu
                325

<210> SEQ ID NO 15
<211> LENGTH: 1255
<212> TYPE: DNA
<213> ORGANISM: mus musculus
<220> FEATURE:
<221> NAME/KEY: CDS
<222> LOCATION: (27)...(1151)

<400> SEQUENCE: 15
ttacctccct cagggtcctg ggcatc atg tct tgc tct atg aag act gaa cac      53
                              Met Ser Cys Ser Met Lys Thr Glu His
                                1               5 tta cag agt ctg agc ctt ctg cag tgg ccc ttg agc tac gtt gcc atg     101
Leu Gln Ser Leu Ser Leu Leu Gln Trp Pro Leu Ser Tyr Val Ala Met
 10                  15                  20                  25 ttt tgg att gtg cag cca ttg tta att tgc cta ttg ttc aca ccc ttg     149
Phe Trp Ile Val Gln Pro Leu Leu Ile Cys Leu Leu Phe Thr Pro Leu
                 30                  35                  40 tgg ccg cta cca aca gtt tac ttt gtc tgg tta ctt ctc gac tgg aag     197
Trp Pro Leu Pro Thr Val Tyr Phe Val Trp Leu Leu Leu Asp Trp Lys
             45                  50                  55 act cca gat aaa ggt ggc agg cgt tca gac tgg gta cgg aac tgg aat     245
Thr Pro Asp Lys Gly Gly Arg Arg Ser Asp Trp Val Arg Asn Trp Asn
         60                  65                  70 gtc tgg aac cac atc agg gac tat ttc ccc att aca atc ctg aag act     293
Val Trp Asn His Ile Arg Asp Tyr Phe Pro Ile Thr Ile Leu Lys Thr
     75                  80                  85 aag gac ctg tca cct tca gag aac tac atc atg ggg gtc cac ccc mat     341
Lys Asp Leu Ser Pro Ser Glu Asn Tyr Ile Met Gly Val His Pro Xaa
 90                  95                 100                 105 ggt ctc ctg acc ttc ggt gcc ttc tgc aac ttc tgc act gag gcc aca     389
Gly Leu Leu Thr Phe Gly Ala Phe Cys Asn Phe Cys Thr Glu Ala Thr
                110                 115                 120 ggc ttc tcg aag acc ttc cca ggc atc act cct cac ttg gcc aca ctg     437
Gly Phe Ser Lys Thr Phe Pro Gly Ile Thr Pro His Leu Ala Thr Leu
            125                 130                 135 tcc tgg ttc ttc aag atc ccc att att agg gac tac atc atg gcc aaa     485
Ser Trp Phe Phe Lys Ile Pro Ile Ile Arg Asp Tyr Ile Met Ala Lys
        140                 145                 150
```

|  |  |
|---|---|
| gga ttg tgt tct gtg agc cag gca tcc atc gac tac ctg ctg agc cat<br>Gly Leu Cys Ser Val Ser Gln Ala Ser Ile Asp Tyr Leu Leu Ser His<br>155                    160                    165 | 533 |
| ggc act gga aac ctc gtg ggc att gtc gtg gga gga gtg gga gag gcc<br>Gly Thr Gly Asn Leu Val Gly Ile Val Val Gly Gly Val Gly Glu Ala<br>170                  175                    180                    185 | 581 |
| cta cag agt gtg cct aac acc acc acc ctc ctc ctc aag aaa cgc aaa<br>Leu Gln Ser Val Pro Asn Thr Thr Thr Leu Leu Leu Lys Lys Arg Lys<br>                    190                    195                    200 | 629 |
| ggg ttt gtg cgc aca gcc ctc caa cat ggg gct cat ctg gtc cct acc<br>Gly Phe Val Arg Thr Ala Leu Gln His Gly Ala His Leu Val Pro Thr<br>                205                    210                    215 | 677 |
| ttc acg ttc gga gaa aca gag gta tat gac cag gta ctg ttt cat gag<br>Phe Thr Phe Gly Glu Thr Glu Val Tyr Asp Gln Val Leu Phe His Glu<br>            220                    225                    230 | 725 |
| gat agc cgg atg ttc aag ttc caa agc ctc ttt cgc cgg atc ttt ggt<br>Asp Ser Arg Met Phe Lys Phe Gln Ser Leu Phe Arg Arg Ile Phe Gly<br>235                    240                    245 | 773 |
| ttc tat tgc tgt gtc ttc tat gga caa ggt ttc cat caa gac tgc aag<br>Phe Tyr Cys Cys Val Phe Tyr Gly Gln Gly Phe His Gln Asp Cys Lys<br>250                    255                    260                    265 | 821 |
| gga ctc cta cca tac cac aaa ccc atc atc act gta gtt ggg gaa gct<br>Gly Leu Leu Pro Tyr His Lys Pro Ile Ile Thr Val Val Gly Glu Ala<br>                    270                    275                    280 | 869 |
| ttg cca ctg ccc cag gtt aaa aac cca agc cca gag ata gtg gac aaa<br>Leu Pro Leu Pro Gln Val Lys Asn Pro Ser Pro Glu Ile Val Asp Lys<br>285                    290                    295 | 917 |
| tac cat gca ctc tac atg gac gcc ctg tac aag ctg ttt gag cag cac<br>Tyr His Ala Leu Tyr Met Asp Ala Leu Tyr Lys Leu Phe Glu Gln His<br>300                    305                    310 | 965 |
| atc ccg tta gga aaa aca gcc tgg gac cac agc ttg ggc atc tcc cag<br>Ile Pro Leu Gly Lys Thr Ala Trp Asp His Ser Leu Gly Ile Ser Gln<br>315                    320                    325 | 1013 |
| agc aaa atc ccg gtg gag gac ccg atg agt ctg ctc tac aac atg aac<br>Ser Lys Ile Pro Val Glu Asp Pro Met Ser Leu Leu Tyr Asn Met Asn<br>330                    335                    340                    345 | 1061 |
| gac tgc tac tcc aag ctc aag gaa ctg atg ccc agc att ccc cag aac<br>Asp Cys Tyr Ser Lys Leu Lys Glu Leu Met Pro Ser Ile Pro Gln Asn<br>                    350                    355                    360 | 1109 |
| aag aag gca gcc cta caa ttt tgg ctg ctc atc tgg ttg tag<br>Lys Lys Ala Ala Leu Gln Phe Trp Leu Leu Ile Trp Leu *<br>365                    370 | 1151 |
| caaagttgaa aacttctgaa aaggggatcc cacctacagg aactgtaata aatgcctctt | 1211 |
| cattcattgc tccgtggact cctcatccga atcctgtcaa atag | 1255 |

```
<210> SEQ ID NO 16
<211> LENGTH: 374
<212> TYPE: PRT
<213> ORGANISM: mus musculus
<220> FEATURE:
<221> NAME/KEY: VARIANT
<222> LOCATION: (1)...(470)
<223> OTHER INFORMATION: Xaa = Any Amino Acid

<400> SEQUENCE: 16
```

Met Ser Cys Ser Met Lys Thr Glu His Leu Gln Ser Leu Ser Leu Leu
 1               5                  10                  15

Gln Trp Pro Leu Ser Tyr Val Ala Met Phe Trp Ile Val Gln Pro Leu
            20                  25                  30

```
Leu Ile Cys Leu Leu Phe Thr Pro Leu Trp Leu Pro Thr Val Tyr
        35                  40                  45

Phe Val Trp Leu Leu Leu Asp Trp Lys Thr Pro Asp Lys Gly Gly Arg
 50                  55                  60

Arg Ser Asp Trp Val Arg Asn Trp Asn Val Trp Asn His Ile Arg Asp
 65                  70                  75                  80

Tyr Phe Pro Ile Thr Ile Leu Lys Thr Lys Asp Leu Ser Pro Ser Glu
                 85                  90                  95

Asn Tyr Ile Met Gly Val His Pro Xaa Gly Leu Leu Thr Phe Gly Ala
                100                 105                 110

Phe Cys Asn Phe Cys Thr Glu Ala Thr Gly Phe Ser Lys Thr Phe Pro
                115                 120                 125

Gly Ile Thr Pro His Leu Ala Thr Leu Ser Trp Phe Phe Lys Ile Pro
                130                 135                 140

Ile Ile Arg Asp Tyr Ile Met Ala Lys Gly Leu Cys Ser Val Ser Gln
145                 150                 155                 160

Ala Ser Ile Asp Tyr Leu Leu Ser His Gly Thr Gly Asn Leu Val Gly
                165                 170                 175

Ile Val Val Gly Gly Val Gly Glu Ala Leu Gln Ser Val Pro Asn Thr
                180                 185                 190

Thr Thr Leu Leu Leu Lys Lys Arg Lys Gly Phe Val Arg Thr Ala Leu
                195                 200                 205

Gln His Gly Ala His Leu Val Pro Thr Phe Thr Phe Gly Glu Thr Glu
                210                 215                 220

Val Tyr Asp Gln Val Leu Phe His Glu Asp Ser Arg Met Phe Lys Phe
225                 230                 235                 240

Gln Ser Leu Phe Arg Arg Ile Phe Gly Phe Tyr Cys Cys Val Phe Tyr
                245                 250                 255

Gly Gln Gly Phe His Gln Asp Cys Lys Gly Leu Leu Pro Tyr His Lys
                260                 265                 270

Pro Ile Ile Thr Val Val Gly Glu Ala Leu Pro Leu Pro Gln Val Lys
                275                 280                 285

Asn Pro Ser Pro Glu Ile Val Asp Lys Tyr His Ala Leu Tyr Met Asp
                290                 295                 300

Ala Leu Tyr Lys Leu Phe Glu Gln His Ile Pro Leu Gly Lys Thr Ala
305                 310                 315                 320

Trp Asp His Ser Leu Gly Ile Ser Gln Ser Lys Ile Pro Val Glu Asp
                325                 330                 335

Pro Met Ser Leu Leu Tyr Asn Met Asn Asp Cys Tyr Ser Lys Leu Lys
                340                 345                 350

Glu Leu Met Pro Ser Ile Pro Gln Asn Lys Lys Ala Ala Leu Gln Phe
                355                 360                 365

Trp Leu Leu Ile Trp Leu
                370

<210> SEQ ID NO 17
<211> LENGTH: 1420
<212> TYPE: DNA
<213> ORGANISM: human
<220> FEATURE:
<221> NAME/KEY: CDS
<222> LOCATION: (1)...(1002)
```

```
<400> SEQUENCE: 17 atg ctc ttg ccc tct aag aag gac ctc aag act gcc ctg gat gtc ttt       48
Met Leu Leu Pro Ser Lys Lys Asp Leu Lys Thr Ala Leu Asp Val Phe
 1               5                  10                  15 gct gtt ttc cag tgg tcc ttc agt gcc ttg ctt atc aca acc act gtg       96
Ala Val Phe Gln Trp Ser Phe Ser Ala Leu Leu Ile Thr Thr Thr Val
             20                  25                  30 att gct gtc aac ctc tac ctg gtg gtg ttc aca cca tac tgg cct gtc      144
Ile Ala Val Asn Leu Tyr Leu Val Val Phe Thr Pro Tyr Trp Pro Val
         35                  40                  45 act gtg ctt att ctt acc tgg ctg gct ttt gac tgg aag acc cct cag      192
Thr Val Leu Ile Leu Thr Trp Leu Ala Phe Asp Trp Lys Thr Pro Gln
     50                  55                  60 cga ggc ggc cgc cgg ttt acc tgt gtg agg cac tgg cgc ctg tgg aaa      240
Arg Gly Gly Arg Arg Phe Thr Cys Val Arg His Trp Arg Leu Trp Lys
 65                  70                  75                  80 cac tac agc gat tat ttc cct ctc aag ctt ctg aag act cat gac atc      288
His Tyr Ser Asp Tyr Phe Pro Leu Lys Leu Leu Lys Thr His Asp Ile
                 85                  90                  95 tgc ccc agc cgc aac tac atc ctc gtc tgc cac cct cat ggg ctc ttt      336
Cys Pro Ser Arg Asn Tyr Ile Leu Val Cys His Pro His Gly Leu Phe
            100                 105                 110 gcc cat gga tgg ttt ggc cac ttt gcc aca gag gcc tca ggc ttc tcc      384
Ala His Gly Trp Phe Gly His Phe Ala Thr Glu Ala Ser Gly Phe Ser
        115                 120                 125 aag ata ttt cct ggc atc acc cct tac ata ctc aca ctg gga gcc ttt      432
Lys Ile Phe Pro Gly Ile Thr Pro Tyr Ile Leu Thr Leu Gly Ala Phe
    130                 135                 140 ttc tgg atg cct ttc ctc aga gaa tat gta atg tct aca ggg gcc tgc      480
Phe Trp Met Pro Phe Leu Arg Glu Tyr Val Met Ser Thr Gly Ala Cys
145                 150                 155                 160 tct gtg agt cga tcc tcc att gac ttt ctg ctg act cat aaa ggc aca      528
Ser Val Ser Arg Ser Ser Ile Asp Phe Leu Leu Thr His Lys Gly Thr
                165                 170                 175 ggc aac atg gtc att gtg gtg att ggt gga ctg gct gag tgc aga tac      576
Gly Asn Met Val Ile Val Val Ile Gly Gly Leu Ala Glu Cys Arg Tyr
            180                 185                 190 agc ctg cca ggt tct tct acc ctg gtg ttg aag aac cgg tct ggc ttt      624
Ser Leu Pro Gly Ser Ser Thr Leu Val Leu Lys Asn Arg Ser Gly Phe
        195                 200                 205 gtg cgc atg gcc ctt cag cat ggg gtg cct cta ata cct gcc tat gcc      672
Val Arg Met Ala Leu Gln His Gly Val Pro Leu Ile Pro Ala Tyr Ala
    210                 215                 220 ttt ggg gag acg gac ctc tat gat cag cac att ttc act cct ggt ggc      720
Phe Gly Glu Thr Asp Leu Tyr Asp Gln His Ile Phe Thr Pro Gly Gly
225                 230                 235                 240 ttt gtc aac cgc ttc cag aag tgg ttc cag agc atg gta cac atc tac      768
Phe Val Asn Arg Phe Gln Lys Trp Phe Gln Ser Met Val His Ile Tyr
                245                 250                 255 cct tgt gct ttc tat gga cgt ggc ttc acc aag aac tcc tgg ggc ctt      816
Pro Cys Ala Phe Tyr Gly Arg Gly Phe Thr Lys Asn Ser Trp Gly Leu
            260                 265                 270 ctg ccc tat agt cgg cct gta acc acc atc gtc ggg gag cct cta cca      864
Leu Pro Tyr Ser Arg Pro Val Thr Thr Ile Val Gly Glu Pro Leu Pro
        275                 280                 285 atg ccc aag att gag aat cca agc cag gag atc gtg gct aaa tat cac      912
Met Pro Lys Ile Glu Asn Pro Ser Gln Glu Ile Val Ala Lys Tyr His
    290                 295                 300
```

```
aca ctc tat att gat gcc cta cgt aaa ctg ttt gac cag cat aag acc    960
Thr Leu Tyr Ile Asp Ala Leu Arg Lys Leu Phe Asp Gln His Lys Thr
305                 310                 315                 320 aag ttt ggt atc tca gag acc cag gag ctg gag ata att tga           1002
Lys Phe Gly Ile Ser Glu Thr Gln Glu Leu Glu Ile Ile *
                325                 330 cagacatccc cagtaagcct wcamcctggc tggaagctct tttctgccct tctttgcag   1062 ctactggtga gatagtccca agaaacaggg aagagcctag gggagaggtg ccctgacggc  1122
acttggtggc agcattgagg aaaaaatgga gaacattaaa agcccatctt ctgataactg  1182
cgtgtgcacc aactactctg ttttgaaggc tctgagatgc atgtctactc cttctctaac  1242
tgtcaaacag acccatctcc cggcattgag cccatcttta ggcattgagt cctgattccc  1302
tacaggagta ggatgggcct tgaagcaagt gagatgaagt tcagcccaca acttcaagtc  1362
atgtactttg gggcatcagc tcacctctga gcccttctt cttctatacg attgcacc    1420
```

<210> SEQ ID NO 18
<211> LENGTH: 333
<212> TYPE: PRT
<213> ORGANISM: human

<400> SEQUENCE: 18

```
Met Leu Leu Pro Ser Lys Lys Asp Leu Lys Thr Ala Leu Asp Val Phe
1               5                   10                  15

Ala Val Phe Gln Trp Ser Phe Ser Ala Leu Leu Ile Thr Thr Thr Val
                20                  25                  30

Ile Ala Val Asn Leu Tyr Leu Val Phe Thr Pro Tyr Trp Pro Val
            35                  40                  45

Thr Val Leu Ile Leu Thr Trp Leu Ala Phe Asp Trp Lys Thr Pro Gln
50                  55                  60

Arg Gly Gly Arg Arg Phe Thr Cys Val Arg His Trp Arg Leu Trp Lys
65                  70                  75                  80

His Tyr Ser Asp Tyr Phe Pro Leu Lys Leu Leu Lys Thr His Asp Ile
                85                  90                  95

Cys Pro Ser Arg Asn Tyr Ile Leu Val Cys His Pro His Gly Leu Phe
            100                 105                 110

Ala His Gly Trp Phe Gly His Phe Ala Thr Glu Ala Ser Gly Phe Ser
        115                 120                 125

Lys Ile Phe Pro Gly Ile Thr Pro Tyr Ile Leu Thr Leu Gly Ala Phe
        130                 135                 140

Phe Trp Met Pro Phe Leu Arg Glu Tyr Val Met Ser Thr Gly Ala Cys
145                 150                 155                 160

Ser Val Ser Arg Ser Ile Asp Phe Leu Leu Thr His Lys Gly Thr
                165                 170                 175

Gly Asn Met Val Ile Val Ile Gly Gly Leu Ala Glu Cys Arg Tyr
            180                 185                 190

Ser Leu Pro Gly Ser Ser Thr Leu Val Leu Lys Asn Arg Ser Gly Phe
        195                 200                 205

Val Arg Met Ala Leu Gln His Gly Val Pro Leu Ile Pro Ala Tyr Ala
    210                 215                 220

Phe Gly Glu Thr Asp Leu Tyr Asp Gln His Ile Phe Thr Pro Gly Gly
225                 230                 235                 240

Phe Val Asn Arg Phe Gln Lys Trp Phe Gln Ser Met Val His Ile Tyr
                245                 250                 255
```

```
Pro Cys Ala Phe Tyr Gly Arg Gly Phe Thr Lys Asn Ser Trp Gly Leu
        260                 265                 270

Leu Pro Tyr Ser Arg Pro Val Thr Thr Ile Val Gly Glu Pro Leu Pro
        275                 280                 285

Met Pro Lys Ile Glu Asn Pro Ser Gln Glu Ile Val Ala Lys Tyr His
        290                 295                 300

Thr Leu Tyr Ile Asp Ala Leu Arg Lys Leu Phe Asp Gln His Lys Thr
305                 310                 315                 320

Lys Phe Gly Ile Ser Glu Thr Gln Glu Leu Glu Ile Ile
                325                 330

<210> SEQ ID NO 19
<211> LENGTH: 1716
<212> TYPE: DNA
<213> ORGANISM: human
<220> FEATURE:
<221> NAME/KEY: CDS
<222> LOCATION: (101)...(1114)

<400> SEQUENCE: 19
cacagtaaga gattatagca aagcatctat aatcaactca gcttaagaag ttttgacctt      60
ctggttaggc ttcttgccac aacagaacag caccataacc atg gct ttc ttc tcc     115
                                              Met Ala Phe Phe Ser
                                               1               5 cga ctg aat ctc cag gag ggc ctc caa acc ttc ttt gtt ttg caa tgg     163
Arg Leu Asn Leu Gln Glu Gly Leu Gln Thr Phe Phe Val Leu Gln Trp
             10                  15                  20 atc cca gtc tat ata ttt tta gga gct att ccc att ctc ctt ata ccc     211
Ile Pro Val Tyr Ile Phe Leu Gly Ala Ile Pro Ile Leu Leu Ile Pro
                 25                  30                  35 tac ttt ctg tta ttc agt aag ttc tgg ccc ttg gct gtg ctc tcc tta     259
Tyr Phe Leu Leu Phe Ser Lys Phe Trp Pro Leu Ala Val Leu Ser Leu
             40                  45                  50 gcc tgg ctc acc tat gat tgg aac acc cac agt caa ggt ggc agg cgt     307
Ala Trp Leu Thr Tyr Asp Trp Asn Thr His Ser Gln Gly Gly Arg Arg
 55                  60                  65 tca gct tgg gta cga aac tgg acc cta tgg aag tat ttc cga aat tac     355
Ser Ala Trp Val Arg Asn Trp Thr Leu Trp Lys Tyr Phe Arg Asn Tyr
 70                  75                  80                  85 ttc cca gta aag ctg gtg aag act cat gat ctt tct ccc aaa cac aac     403
Phe Pro Val Lys Leu Val Lys Thr His Asp Leu Ser Pro Lys His Asn
                 90                  95                 100 tac atc att gcc aat cac ccc cat ggc att ctc tct ttt ggt gtc ttc     451
Tyr Ile Ile Ala Asn His Pro His Gly Ile Leu Ser Phe Gly Val Phe
            105                 110                 115 atc aac ttt gcc act gag gcc act ggc att gct cgg att ttc cca tcc     499
Ile Asn Phe Ala Thr Glu Ala Thr Gly Ile Ala Arg Ile Phe Pro Ser
        120                 125                 130 atc act ccc ttt gta ggg acc tta gaa agg ata ttt tgg atc cca att     547
Ile Thr Pro Phe Val Gly Thr Leu Glu Arg Ile Phe Trp Ile Pro Ile
    135                 140                 145 gtg cga gaa tat gtg atg tca atg ggt gtg tgc cct gtg agc agc tca     595
Val Arg Glu Tyr Val Met Ser Met Gly Val Cys Pro Val Ser Ser Ser
150                 155                 160                 165 gcc ttg aag tac ttg ctg acc cag aaa ggc tca ggc aat gcc gtg gtt     643
Ala Leu Lys Tyr Leu Leu Thr Gln Lys Gly Ser Gly Asn Ala Val Val
                170                 175                 180 att gtg gtg ggt gga gct gct gaa gct ctc ttg tgc cga cca gga gcc     691
Ile Val Val Gly Gly Ala Ala Glu Ala Leu Leu Cys Arg Pro Gly Ala
            185                 190                 195
```

-continued

| | | |
|---|---|---|
| tcc act ctc ttc ctc aag cag cgt aaa ggt ttt gtg aag atg gca ctg<br>Ser Thr Leu Phe Leu Lys Gln Arg Lys Gly Phe Val Lys Met Ala Leu<br>200 205 210 | 739 | |
| caa aca ggg gca tac ctt gtc cct tca tat tcc ttt ggt gag aac gaa<br>Gln Thr Gly Ala Tyr Leu Val Pro Ser Tyr Ser Phe Gly Glu Asn Glu<br>215 220 225 | 787 | |
| gtt ttc aat cag gag acc ttc cct gag ggc acg tgg tta agg ttg ttc<br>Val Phe Asn Gln Glu Thr Phe Pro Glu Gly Thr Trp Leu Arg Leu Phe<br>230 235 240 245 | 835 | |
| caa aaa acc ttc cag gac aca ttc aaa aaa atc ctg gga cta aat ttc<br>Gln Lys Thr Phe Gln Asp Thr Phe Lys Lys Ile Leu Gly Leu Asn Phe<br>250 255 260 | 883 | |
| tgt acc ttc cat ggc cgg ggc ttc act cgc gga tcc tgg ggc ttc ctg<br>Cys Thr Phe His Gly Arg Gly Phe Thr Arg Gly Ser Trp Gly Phe Leu<br>265 270 275 | 931 | |
| cct ttc aat cgg ccc att acc act gtt gtt ggg gaa ccc ctt cca att<br>Pro Phe Asn Arg Pro Ile Thr Thr Val Val Gly Glu Pro Leu Pro Ile<br>280 285 290 | 979 | |
| ccc agg att aag agg cca aac cag aag aca gta gac aag tat cac gca<br>Pro Arg Ile Lys Arg Pro Asn Gln Lys Thr Val Asp Lys Tyr His Ala<br>295 300 305 | 1027 | |
| ctc tac atc agt gcc ctg cgc aag ctc ttt gac caa cac aaa gtt gaa<br>Leu Tyr Ile Ser Ala Leu Arg Lys Leu Phe Asp Gln His Lys Val Glu<br>310 315 320 325 | 1075 | |
| tat ggc ctc cct gag acc caa gag ctg aca att aca taa caggagccac<br>Tyr Gly Leu Pro Glu Thr Gln Glu Leu Thr Ile Thr *<br>330 335 | 1124 | |
| attccccatt gatcaacccc caaagccatg agggatccaa gtagagccac agaaaaagaa | 1184 | |
| gaattccagg agagggaaag atcgtaagga tgagagagga gaccatccaa gccagaaatt | 1244 | |
| atttaataaa tcagagttct agcaatagag tcctctccca agtggctgag gcaggcttag | 1304 | |
| gggaaagaac cagaggggca ggggaggact ggggagggct ggctagccag aggagttggc | 1364 | |
| tgtatcaccc ctggttattt tagggcaaca acccagttgg ggagtcttat gaatcattcc | 1424 | |
| agccaactct ctgatcacaa agaatactgt gcccctttct cctaaacctt agttcaccat | 1484 | |
| cactacgtag gtttagactt agaagcttta tttggaacag ggatagtttg tttcctcttg | 1544 | |
| gtcctttcct tacaacttgg gaactgccac aaggtaaacc agggacctga actgtagctg | 1604 | |
| cctggtccaa gcagacagga ttccgtcagt tgtgatagag ttctagattg gcaatgcagt | 1664 | |
| tacattgttt cttctttgaa aataaagttc tagacatata aaaaaaaaaa aa | 1716 | |

<210> SEQ ID NO 20
<211> LENGTH: 337
<212> TYPE: PRT
<213> ORGANISM: human

<400> SEQUENCE: 20

Met Ala Phe Phe Ser Arg Leu Asn Leu Gln Glu Gly Leu Gln Thr Phe
1               5                   10                  15

Phe Val Leu Gln Trp Ile Pro Val Tyr Ile Phe Leu Gly Ala Ile Pro
            20                  25                  30

Ile Leu Leu Ile Pro Tyr Phe Leu Phe Ser Lys Phe Trp Pro Leu
        35                  40                  45

Ala Val Leu Ser Leu Ala Trp Leu Thr Tyr Asp Trp Asn Thr His Ser
    50                  55                  60

Gln Gly Gly Arg Arg Ser Ala Trp Val Arg Asn Trp Thr Leu Trp Lys
65                  70                  75                  80

```
Tyr Phe Arg Asn Tyr Phe Pro Val Lys Leu Val Lys Thr His Asp Leu
                85                  90                  95

Ser Pro Lys His Asn Tyr Ile Ile Ala Asn His Pro His Gly Ile Leu
            100                 105                 110

Ser Phe Gly Val Phe Ile Asn Phe Ala Thr Glu Ala Thr Gly Ile Ala
            115                 120                 125

Arg Ile Phe Pro Ser Ile Thr Pro Phe Val Gly Thr Leu Glu Arg Ile
        130                 135                 140

Phe Trp Ile Pro Ile Val Arg Glu Tyr Val Met Ser Met Gly Val Cys
145                 150                 155                 160

Pro Val Ser Ser Ser Ala Leu Lys Tyr Leu Leu Thr Gln Lys Gly Ser
                165                 170                 175

Gly Asn Ala Val Ile Val Val Gly Gly Ala Ala Glu Ala Leu Leu
            180                 185                 190

Cys Arg Pro Gly Ala Ser Thr Leu Phe Leu Lys Gln Arg Lys Gly Phe
            195                 200                 205

Val Lys Met Ala Leu Gln Thr Gly Ala Tyr Leu Val Pro Ser Tyr Ser
        210                 215                 220

Phe Gly Glu Asn Glu Val Phe Asn Gln Glu Thr Phe Pro Glu Gly Thr
225                 230                 235                 240

Trp Leu Arg Leu Phe Gln Lys Thr Phe Gln Asp Thr Phe Lys Lys Ile
                245                 250                 255

Leu Gly Leu Asn Phe Cys Thr Phe His Gly Arg Gly Phe Thr Arg Gly
            260                 265                 270

Ser Trp Gly Phe Leu Pro Phe Asn Arg Pro Ile Thr Thr Val Val Gly
            275                 280                 285

Glu Pro Leu Pro Ile Pro Arg Ile Lys Arg Pro Asn Gln Lys Thr Val
        290                 295                 300

Asp Lys Tyr His Ala Leu Tyr Ile Ser Ala Leu Arg Lys Leu Phe Asp
305                 310                 315                 320

Gln His Lys Val Glu Tyr Gly Leu Pro Glu Thr Gln Glu Leu Thr Ile
                325                 330                 335

Thr

<210> SEQ ID NO 21
<211> LENGTH: 1093
<212> TYPE: DNA
<213> ORGANISM: human
<220> FEATURE:
<221> NAME/KEY: CDS
<222> LOCATION: (49)...(1053)

<400> SEQUENCE: 21
cgtgggtgca ggctgcagtg gctggcgccg tcctcgcccg gccaggcc atg aag gta        57
                                                    Met Lys Val
                                                      1 gag ttt gca ccg ctc aac atc cag ctg gcg cgg cgg ctg cag acg gtg       105
Glu Phe Ala Pro Leu Asn Ile Gln Leu Ala Arg Arg Leu Gln Thr Val
  5                  10                  15 gcc gtg ctg cag tgg gtc ctt tct ttt ctt aca ggg ccg atg tcc att       153
Ala Val Leu Gln Trp Val Leu Ser Phe Leu Thr Gly Pro Met Ser Ile
 20                  25                  30                  35 gga atc act gtg atg ctg atc ata cac aac tat ttg ttc ctt tac atc       201
Gly Ile Thr Val Met Leu Ile Ile His Asn Tyr Leu Phe Leu Tyr Ile
                 40                  45                  50
```

```
cct tat ttg atg tgg ctt tac ttt gac tgg cat acc cca gag cga gga      249
Pro Tyr Leu Met Trp Leu Tyr Phe Asp Trp His Thr Pro Glu Arg Gly
            55                  60                  65 ggc agg aga tcc agc tgg atc aaa aat tgg act ctt tgg aaa cac ttt      297
Gly Arg Arg Ser Ser Trp Ile Lys Asn Trp Thr Leu Trp Lys His Phe
        70                  75                  80 aag gac tat ttt cca att cat ctt atc aaa act caa gat ttg gat cca      345
Lys Asp Tyr Phe Pro Ile His Leu Ile Lys Thr Gln Asp Leu Asp Pro
    85                  90                  95 agt cac aac tat ata ttt ggg ttt cac ccc cat gga ata atg gca gtt      393
Ser His Asn Tyr Ile Phe Gly Phe His Pro His Gly Ile Met Ala Val
100                 105                 110                 115 gga gcc ttt ggg aat ttt tct gta aat tat tct gac ttc aag gac ctg      441
Gly Ala Phe Gly Asn Phe Ser Val Asn Tyr Ser Asp Phe Lys Asp Leu
                120                 125                 130 ttt cct ggc ttt act tca tat ctt cac gtg ctg cca ctt tgg ttc tgg      489
Phe Pro Gly Phe Thr Ser Tyr Leu His Val Leu Pro Leu Trp Phe Trp
            135                 140                 145 tgt cct gtc ttt cga gaa tat gtg atg agt gtt ggg ctg gtt tca gtt      537
Cys Pro Val Phe Arg Glu Tyr Val Met Ser Val Gly Leu Val Ser Val
        150                 155                 160 tcc aag aaa agt gtg tcc tac atg gta agc aag gag gga ggt gga aac      585
Ser Lys Lys Ser Val Ser Tyr Met Val Ser Lys Glu Gly Gly Gly Asn
    165                 170                 175 atc tct gtc att gtc ctt ggg ggt gca aaa gaa tca ctg gat gct cat      633
Ile Ser Val Ile Val Leu Gly Gly Ala Lys Glu Ser Leu Asp Ala His
180                 185                 190                 195 cct gga aag ttc act ctg ttc atc cgc cag cgg aaa gga ttt gtt aaa      681
Pro Gly Lys Phe Thr Leu Phe Ile Arg Gln Arg Lys Gly Phe Val Lys
                200                 205                 210 att gct ttg acc cat ggc gcc tct ctg gtc cca gtg gtt tct ttt ggt      729
Ile Ala Leu Thr His Gly Ala Ser Leu Val Pro Val Val Ser Phe Gly
            215                 220                 225 gaa aat gaa ctg ttt aaa caa act gac aac cct gaa gga tca tgg att      777
Glu Asn Glu Leu Phe Lys Gln Thr Asp Asn Pro Glu Gly Ser Trp Ile
        230                 235                 240 aga act gtt cag aat aaa ctg cag aag atc atg ggg ttt gct ttg ccc      825
Arg Thr Val Gln Asn Lys Leu Gln Lys Ile Met Gly Phe Ala Leu Pro
    245                 250                 255 ctg ttt cat gcc agg gga gtt ttt cag tac aat ttt ggc cta atg acc      873
Leu Phe His Ala Arg Gly Val Phe Gln Tyr Asn Phe Gly Leu Met Thr
260                 265                 270                 275 tat agg aaa gcc atc cac act gtt gtt ggc cgc ccg atc cct gtt cgt      921
Tyr Arg Lys Ala Ile His Thr Val Val Gly Arg Pro Ile Pro Val Arg
                280                 285                 290 cag act ctg aac ccg acc cag gag cag att gag gag tta cat cag acc      969
Gln Thr Leu Asn Pro Thr Gln Glu Gln Ile Glu Glu Leu His Gln Thr
            295                 300                 305 tat atg gag gaa ctt agg aaa ttg ttt gag gaa cac aaa gga aag tat     1017
Tyr Met Glu Glu Leu Arg Lys Leu Phe Glu Glu His Lys Gly Lys Tyr
        310                 315                 320 ggc att cca gag cac gag act ctt gtt tta aaa tga cttgactata          1063
Gly Ile Pro Glu His Glu Thr Leu Val Leu Lys *
    325                 330 aaaaaaaatt aaaaaataaa aataaatgac                                    1093

<210> SEQ ID NO 22
<211> LENGTH: 334
<212> TYPE: PRT
<213> ORGANISM: human
```

<400> SEQUENCE: 22

```
Met Lys Val Glu Phe Ala Pro Leu Asn Ile Gln Leu Ala Arg Arg Leu
1               5                  10                  15

Gln Thr Val Ala Val Leu Gln Trp Val Leu Ser Phe Leu Thr Gly Pro
            20                  25                  30

Met Ser Ile Gly Ile Thr Val Met Leu Ile Ile His Asn Tyr Leu Phe
        35                  40                  45

Leu Tyr Ile Pro Tyr Leu Met Trp Leu Tyr Phe Asp Trp His Thr Pro
    50                  55                  60

Glu Arg Gly Gly Arg Ser Ser Trp Ile Lys Asn Trp Thr Leu Trp
65                  70                  75                  80

Lys His Phe Lys Asp Tyr Phe Pro Ile His Leu Ile Lys Thr Gln Asp
                85                  90                  95

Leu Asp Pro Ser His Asn Tyr Ile Phe Gly Phe His Pro His Gly Ile
            100                 105                 110

Met Ala Val Gly Ala Phe Gly Asn Phe Ser Val Asn Tyr Ser Asp Phe
        115                 120                 125

Lys Asp Leu Phe Pro Gly Phe Thr Ser Tyr Leu His Val Leu Pro Leu
    130                 135                 140

Trp Phe Trp Cys Pro Val Phe Arg Glu Tyr Val Met Ser Val Gly Leu
145                 150                 155                 160

Val Ser Val Ser Lys Lys Ser Val Ser Tyr Met Val Ser Lys Glu Gly
                165                 170                 175

Gly Gly Asn Ile Ser Val Ile Val Leu Gly Gly Ala Lys Glu Ser Leu
            180                 185                 190

Asp Ala His Pro Gly Lys Phe Thr Leu Phe Ile Arg Gln Arg Lys Gly
        195                 200                 205

Phe Val Lys Ile Ala Leu Thr His Gly Ala Ser Leu Val Pro Val Val
    210                 215                 220

Ser Phe Gly Glu Asn Glu Leu Phe Lys Gln Thr Asp Asn Pro Glu Gly
225                 230                 235                 240

Ser Trp Ile Arg Thr Val Gln Asn Lys Leu Gln Lys Ile Met Gly Phe
                245                 250                 255

Ala Leu Pro Leu Phe His Ala Arg Gly Val Phe Gln Tyr Asn Phe Gly
            260                 265                 270

Leu Met Thr Tyr Arg Lys Ala Ile His Thr Val Val Gly Arg Pro Ile
        275                 280                 285

Pro Val Arg Gln Thr Leu Asn Pro Thr Gln Glu Gln Ile Glu Glu Leu
    290                 295                 300

His Gln Thr Tyr Met Glu Glu Leu Arg Lys Leu Phe Glu Glu His Lys
305                 310                 315                 320

Gly Lys Tyr Gly Ile Pro Glu His Glu Thr Leu Val Leu Lys
                325                 330
```

<210> SEQ ID NO 23
<211> LENGTH: 1008
<212> TYPE: DNA
<213> ORGANISM: mus musculus
<220> FEATURE:
<221> NAME/KEY: CDS
<222> LOCATION: (1)...(1008)

<400> SEQUENCE: 23

```
atg atg gtc gag ttc gcg cca ctc aac acc ccg ctg gca cgg tgc cta    48
Met Met Val Glu Phe Ala Pro Leu Asn Thr Pro Leu Ala Arg Cys Leu
1               5                  10                  15
```

-continued

```
cag acc gct gcg gtg ctg cag tgg gtc ctg tcc ttc ctc ctg ctc gtg        96
Gln Thr Ala Ala Val Leu Gln Trp Val Leu Ser Phe Leu Leu Leu Val
             20                  25                  30 cag gtg tgc att gga att atg gtg atg ctg gtc ctg tac aac tat tgg       144
Gln Val Cys Ile Gly Ile Met Val Met Leu Val Leu Tyr Asn Tyr Trp
         35                  40                  45 ttc ctt tac atc cca tat ctg gtc tgg ttt tac tat gac tgg aga acc       192
Phe Leu Tyr Ile Pro Tyr Leu Val Trp Phe Tyr Tyr Asp Trp Arg Thr
     50                  55                  60 cca gag caa gga ggc aga aga tgg aac tgg gtc caa agc tgg cct gtg       240
Pro Glu Gln Gly Gly Arg Arg Trp Asn Trp Val Gln Ser Trp Pro Val
 65                  70                  75                  80 tgg aag tat ttt aag gag tat ttt cca atc tgt ctt gtc aaa acg cag       288
Trp Lys Tyr Phe Lys Glu Tyr Phe Pro Ile Cys Leu Val Lys Thr Gln
                 85                  90                  95 gat ttg gat ccg ggt cac aat tat ata ttt ggg ttt cac cct cat gga       336
Asp Leu Asp Pro Gly His Asn Tyr Ile Phe Gly Phe His Pro His Gly
            100                 105                 110 ata ttc gtg cct gga gcc ttt gga aat ttt tgt aca aaa tac tcg gac       384
Ile Phe Val Pro Gly Ala Phe Gly Asn Phe Cys Thr Lys Tyr Ser Asp
        115                 120                 125 ttc aag aag cta ttt cct ggc ttt aca tcg tat ctc cac gtg gcc aag       432
Phe Lys Lys Leu Phe Pro Gly Phe Thr Ser Tyr Leu His Val Ala Lys
    130                 135                 140 atc tgg ttc tgt ttc ccg ttg ttc cga gaa tat ctg atg agt aac ggg       480
Ile Trp Phe Cys Phe Pro Leu Phe Arg Glu Tyr Leu Met Ser Asn Gly
145                 150                 155                 160 ccg gtt tca gtg tct aag gag agt ttg tct cat gtg ctg agc aag gat       528
Pro Val Ser Val Ser Lys Glu Ser Leu Ser His Val Leu Ser Lys Asp
                165                 170                 175 gga ggt ggc aat gtc tca atc att gtc ctc gga ggt gca aag gag gcg       576
Gly Gly Gly Asn Val Ser Ile Ile Val Leu Gly Gly Ala Lys Glu Ala
            180                 185                 190 ctg gag gct cac cca gga aca ttc acc ctg tgc atc cgc cag cgc aaa       624
Leu Glu Ala His Pro Gly Thr Phe Thr Leu Cys Ile Arg Gln Arg Lys
        195                 200                 205 ggg ttt gtt aag atg gcc ttg acc cat ggt gcc agt ttg gtt cca gta       672
Gly Phe Val Lys Met Ala Leu Thr His Gly Ala Ser Leu Val Pro Val
    210                 215                 220 ttt tct ttt ggt gaa aat gat cta tat aag caa att aac aac ccc aaa       720
Phe Ser Phe Gly Glu Asn Asp Leu Tyr Lys Gln Ile Asn Asn Pro Lys
225                 230                 235                 240 ggc tcc tgg cta cga act ata caa gac gca atg tat gat tca atg gga       768
Gly Ser Trp Leu Arg Thr Ile Gln Asp Ala Met Tyr Asp Ser Met Gly
                245                 250                 255 gta gcc ttg cca ctg ata tat gcc aga gga att ttc cag cac tac ttt       816
Val Ala Leu Pro Leu Ile Tyr Ala Arg Gly Ile Phe Gln His Tyr Phe
            260                 265                 270 ggc ata atg ccc tat cgg aag ctg atc tac act gtt gtt ggc cgc cct       864
Gly Ile Met Pro Tyr Arg Lys Leu Ile Tyr Thr Val Val Gly Arg Pro
        275                 280                 285 atc cct gtt cag cag att ctg aac ccg acc tca gag cag att gaa gag       912
Ile Pro Val Gln Gln Ile Leu Asn Pro Thr Ser Glu Gln Ile Glu Glu
    290                 295                 300 ctg cat cag aca tac cta gag gag cta aag aaa cta ttc aat gaa cac       960
Leu His Gln Thr Tyr Leu Glu Glu Leu Lys Lys Leu Phe Asn Glu His
305                 310                 315                 320 aaa ggg aaa tat ggg att ccg gag cac gaa act ctg gta ttt aaa taa      1008
Lys Gly Lys Tyr Gly Ile Pro Glu His Glu Thr Leu Val Phe Lys  *
                325                 330                 335
```

<210> SEQ ID NO 24
<211> LENGTH: 335
<212> TYPE: PRT
<213> ORGANISM: mus musculus

<400> SEQUENCE: 24

```
Met Met Val Glu Phe Ala Pro Leu Asn Thr Pro Leu Ala Arg Cys Leu
1               5                   10                  15

Gln Thr Ala Ala Val Leu Gln Trp Val Leu Ser Phe Leu Leu Leu Val
            20                  25                  30

Gln Val Cys Ile Gly Ile Met Val Met Leu Val Leu Tyr Asn Tyr Trp
        35                  40                  45

Phe Leu Tyr Ile Pro Tyr Leu Val Trp Phe Tyr Tyr Asp Trp Arg Thr
    50                  55                  60

Pro Glu Gln Gly Gly Arg Arg Trp Asn Trp Val Gln Ser Trp Pro Val
65                  70                  75                  80

Trp Lys Tyr Phe Lys Glu Tyr Phe Pro Ile Cys Leu Val Lys Thr Gln
                85                  90                  95

Asp Leu Asp Pro Gly His Asn Tyr Ile Phe Gly Phe His Pro His Gly
            100                 105                 110

Ile Phe Val Pro Gly Ala Phe Gly Asn Phe Cys Thr Lys Tyr Ser Asp
        115                 120                 125

Phe Lys Lys Leu Phe Pro Gly Phe Thr Ser Tyr Leu His Val Ala Lys
    130                 135                 140

Ile Trp Phe Cys Phe Pro Leu Phe Arg Glu Tyr Leu Met Ser Asn Gly
145                 150                 155                 160

Pro Val Ser Val Ser Lys Glu Ser Leu Ser His Val Leu Ser Lys Asp
                165                 170                 175

Gly Gly Gly Asn Val Ser Ile Ile Val Leu Gly Gly Ala Lys Glu Ala
            180                 185                 190

Leu Glu Ala His Pro Gly Thr Phe Thr Leu Cys Ile Arg Gln Arg Lys
        195                 200                 205

Gly Phe Val Lys Met Ala Leu Thr His Gly Ala Ser Leu Val Pro Val
    210                 215                 220

Phe Ser Phe Gly Glu Asn Asp Leu Tyr Lys Gln Ile Asn Asn Pro Lys
225                 230                 235                 240

Gly Ser Trp Leu Arg Thr Ile Gln Asp Ala Met Tyr Asp Ser Met Gly
                245                 250                 255

Val Ala Leu Pro Leu Ile Tyr Ala Arg Gly Ile Phe Gln His Tyr Phe
            260                 265                 270

Gly Ile Met Pro Tyr Arg Lys Leu Ile Tyr Thr Val Val Gly Arg Pro
        275                 280                 285

Ile Pro Val Gln Gln Ile Leu Asn Pro Thr Ser Glu Gln Ile Glu Glu
    290                 295                 300

Leu His Gln Thr Tyr Leu Glu Glu Leu Lys Lys Leu Phe Asn Glu His
305                 310                 315                 320

Lys Gly Lys Tyr Gly Ile Pro Glu His Glu Thr Leu Val Phe Lys
                325                 330                 335
```

<210> SEQ ID NO 25
<211> LENGTH: 22
<212> TYPE: DNA
<213> ORGANISM: Artificial Sequence
<220> FEATURE:
<223> OTHER INFORMATION: 86606 forward primer

```
<400> SEQUENCE: 25
caagcccctt tattgccact ac                                             22

<210> SEQ ID NO 26
<211> LENGTH: 20
<212> TYPE: DNA
<213> ORGANISM: Artificial Sequence
<220> FEATURE:
<223> OTHER INFORMATION: 86606 reverse primer

<400> SEQUENCE: 26
tccccttggc agagaaactg                                                20

<210> SEQ ID NO 27
<211> LENGTH: 28
<212> TYPE: DNA
<213> ORGANISM: Artificial Sequence
<220> FEATURE:
<223> OTHER INFORMATION: 86606 probe

<400> SEQUENCE: 27
ccacgctcgt ctagtcctga aactgcag                                       28

<210> SEQ ID NO 28
<211> LENGTH: 21
<212> TYPE: DNA
<213> ORGANISM: Artificial Sequence
<220> FEATURE:
<223> OTHER INFORMATION: m86606 forward primer

<400> SEQUENCE: 28
ttccccagac gacagacact t                                              21

<210> SEQ ID NO 29
<211> LENGTH: 24
<212> TYPE: DNA
<213> ORGANISM: Artificial Sequence
<220> FEATURE:
<223> OTHER INFORMATION: m86606 reverse primer

<400> SEQUENCE: 29
ctctcaagaa tccctggagt cact                                           24

<210> SEQ ID NO 30
<211> LENGTH: 47
<212> TYPE: DNA
<213> ORGANISM: Artificial Sequence
<220> FEATURE:
<223> OTHER INFORMATION: m86606 probe

<400> SEQUENCE: 30
actgcccttg cccagctagc cagtactgcc cttgcccagc tagccag                  47

<210> SEQ ID NO 31
<211> LENGTH: 25
<212> TYPE: DNA
<213> ORGANISM: Artificial Sequence
<220> FEATURE:
<223> OTHER INFORMATION: hDC2 forward primer

<400> SEQUENCE: 31
ctataggaaa gccatccaca ctgtt                                          25
```

```
<210> SEQ ID NO 32
<211> LENGTH: 20
<212> TYPE: DNA
<213> ORGANISM: Artificial Sequence
<220> FEATURE:
<223> OTHER INFORMATION: hDC2 reverse primer

<400> SEQUENCE: 32
gggtcgggtt cagagtctga                                           20

<210> SEQ ID NO 33
<211> LENGTH: 19
<212> TYPE: DNA
<213> ORGANISM: Artificial Sequence
<220> FEATURE:
<223> OTHER INFORMATION: hDC2 probe

<400> SEQUENCE: 33
ttggccgccc gatccctgt                                            19

<210> SEQ ID NO 34
<211> LENGTH: 20
<212> TYPE: DNA
<213> ORGANISM: Artificial Sequence
<220> FEATURE:
<223> OTHER INFORMATION: 101188 forward primer

<400> SEQUENCE: 34
ggctcaccca ggaacattca                                           20

<210> SEQ ID NO 35
<211> LENGTH: 23
<212> TYPE: DNA
<213> ORGANISM: Artificial Sequence
<220> FEATURE:
<223> OTHER INFORMATION: 101188 reverse primer

<400> SEQUENCE: 35
ggtcaaggcc atcttaacaa acc                                       23

<210> SEQ ID NO 36
<211> LENGTH: 20
<212> TYPE: DNA
<213> ORGANISM: Artificial Sequence
<220> FEATURE:
<223> OTHER INFORMATION: 101188 probe

<400> SEQUENCE: 36
ctgtgcatcc gccagcgcaa                                           20

<210> SEQ ID NO 37
<211> LENGTH: 19
<212> TYPE: DNA
<213> ORGANISM: Artificial Sequence
<220> FEATURE:
<223> OTHER INFORMATION: 112023 forward primer

<400> SEQUENCE: 37
gcggccacaa ggatgtaaa                                            19

<210> SEQ ID NO 38
<211> LENGTH: 22
<212> TYPE: DNA
<213> ORGANISM: Artificial Sequence
<220> FEATURE:
<223> OTHER INFORMATION: 112023 reverse primer
```

```
<400> SEQUENCE: 38
gagctacctt gccatctttt gg                                              22

<210> SEQ ID NO 39
<211> LENGTH: 56
<212> TYPE: DNA
<213> ORGANISM: Artificial Sequence
<220> FEATURE:
<223> OTHER INFORMATION: 112023 probe

<400> SEQUENCE: 39
agcaggtaga cgaacaatgg ctgcaagatc ttgcagccat tgttcgtcta cctgct         56

<210> SEQ ID NO 40
<211> LENGTH: 20
<212> TYPE: DNA
<213> ORGANISM: Artificial Sequence
<220> FEATURE:
<223> OTHER INFORMATION: m112023 forward primer

<400> SEQUENCE: 40
cgttgccatg ttttggattg                                                 20

<210> SEQ ID NO 41
<211> LENGTH: 18
<212> TYPE: DNA
<213> ORGANISM: Artificial Sequence
<220> FEATURE:
<223> OTHER INFORMATION: m112023 reverse primer

<400> SEQUENCE: 41
tgttggtagc ggccacaa                                                   18

<210> SEQ ID NO 42
<211> LENGTH: 32
<212> TYPE: DNA
<213> ORGANISM: Artificial Sequence
<220> FEATURE:
<223> OTHER INFORMATION: m112023 probe

<400> SEQUENCE: 42
cagccattgt taatttgcct attgttcaca cc                                   32

<210> SEQ ID NO 43
<211> LENGTH: 20
<212> TYPE: DNA
<213> ORGANISM: Artificial Sequence
<220> FEATURE:
<223> OTHER INFORMATION: 112024 forward primer

<400> SEQUENCE: 43
tcaatgctgg caccaaagtg                                                 20

<210> SEQ ID NO 44
<211> LENGTH: 24
<212> TYPE: DNA
<213> ORGANISM: Artificial Sequence
<220> FEATURE:
<223> OTHER INFORMATION: 112024 reverse primer

<400> SEQUENCE: 44
tggtgagata gtcccaagaa acag                                            24
```

```
<210> SEQ ID NO 45
<211> LENGTH: 24
<212> TYPE: DNA
<213> ORGANISM: Artificial Sequence
<220> FEATURE:
<223> OTHER INFORMATION: 112024 probe

<400> SEQUENCE: 45
aggcccgtct ccctaggct cttc                                              24

<210> SEQ ID NO 46
<211> LENGTH: 21
<212> TYPE: DNA
<213> ORGANISM: Artificial Sequence
<220> FEATURE:
<223> OTHER INFORMATION: m58765 forward primer

<400> SEQUENCE: 46
ggtgagtgcc gatcacattc t                                                21

<210> SEQ ID NO 47
<211> LENGTH: 21
<212> TYPE: DNA
<213> ORGANISM: Artificial Sequence
<220> FEATURE:
<223> OTHER INFORMATION: m58765 reverse primer

<400> SEQUENCE: 47
caacgatgat ggcaagcaag t                                                21

<210> SEQ ID NO 48
<211> LENGTH: 36
<212> TYPE: DNA
<213> ORGANISM: Artificial Sequence
<220> FEATURE:
<223> OTHER INFORMATION: m58765 probe

<400> SEQUENCE: 48
tccaggaagg gcggcgggcc cgccgccctt cctgga                                36

<210> SEQ ID NO 49
<211> LENGTH: 18
<212> TYPE: DNA
<213> ORGANISM: Artificial Sequence
<220> FEATURE:
<223> OTHER INFORMATION: 58765 forward primer

<400> SEQUENCE: 49
tgaccgcgcc atttccta                                                    18

<210> SEQ ID NO 50
<211> LENGTH: 24
<212> TYPE: DNA
<213> ORGANISM: Artificial Sequence
<220> FEATURE:
<223> OTHER INFORMATION: 58765 reverse primer

<400> SEQUENCE: 50
gattcagact ggtccaaacc ctat                                             24

<210> SEQ ID NO 51
<211> LENGTH: 28
<212> TYPE: DNA
<213> ORGANISM: Artificial Sequence
<220> FEATURE:
<223> OTHER INFORMATION: 58765 probe
```

```
<400> SEQUENCE: 51
tccttccatg accctccatt gctcctag                                              28

<210> SEQ ID NO 52
<211> LENGTH: 22
<212> TYPE: DNA
<213> ORGANISM: Artificial Sequence
<220> FEATURE:
<223> OTHER INFORMATION: 58765 short forward primer

<400> SEQUENCE: 52
cctggatcct tcacgctgtt ac                                                    22

<210> SEQ ID NO 53
<211> LENGTH: 21
<212> TYPE: DNA
<213> ORGANISM: Artificial Sequence
<220> FEATURE:
<223> OTHER INFORMATION: 58765 short reverse primer

<400> SEQUENCE: 53
aggcttgata cccgtgtgtc a                                                     21

<210> SEQ ID NO 54
<211> LENGTH: 46
<212> TYPE: DNA
<213> ORGANISM: Artificial Sequence
<220> FEATURE:
<223> OTHER INFORMATION: 58765 short probe

<400> SEQUENCE: 54
cggaaccgaa agggcttcgt cagctgacga agccctttcg gttccg                          46

<210> SEQ ID NO 55
<211> LENGTH: 24
<212> TYPE: DNA
<213> ORGANISM: Artificial Sequence
<220> FEATURE:
<223> OTHER INFORMATION: 60489 forward primer

<400> SEQUENCE: 55
cgaggaggaa gtcaatcact atca                                                  24

<210> SEQ ID NO 56
<211> LENGTH: 21
<212> TYPE: DNA
<213> ORGANISM: Artificial Sequence
<220> FEATURE:
<223> OTHER INFORMATION: 60489 reverse primer

<400> SEQUENCE: 56
tttccttgtg ctcctcgaag a                                                     21

<210> SEQ ID NO 57
<211> LENGTH: 26
<212> TYPE: DNA
<213> ORGANISM: Artificial Sequence
<220> FEATURE:
<223> OTHER INFORMATION: 60489 probe

<400> SEQUENCE: 57
ccctctacat gacggacctg gagcag                                                26
```

```
<210> SEQ ID NO 58
<211> LENGTH: 24
<212> TYPE: DNA
<213> ORGANISM: Artificial Sequence
<220> FEATURE:
<223> OTHER INFORMATION: 112041 forward primer

<400> SEQUENCE: 58
gagacccaag agctgacaat taca                                            24

<210> SEQ ID NO 59
<211> LENGTH: 19
<212> TYPE: DNA
<213> ORGANISM: Artificial Sequence
<220> FEATURE:
<223> OTHER INFORMATION: 112041 reverse primer

<400> SEQUENCE: 59
tggatccctc atggctttg                                                  19

<210> SEQ ID NO 60
<211> LENGTH: 27
<212> TYPE: DNA
<213> ORGANISM: Artificial Sequence
<220> FEATURE:
<223> OTHER INFORMATION: 112041 probe

<400> SEQUENCE: 60
aacaggagcc acattcccca ttgatca                                         27

<210> SEQ ID NO 61
<211> LENGTH: 712
<212> TYPE: DNA
<213> ORGANISM: human
<220> FEATURE:
<221> NAME/KEY: CDS
<222> LOCATION: (2)...(712)

<400> SEQUENCE: 61 g cta gtt aaa act gca aag ttg ggc acc tcc tgg aac tac ctc ttt gac     49
  Leu Val Lys Thr Ala Lys Leu Gly Thr Ser Trp Asn Tyr Leu Phe Asp
   1               5                  10                  15 ttc cac cct cac agg gtc ctg gtc gtg gga gcc ttc gcc aac ttc tgc       97
Phe His Pro His Arg Val Leu Val Val Gly Ala Phe Ala Asn Phe Cys
             20                  25                  30 aca gag ccc acg ggc tgc tcc tgc ctc ttc ccc aaa ctc ccg cca cac      145
Thr Glu Pro Thr Gly Cys Ser Cys Leu Phe Pro Lys Leu Pro Pro His
         35                  40                  45 ctg ctc atg ctg cct tgt tgg ttc cat ctc ctc ttc ttc cag gac tac      193
Leu Leu Met Leu Pro Cys Trp Phe His Leu Leu Phe Phe Gln Asp Tyr
     50                  55                  60 atc atg tca ggt ggt ttg gtc tcc ttt gtc aag gcc ccg ctg cct cag      241
Ile Met Ser Gly Gly Leu Val Ser Phe Val Lys Ala Pro Leu Pro Gln
 65                  70                  75                  80 tgg tgg cca ggt ggc tgt cct ggc gtg gga ggg ccc ctg cag gcg ctg      289
Trp Trp Pro Gly Gly Cys Pro Gly Val Gly Gly Pro Leu Gln Ala Leu
                 85                  90                  95 gag gca aaa ccc gga caa ctg agc ttg ccg att cgg aat cag aag aga      337
Glu Ala Lys Pro Gly Gln Leu Ser Leu Pro Ile Arg Asn Gln Lys Arg
            100                 105                 110 ttg gtt aag tca gct ctg gaa ctc ggg gag aat gag ctc ttc cag cag      385
Leu Val Lys Ser Ala Leu Glu Leu Gly Glu Asn Glu Leu Phe Gln Gln
        115                 120                 125
```

```
ttc ccg aac ccg cag agc tcg tgg gtg cag agg acg cag gag gct ctg      433
Phe Pro Asn Pro Gln Ser Ser Trp Val Gln Arg Thr Gln Glu Ala Leu
130                 135                 140 cgt ccg ctg cta agc gtg gcc ctg cag ctg ttc ctg ggc cgc cgg ggc      481
Arg Pro Leu Leu Ser Val Ala Leu Gln Leu Phe Leu Gly Arg Arg Gly
145                 150                 155                 160 ctc ccg ctg ccc ttc cgc gcg ccc atc cgc acc gta gtg ggg tcg gcg      529
Leu Pro Leu Pro Phe Arg Ala Pro Ile Arg Thr Val Val Gly Ser Ala
                165                 170                 175 att ccc gtg cag cag agc ccc ccg ccc agt ccg gcc cag gtg gac acg      577
Ile Pro Val Gln Gln Ser Pro Pro Ser Pro Ala Gln Val Asp Thr
                180                 185                 190 ctg caa gcg cgc tac gtg ggg cga ctc acg cag ctc ttc gag gag cac      625
Leu Gln Ala Arg Tyr Val Gly Arg Leu Thr Gln Leu Phe Glu Glu His
            195                 200                 205 cag gcg cgc tat ggt gtc ccc gcc gac aga cac ctg gtc ctc acg gag      673
Gln Ala Arg Tyr Gly Val Pro Ala Asp Arg His Leu Val Leu Thr Glu
    210                 215                 220 gcg cgc ccc acc gcc tgg cct cgc ctg tcc gct ggg tga                  712
Ala Arg Pro Thr Ala Trp Pro Arg Leu Ser Ala Gly *
225                 230                 235

<210> SEQ ID NO 62
<211> LENGTH: 236
<212> TYPE: PRT
<213> ORGANISM: human

<400> SEQUENCE: 62

Leu Val Lys Thr Ala Lys Leu Gly Thr Ser Trp Asn Tyr Leu Phe Asp
 1               5                  10                  15

Phe His Pro His Arg Val Leu Val Gly Ala Phe Ala Asn Phe Cys
                20                  25                  30

Thr Glu Pro Thr Gly Cys Ser Cys Leu Phe Pro Lys Leu Pro Pro His
                35                  40                  45

Leu Leu Met Leu Pro Cys Trp Phe His Leu Leu Phe Phe Gln Asp Tyr
50                  55                  60

Ile Met Ser Gly Gly Leu Val Ser Phe Val Lys Ala Pro Leu Pro Gln
65                  70                  75                  80

Trp Trp Pro Gly Gly Cys Pro Val Gly Gly Pro Leu Gln Ala Leu
                85                  90                  95

Glu Ala Lys Pro Gly Gln Leu Ser Leu Pro Ile Arg Asn Gln Lys Arg
                100                 105                 110

Leu Val Lys Ser Ala Leu Glu Leu Gly Glu Asn Glu Leu Phe Gln Gln
            115                 120                 125

Phe Pro Asn Pro Gln Ser Ser Trp Val Gln Arg Thr Gln Glu Ala Leu
        130                 135                 140

Arg Pro Leu Leu Ser Val Ala Leu Gln Leu Phe Leu Gly Arg Arg Gly
145                 150                 155                 160

Leu Pro Leu Pro Phe Arg Ala Pro Ile Arg Thr Val Val Gly Ser Ala
                165                 170                 175

Ile Pro Val Gln Gln Ser Pro Pro Ser Pro Ala Gln Val Asp Thr
                180                 185                 190

Leu Gln Ala Arg Tyr Val Gly Arg Leu Thr Gln Leu Phe Glu Glu His
            195                 200                 205
```

```
Gln Ala Arg Tyr Gly Val Pro Ala Asp Arg His Leu Val Leu Thr Glu
    210                 215                 220

Ala Arg Pro Thr Ala Trp Pro Arg Leu Ser Ala Gly
225                 230                 235

<210> SEQ ID NO 63
<211> LENGTH: 20
<212> TYPE: DNA
<213> ORGANISM: Artificial Sequence
<220> FEATURE:
<223> OTHER INFORMATION: 112037 forward primer

<400> SEQUENCE: 63
cctgcctctt ccccaaactc                                         20

<210> SEQ ID NO 64
<211> LENGTH: 24
<212> TYPE: DNA
<213> ORGANISM: Artificial Sequence
<220> FEATURE:
<223> OTHER INFORMATION: 112037 reverse primer

<400> SEQUENCE: 64
gaagaagagg agatggaacc aaca                                    24

<210> SEQ ID NO 65
<211> LENGTH: 21
<212> TYPE: DNA
<213> ORGANISM: Artificial Sequence
<220> FEATURE:
<223> OTHER INFORMATION: 112037 probe

<400> SEQUENCE: 65
cgccacacct gctcatgctg c                                       21
```

HUMAN DIACYLGLYCEROL ACYLTRANSFERASE 2 (DGAT2) FAMILY MEMBERS AND USES THEREFOR

CROSS-REFERENCE TO RELATED APPLICATIONS

This application is a divisional of U.S. patent application Ser. No. 10/324,618, filed Dec. 19, 2002, now abandoned, which claims the benefit of U.S. Provisional Application No. 60/341,947, filed Dec. 19, 2001, now abandoned, and U.S. Provisional Application No. 60/411,859, filed Sep. 19, 2002, now abandoned. Each of these applications is hereby incorporated in its entirety by reference herein.

The contents of the Sequence Listing are submitted herewith on compact disc in duplicate. Each disc has a copy of the file "sequence listing.txt." which is incorporated herein by this reference. This file is 104 kilobytes and is a copy of the sequence listing filed in U.S. patent application Ser. No. 10/324,618, filed Dec. 19, 2002. This file was copied onto compact disc on Dec. 6, 2005.

BACKGROUND OF THE INVENTION

Obesity, the most prevalent of body weight disorders, is the most important nutritional disorder in the western world, with estimates of its prevalence ranging from 30% to 50% within the middle-aged population. Obesity, defined as an excess of body fat relative to lean body mass, also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554-558; Grundy, S. M. & Barnett, J. P., 1990, Dis. Mon. 36: 641-731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity. The nature, however, of the genetic factors which control body composition are unknown, and attempts to identify molecules involved in such control have generally been empiric, and the parameters of body composition and/or substrate flux have not yet been identified (Friedman, J. M. et al., 1991, Mammalian Gene 1:130-144).

The epidemiology of obesity strongly shows that the disorder exhibits inherited characteristics (Stunkard, 1990, N. Eng. J. Med. 322:1483). Moll et al., have reported that, in many populations, obesity seems to be controlled by a few genetic loci (Moll et al. 1991, Am. J. Hum. Gen. 49:1243). In addition, human twin studies strongly suggest a substantial genetic basis in the control of body weight, with estimates of heritability of 80-90% (Simopoulos, A. P. & Childs B., eds., 1989, in "Genetic Variation and Nutrition in Obesity", World Review of Nutrition and Diabetes 63, S. Karger, Basel, Switzerland; Botjeson, M., 1976, Acta. Paediatr. Scand. 65:279-287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. Studies of the genetics of human obesity, and of animal models of obesity demonstrate that obesity results from complex defective regulation of both food intake, food induced energy expenditure, and of the balance between lipid and lean body anabolism. It has now been established that the maintenance of body weight, satiety and energy expenditure is a complex process, regulated at various levels, including external and hypothalmic control of satiety, neuroendocrine and sympathetic nervous system control of metabolic processes, as well as enzymatic and transcriptional controls of utilization of glucose, and adipogenesis (Kahn, 2000, Nature Genetics 25: 6; and Palou, et al., 2000, Eur. J. Nutr. 39: 127).

It is estimated that approximately 40% of calories in the western diet are from fat. Thus, blocking absorption of a fraction of such fat would lead to weight loss. The pathways involved in fatty acid absorption in the small intestine are fairly well understood. Fatty acids are liberated from triglycerides in the lumen of the small intestine through the action of pancreatic lipase. Free fatty acids then cross the plasma membrane of the enterocytes, a transport mechanism probably utilizing FATP4, and, once in the enterocyte, are re-esterified into triacylglycerols, the major form of energy stored in adipose tissue, which are packaged into chylomicrons prior to absorption.

Although production of diacylglycerol can be accomplished through various mechanisms, the final rate-limiting step in biosynthesis of triacylglycerol is accomplished via the enzyme diacyl glycerol acyltransferase (DGAT). Although it has been known that DGAT activity is increased in obese rodents, DGAT1 deficient mice are resistant to high fat-diet induced obesity and have increased energy expenditure (Smith, 2000, Nature Genetics 25: 87). Until recently when a second DGAT enzyme (DGAT2) was identified, it was believed a single enzyme was responsible for synthesis of triacylglycerol (Cases et al. 2001 J. Biol. Chem. 276: 38870). An understanding of regulation and maintenance of this rate limiting step of triglyceride can provide insight into the regulation of production and maintenance of energy stores and fat, and assist in the development of treatment for obesity and related disorders involving production of triacylglycerols.

Given the importance of understanding body weight homeostasis and, further, given the severity and prevalence of disorders, including obesity, which affect body weight and body composition, there exists a great need for the systematic identification of genes and regulation of genes involved in these complex processes and disorders. Such identification will provide rationales and facilitate development of specific compounds acting via modulation of metabolic activity for use in the treatment of obesity and related disorders.

DESCRIPTION OF THE INVENTION

The present invention is based, in part, on the discovery of novel human diacylglycerol acyltransferase 2 (DGAT2) family members, referred to herein as "60489," "112041," and "112037." The nucleotide sequence of cDNAs encoding 60489, 112041 and 112037 are shown in SEQ ID NO:7, SEQ ID NO:19, and SEQ ID NO:61 respectively; the amino acid sequences of 60489, 112041, and 112037 polypeptides are shown in SEQ ID NO:8, SEQ ID NO:20, and SEQ ID NO:62.

Additionally, the invention is based on the discovery of novel expression and regulation of human diacylglycerol acyltransferase 2 (DGAT2) family members referred to herein as "58765," "58765short," "86606," "112023," "112024," and "hDC2." The nucleotide sequence of a cDNA encoding 58765 is shown in SEQ ID NO:1, and the amino acid sequence of a 58765 polypeptide is shown in SEQ ID NO:2. The nucleotide sequence of a cDNA encoding 58765short is shown in SEQ ID NO:3, and the amino acid sequence of a 58765short polypeptide is shown in SEQ ID NO:4. The nucleotide sequence of a cDNA encoding 86606 is shown in SEQ ID NO:9, and the amino acid sequence of a 86606 polypeptide is shown in SEQ ID NO:10. The nucleotide sequence of a cDNA encoding 112023 is shown in SEQ ID NO:13, and the amino acid sequence of a 112023 polypeptide is shown in SEQ ID NO:14. The nucleotide sequence of a cDNA encoding 112024 is shown in SEQ ID NO:17, and the amino acid sequence of a 112024 polypeptide is shown in SEQ ID NO:18. The nucleotide sequence of a cDNA encoding hDC2 is shown in SEQ ID NO:21, and the amino acid sequence of a hDC2 polypeptide is shown in SEQ ID NO:22.

Further, the present invention provides murine gene sequences were also identified which are related to DGAT2 sequences. The murine DGAT2 orthologue sequence (m86606) is depicted in SEQ ID NO:11, and the amino acid sequence of a m86606 polypeptide is shown in SEQ ID NO:12. The murine DGAT2 family member sequence m58765 sequence is shown in SEQ ID NO:5, and the amino acid sequence of a m58765 polypeptide is shown in SEQ ID NO:6. The DGAT2 family member nucleotide sequence of m112023 is shown in SEQ ID NO:15, and the amino acid sequence of a m112023 polypeptide is shown in SEQ ID NO:16. The DGAT2 family member nucleotide sequence of mDC2 is shown in SEQ ID NO:23, and the amino acid sequence of a mDC2 polypeptide is shown in SEQ ID NO:24.

Accordingly, in one aspect, the invention features nucleic acid molecules which encode a DGAT2 family member protein or polypeptide, or a fragment thereof, e.g., a biologically active portion of the DGAT2 family member protein. In a preferred embodiment, the isolated nucleic acid molecule encodes a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62. In other embodiments, the invention provides an isolated DGAT2 family member nucleic acid molecule having the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61. In other embodiments, the invention provides a nucleic acid molecule which hybridizes under stringent hybridization conditions to a nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, wherein the nucleic acid encodes a full length DGAT2 family member protein or an active fragment thereof.

In a related aspect, the invention further provides nucleic acid constructs which include a DGAT2 family member nucleic acid molecule described herein. In certain embodiments, the nucleic acid molecules of the invention are operatively linked to native or heterologous regulatory sequences. Also included, are vectors and host cells containing the DGAT2 family member nucleic acid molecules of the invention e.g., vectors and host cells suitable for producing DGAT2 family member nucleic acid molecules and polypeptides.

In another related aspect, the invention provides nucleic acid of DGAT2 family member-encoding nucleic acids. The fragments of the invention can be suitable as primers or hybridization probes for the detection of DGAT2 family member encoding nucleic acids.

In still another related aspect, isolated nucleic acid molecules that are antisense to a DGAT2 family member encoding nucleic acid molecule are provided.

In another aspect, the invention features, DGAT2 family member polypeptides, and biologically active or antigenic fragments thereof that are useful, e.g., as reagents or targets in assays applicable to treatment and diagnosis of DGAT2 family member-mediated or -related disorders. In another embodiment, the invention provides DGAT2 family member polypeptides having a DGAT2 family member activity. Preferred polypeptides are DGAT2 family member proteins including at least one acyltransferase domain, and/or plsC domain, and, preferably, having a DGAT2 family member activity, e.g., a DGAT2 family member activity as described herein.

In other embodiments, the invention provides DGAT2 family member polypeptides, e.g., a DGAT2 family member polypeptide having the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62; an amino acid sequence that is substantially identical to the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62; or an amino acid sequence encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, wherein the nucleic acid encodes a full length DGAT2 family member protein or an active fragment thereof.

In a related aspect, the invention further provides nucleic acid constructs which include a DGAT2 family member nucleic acid molecule described herein.

In a related aspect, the invention provides DGAT2 family member polypeptides or fragments operatively linked to non-DGAT2 family member polypeptides to form fusion proteins.

In another aspect, the invention features antibodies and antigen-binding fragments thereof, that react with, or more preferably specifically bind DGAT2 family member polypeptides.

The present invention is based, at least in part, on the discovery that DGAT2 family member molecules are expressed at increased levels in adipose, liver, small intestine, colon, and kidney tissues, (see Examples 3-7 and Tables 1-8 described herein). DGAT2 family member molecules were further found to be upregulated during adipocyte differentiation, and downregulated during exposure to starvation conditions or mice fed high fat diets (i.e., under conditions that affect adipocyte metabolism) as well as in genetic models of obesity (see Example 3 and Tables 3-8).

Accordingly, the present invention provides methods for the diagnosis and treatment of metabolic and related disorders including but not limited to obesity, hyperlipidemia and other lipid disorders and diabetes.

In one aspect, the invention provides methods of screening for compounds that modulate the expression or activity of the DGAT2 family member polypeptides or nucleic acids. The method includes contacting a sample expressing a DGAT2 family member nucleic acid or polypeptide with a test compound and assaying the ability of the test compound to modulate the expression of a DGAT2 family member nucleic acid or the activity of a DGAT2 family member polypeptide.

In one embodiment, the invention provides methods for identifying a compound capable of treating a metabolic disorder, e.g., obesity, hyperlipidemia, and diabetes. The method includes assaying the ability of the compound to modulate DGAT2 family member nucleic acid expression or DGAT2 family member polypeptide activity. In one embodiment, the ability of the compound to modulate nucleic acid expression or DGAT2 family member polypeptide activity is determined by detecting modulation of lipogenesis. In another embodiment, the ability of the compound to modulate nucleic acid expression or DGAT2 family member polypeptide activity is determined by detecting modulation of triglyceride biosynthesis. In still another embodiment, the ability of the compound to modulate nucleic acid expression or DGAT2 family member polypeptide activity is determined by detecting modulation of hyperplastic growth. In yet another embodiment, the ability of the compound to modulate nucleic acid expression or DGAT2 family member polypeptide activity is determined by detecting modulation of hypertrophic growth.

In another aspect, the invention provides methods for identifying a compound capable of modulating an adipocyte activity, e.g., hyperplastic growth, hypertrophic growth, or lipogenesis. The method includes contacting an adipocyte expressing a DGAT2 family member nucleic acid or polypeptide with a test compound and assaying the ability of the test compound to modulate the expression of a DGAT2 family member nucleic acid or the activity of a DGAT2 family member polypeptide.

In still another aspect, the invention provides methods for determining acyltransferase activity of a polypeptide. Such methods include combining a sample comprising an acyltransferase polypeptide with a fatty acyl coA substrate and a acylglyceride substrate under conditions suitable to carry out enzyme activity, and determining the amount of acylglycerol product formed, wherein product formation is a determination of acylglycerol-acyltransferase activity. In certain aspects, one substrate can be biotinylated and the other substrate can be radiolabeled (e.g., radiolabeled acylglyceride and biotinylated fatty acyl coA). Product formation can be determined using biotin capture and radiometric determination (eg, SPA (scintillation proximity assay)) assays. Provided acyltransferase activity methods can be used to detect any acyltransferase activity (e.g., monoacylglycerol acyltransferase, diacylglycerol acyltransferase). In particular embodiments, acyltransferase activity methods can be used to determine enzyme activity of the DGAT2 family members provided herein.

Yet another aspect includes methods for identifying compounds which modulate acyltransferase activity. The provided methods include the described methods for determining acyltransferase activity, with additional steps including contacting the sample comprising an acyltransferase polypeptide and fatty acyl coA and acylglyceride substrates with one or more test compounds. Test compounds can be added to the sample at any time before, during, or after combining the composition comprising acyltransferase and substrates. Enzyme activity is determined by measuring product formation, wherein a change in the amount of acyltransferase activity in the presence of test compound identifies a compound which modulates acyltransferase activity.

In another aspect, the invention provides methods for modulating an adipocyte activity, e.g., hyperplastic growth, hypertrophic growth, or lipogenesis. The method includes contacting an adipocyte with a DGAT2 family member modulator, for example, an anti-DGAT2 family member antibody, a DGAT2 family member polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, or a fragment thereof, a DGAT2 family member polypeptide comprising an amino acid sequence which is at least 90 percent identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, an isolated naturally occurring allelic variant of a polypeptide consisting of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, a small molecule, an antisense DGAT2 family member nucleic acid molecule, a nucleic acid molecule of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, or a fragment thereof, or a ribozyme.

In still another aspect, the invention provides a process for modulating DGAT2 family member polypeptide or nucleic acid expression or activity, e.g. using the screened compounds. In certain embodiments, the methods involve treatment of conditions related to aberrant activity or expression of the DGAT2 family member polypeptides or nucleic acids, such as conditions involving aberrant or deficient triglyceride biosynthesis (e.g., obesity, lipid disorders).

The invention also provides assays for determining the activity of or the presence or absence of DGAT2 family member polypeptides or nucleic acid molecules in a biological sample, including for disease diagnosis. In one aspect, provided are assays for determining the presence or absence of a genetic alteration in a DGAT2 family member polypeptide or nucleic acid molecule, including for disease diagnosis.

In one embodiment, methods include identifying a nucleic acid associated with a metabolic disorder, e.g., obesity, hyperlipidemia, and diabetes.

In yet another aspect, the invention features a method for identifying a subject having an obesity disorder characterized by aberrant DGAT2 family member polypeptide activity or aberrant DGAT2 family member nucleic acid expression. The method includes contacting a sample obtained from the subject and expressing a DGAT2 family member nucleic acid or polypeptide with a test compound and assaying the ability of the test compound to modulate the expression of a DGAT2 family member nucleic acid or the activity of a DGAT2 family member polypeptide.

In yet another aspect, the invention features a method for treating a subject having a metabolic disorder, e.g., obesity, diabetes, hyperlipidemia, characterized by aberrant DGAT2 family member polypeptide activity or aberrant DGAT2 family member nucleic acid expression. The method includes administering to the subject a DGAT2 family member modulator, e.g., in a pharmaceutically acceptable formulation or by using a gene therapy vector. Embodiments of this aspect of the invention include the DGAT2 family member modulator being any of an organic small molecule, an anti-DGAT2 family member antibody, a DGAT2 family member polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, or a fragment thereof, a DGAT2 family member polypeptide comprising an amino acid sequence which is at least 90 percent identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, an isolated naturally occurring allelic variant of a polypeptide consisting of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62, an antisense DGAT2 family member nucleic acid molecule, a nucleic acid molecule of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, or a fragment thereof, or a ribozyme.

The present invention is based, at least in part, on the discovery of novel molecules, referred to herein as "DGAT2 family member" nucleic acid and polypeptide molecules, which play a role in, or function in, catalyzing the final step in the re-esterification of fatty acids to produce triglycerols, and/or play a role in production and regulation of fat and energy stores in mammals. This metabolic pathway is described in Lodish et al. (1995) *Molecular Cell Biology* (Scientific American Books Inc., New York, N.Y.) and Stryer *Biochemistry*, (W. H. Freeman, New York), the contents of which are incorporated herein by reference. In one embodiment, the DGAT2 family member molecules modulate the activity of one or more proteins involved in production of triacylglycerols, and/or production of fat stores e.g., adipose fat stores. In another embodiment, the DGAT2 family member molecules of the present invention are capable of modulating the esterification state of fatty acid molecules for the production of one or more molecules involved in adipose energy stores, as described in, for example, Lodish et al. and Stryer, supra. Additionally, the DGAT2 family members of the invention may modulate triglyceride production and energy storage in tissues and cells including liver, small intestine, kidney, adipose, skeletal muscle, pancreas, heart, spleen, brain, hypothalamus, lung, etc.

As used herein, the term "diacylglycerol acyltransferase" "acyl-CoA:diacylglycerol acyltransferase" or "DGAT" includes a protein, polypeptide, or other non-proteinaceous molecule that is capable of modulating the esterification state of diacylglycerol (DAG) molecules. DGATs play a role in biosynthetic pathways associated with production of fat stores. For example, DGATs are involved in the regulation of biosynthesis of triacylglycerols. The enzyme reaction catalyzed by Acyl-CoA:diacylglycerol acyltransferases (DGATs) involves the coupling of an acyl-CoA (1) to a preformed diacylglycerol (2) producing one equivalent of Coenzyme A (CoA) and triacylglycerol.

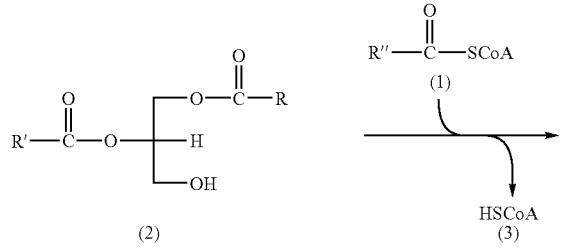

-continued

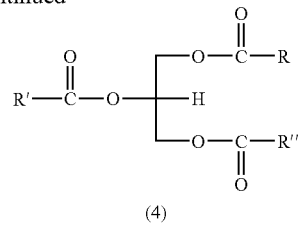

Novel DGAT Sequences

The present invention is based, at least in part, on the discovery of novel molecules, referred to herein as diacylglycerol acyltransferase 2 (DGAT2) family member protein and nucleic acid molecules, that comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features diacylglycerol acyltransferase 2 (DGAT2) family member nucleic acid molecules, preferably human DGAT2 family member molecules, that were initially identified based on related sequence or protein domain characteristic of acyl glycerol phosphate acyltransferase family of proteins. Such sequences are referred to as "DGAT2 family member" sequences indicating that the genes share sequence similarity with diacylglycerol acyltransferase 2 gene. Specifically, novel human DGAT2 family member family members, 60489, 112041, and 112037 are provided. They are highly expressed in small intestine, adipose, and liver where triglyceride synthesis occurs.

In addition, we have demonstrated tissue expression and regulation of additional human DGAT2 family member family members 86606, 58765, 112023, 112024, hDC2, as well as murine orthologues m86606, m58765, m112023, and mDC2. They are also highly expressed in tissues where triglyceride synthesis occurs, expression is regulated under conditions that change adipocyte metabolism both in vitro and in vivo. DGAT2 family member family members are therefore a candidate target to identify small molecules for the treatment of obesity, diabetes, and/or lipid disorders in humans. It is conceivable that inhibition of these genes, either individually or collectively, will lead to decreased triglyceride synthesis and fat accumulation in vivo. Inhibitors, therefore, have potentials for anti-fat absorption and can be used to treat obesity and its related disorders.

Human DGAT2 Family Members

The human DGAT2, (herein referred to as 86606) sequence is depicted in SEQ ID NO:9, which is approximately 2428 nucleotides long including untranslated regions, contains a predicted methionine-initiated coding sequence of about 1166 nucleotides (nucleotides 220-1386 of SEQ ID NO:9). The coding sequence encodes a 388 amino acid protein (SEQ ID NO:10). The molecule may have transmembrane segments from amino acids (aa) 70-93 and 100-116 as predicted by MEMSAT. Prosite program analysis was used to predict various sites within the 86606 protein. N-glycosylation sites were predicted at aa 60-63, 173-176 and 228-231. Protein kinase C phosphorylation sites were predicted at aa 23-35, 37-39, 116-118, 152-154, 182-184, and 255-257. Casein kinase II phosphorylation sites were predicted at aa 62-65, 278-281, and 351-354. N-myristoylation sites were predicted at aa 10-15, 41-46, 84-89, 120-125, 169-174, 229-234, 240-245, 318-323, and 378-383. An amidation site was predicted at aa 120-123. The 86606 protein possesses a SMART plsc_2 domain, from about aa 165 to about aa 281, as predicted by HMMer, Version 2.1.1. The plsc domain is believed to function in phospholipid biosynthesis and is characteristic of proteins having glycerolphosphate, 1-acylglycerolphosphate, or 2-acylglycerolphosphoethanolamine acyltransferase activities.

The human DGAT2 family member sequence 60489 (SEQ ID NO:7), which is approximately 1255 nucleotides long including untranslated regions, contains a predicted methionine-initiated coding sequence of about 1025 nucleotides (nucleotides 170-1195 of SEQ ID NO:7) The coding sequence encodes a 341 amino acid protein (SEQ ID NO:8). The molecule may have transmembrane segments from amino acids (aa) 39-63, 109-127, and 271-291 as predicted by MEMSAT. Prosite program analysis was used to predict various sites within the 60489 protein. N-glycosylation sites were predicted at aa 126-129. Protein kinase C phosphorylation sites were predicted at aa 12-14, and 255-257. Casein kinase II phosphorylation sites were predicted at aa 231-234, 304-307, and 317-320. N-myristoylation sites were predicted at aa 2-7, 73-78, 117-122, 193-198, 271-276, and 331-336. An amidation site was predicted at aa 73-76. The 60489 protein possesses a SMART plsc_2 domain, from about aa 110 to about aa 234, as predicted by HMMer, Version 2.1.1. The plsc domain is believed to function in phospholipid biosynthesis and is characteristic of proteins having glycerolphosphate, l-acylglycerolphosphate, or 2-acylglycerolphosphoethanolamine acyltransferase activities.

The DGAT2 family member sequence 112041 (SEQ ID NO:19), which is approximately 1716 nucleotides long including untranslated regions, contains a predicted methionine-initiated coding sequence of about 1013 nucleotides (nucleotides 101-1114 of SEQ ID NO:19) The coding sequence encodes a 337 amino acid protein (SEQ ID NO:20). The molecule may have transmembrane segments from amino acids (aa) 21-42 as predicted by MEMSAT. Prosite program analysis was used to predict various sites within the 112041 protein. An N-glycosylation site was predicted at aa 75-78. Protein kinase C phosphorylation sites were predicted at aa 97-99, 172-174, and 252-254. Casein kinase II phosphorylation sites were predicted at aa 224-227, 235-238, and 248-251. N-myristoylation sites were predicted at aa 66-71, 115-120, 175-180, 186-191, 258-263, and 327-332. An amidation site was predicted at aa 66-69.

The human DGAT2 family member sequence 112037 (SEQ ID NO:61), is a partial sequence approximately 712 nucleotides long, contains a predicted coding sequence of about 711 nucleotides (nucleotides 2-712 of SEQ ID NO:61) The coding sequence encodes a 236 amino acid protein (SEQ ID NO:62). The molecule may have transmembrane segments from amino acids (aa) 22-42 and 49-73, as predicted by MEMSAT. Prosite program analysis was used to predict various sites within the 112037 protein. A Protein kinase C phosphorylation sites was predicted at aa 4-6. A Casein kinase II phosphorylation sites was predicted at aa 116-119. N-myristoylation sites were predicted at aa 8-13, 26-31, 68-73, and 84-89. An amidation site was predicted at aa 156-159.

The DGAT2 family member sequence of 58765 identified two splice variant sequences including 58765 (SEQ ID NO:1), which is approximately 1005 nucleotides long, encodes a 334 amino acid protein (SEQ ID NO:2). The molecule may have dileucine motifs in the tail at about amino acids (aa) 41-42, 48-49, 180-181, and 201-202, as predicted by PSORT. The molecule may have transmembrane segments from amino acids (aa) 38-59 and 103-119 as predicted by MEMSAT. Prosite program analysis was used to predict various sites within the 86606 protein. N-glycosylation sites were predicted at aa 237-240. Protein kinase C phosphorylation sites were predicted at aa 163-165. Casein kinase II phosphorylation sites were predicted at aa 163-166, 225-228, and 297-300. N-myristoylation sites were predicted at aa 116-121, 159-164, 178-183, and 187-192. The 58765 protein possesses a SMART plsc_2 domain, from about aa 111 to about aa 228, as predicted by HMMer, Version 2.1.1. The plsc domain is believed to function in phospholipid biosynthesis and is characteristic of proteins having glycerolphosphate, 1-acylglycerolphosphate, or 2-acylglycerolphosphoethanolamine acyltransferase activities. In addition, the 58765 protein possess a PFAM acyltransferase domain, from about aa 104 to about aa 296, as predicted by HMMer, Version 2.1.1.

Additionally, 58765short (SEQ ID NO:3), which is approximately 855 nucleotides long, encodes a 284 amino acid protein (SEQ ID NO:4). The molecule may have transmembrane segments from amino acids (aa) 38-59 and 103-119 as predicted by MEMSAT. Dileucine motifs may be present in the tail at aa 41-42, 48-49, 180-181, and 201-202, as predicted by PSORT. Prosite program analysis was used to predict various sites within the 58765short protein. A cAMP and cGMP dependent protein kinase phosphorylation site was predicted at aa 277-280. Protein kinase C phosphorylation sites were predicted at aa 163-165, 221-223, and 258-260. Casein kinase II phosphorylation sites were predicted at aa 163-166, and 244-247. N-myristoylation sites were predicted at aa 116-121, 159-164, 178-183, 187-192, 227-232, and 238-243. An ATP/GTP binding site motif was predicted at aa 217-224.

The DGAT2 family member sequence 112023 (SEQ ID NO:13), which is approximately 1279 nucleotides long including untranslated regions, contains a predicted methionine-initiated coding sequence of about 986 nucleotides (nucleotides 42-1028 of SEQ ID NO:13). The coding sequence encodes a 328 amino acid protein (SEQ ID NO:14. The molecule may have transmembrane segments from about amino acids (aa) 13-29, 36-54, 98-116 and 165-183 as predicted by MEMSAT. Dileucine motifs may be present in the tail at aa 15-16, as predicted by PSORT. Prosite program analysis was used to predict various sites within the 112023 protein. A protein kinase C phosphorylation site was predicted at aa 322-324. A casein kinase II phosphorylation site was predicted at aa 219-222. N-myristoylation sites were predicted at aa 62-67, 111-116, 172-177, 181-186, 257-262, and 318-323. An amidation site was predicted at aa 62-65.

The DGAT2 family member sequence 112024 (SEQ ID NO:17), which is approximately 1720 nucleotides long including untranslated regions, contains a predicted methionine-initiated coding sequence of about 1001 nucleotides (nucleotides 1-1002 of SEQ ID NO:17) The coding sequence encodes a 333 amino acid protein (SEQ ID NO:18). The molecule may have transmembrane segments from about amino acids (aa) 37-58, and 130-150 as predicted by MEMSAT. Dileucine motifs may be present in the tail at aa 26-27, 90-91, 170-171, and 272-273, as predicted by PSORT. An N-glycosylation sites was predicted at aa 204-207. A cAMP and cGMP dependent protein kinase phosphorylation site was predicted at aa 68-71. Protein kinase C phosphorylation sites were predicted at aa 5-7, and 172-174. Casein kinase II phosphorylation sites were predicted at aa 5-8, 11-14, and 165-168. N-myristoylation sites were predicted at aa 186-191, 239-244, and 323-328. An amidation site was predicted at aa 66-69. The 112024 protein possesses a SMART plsc_2 domain, from about aa 118 to about aa 314, as predicted by HMMer, Version 2.1.1. The plsc domain is believed to function in phospholipid biosynthesis and is characteristic of proteins having glycerolphosphate, 1-acylglycerolphosphate, or 2-acylglycerolphosphoethanolamine acyltransferase activities. The 112024 protein possesses a PFAM acyltransferase domain, from about aa 103 to about aa 227, as predicted by HMMer, Version 2.1.1.

The DGAT2 family member sequence hDC2 (SEQ ID NO:21), which is approximately 1093 nucleotides long including untranslated regions, contains a predicted methionine-initiated coding sequence of about 1004 nucleotides (nucleotides 49-1053 of SEQ ID NO:21) The coding sequence encodes a 334 amino acid protein (SEQ ID NO:22). The molecule may have transmembrane segments from amino acids (aa) 19-43, 131-151 and 209-227 as predicted by MEMSAT. Prosite program analysis was used to predict various sites within the hDC2 protein. N-glycosylation sites were predicted at aa 76-79, 120-123, 124-127, and 179-182. A cAMP and cGMP dependent protein kinase phosphorylation site was predicted at aa 69-72. Protein kinase C phosphorylation sites were predicted at aa 164-166, and 275-277. Casein kinase II phosphorylation sites were predicted at aa 225-228, and 307-310. N-myristoylation sites were predicted at aa 67-72, 116-121, 177-182, and 187-192. An amidation site was predicted at aa 67-70.

In one embodiment, a DGAT2 family member molecule may include a signal sequence. As used herein, a "signal sequence" refers to a peptide of about 10-80 amino acid residues in length which occurs at the N-terminus of secretory and integral membrane proteins and which contains a majority of hydrophobic amino acid residues. For example, a signal sequence contains at least about 20-60 amino acid residues, preferably about 30-50 amino acid residues, more preferably about 37 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in certain embodiments, a DGAT2 family member protein may contain a signal sequence of about amino acids 1-68 of SEQ ID NO:8, 1-65 of SEQ ID NO:20, 1-55 of SEQ ID NO:2, 1-55 of SEQ ID NO:4, 1-49 of SEQ ID NO:14, 1-58 of SEQ ID NO:18, or 1-63 of SEQ ID NO:22. The "signal sequence" is cleaved during processing of the mature protein. In such embodiments, the mature DGAT2 family member protein corresponds to amino acids acids 69-341 of SEQ ID NO:8, 66-337 of SEQ ID NO:20, 56-334 of SEQ ID NO:2, 56-284 of SEQ ID NO:4, 50-112023 of SEQ ID NO:14, 59-333 of SEQ ID NO:18, or 64-334 of SEQ ID NO:22.

Based on DGAT2 family member protein sequence, cellular localization signals can be identified by methods known to one of skill in the art (e.g., PSORT Prediction). Subcellular localization of a DGAT2 family member, generated using PSORT Prediction software. Predicted transmembrane domains may be identified by ORF analysis with MEMSAT.

For general information regarding PSORT, Prosite and PFAM identifiers, PS prefix and PF prefix domain identification numbers, refer to Sonnhammer et al. (1997) *Protein* 28:405-420.

The DGAT2 family member protein contains a significant number of structural characteristics in common with members of the acyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "diacylglyceroltransferase" or "DGAT" refers to a family of proteins that preferably comprise a membrane bound acyltransferase enzyme. Members of the DGAT2 family also share certain conserved amino acid residues, some of which may be determined to be critical to acyltransferase function triglyceride biosynthesis. For example, alignment of the human DGAT2 family members is depicted in Table 1 below.

TABLE 1

Sequence alignment of human DGAT2 family members

```
112037  (SEQ ID NO:62)  ..........  ..........  ..........  ..........  ..........
60489   (SEQ ID NO:8)   ..........  ..........  ..........  ..........  .......MGV
DC2     (SEQ ID NO:22)  ..........  ..........  ..........  ..........  ..........
112041  (SEQ ID NO:20)  ..........  ..........  ..........  ..........  ..........
112024  (SEQ ID NO:18)  ..........  ..........  ..........  ..........  ..........
112023  (SEQ ID NO:16)  ..........  ..........  ..........  ..........  ..........
86606   (SEQ ID NO:10)  MKTLIAAYSG  VLRGERQAEA  DRSQRSHGGP  ALSREGSGRW  GTGSSILSAL
58765s  (SEQ ID NO:4)   ..........  ..........  ..........  ..........  ..........
58765   (SEQ ID NO:2)   ..........  ..........  ..........  ..........  ..........

112037                  ..........  ..........  ..........  ..........  ..........
60489                   ATTLQPPTTS  KTLQKQHLEA  VGAYQYVLTF  LFMG.PFFSL  LVFVLLFTSL
DC2                     ..MKVEFAPL  NIQLARRLQT  VAVLQWVLSF  LTGP.MSIGI  TVMLIIHN.Y
112041                  .....MAFFS  RLNLQEGLQT  FFVLQWIPVY  IFLGAIPILL  IPYFLLFSKF
112024                  .....MLLPS  KKDLKTALDV  FAVFQWSFSA  LLITTTVIAV  NLYLVVFTPY
112023                  ......MAHS  KQ..PSHFQS  LMLLQWPLSY  LAIFWILQPL  FVYLL.FTSL
86606                   QDLFSVTWLN  RSKVEKQLQV  ISVLQWVLSF  LVLGVACSAI  LMYIF.CTDC
58765s                  ...MVEFAPL  FMPWERRLQT  LAVLQFVFSF  LALA.EICTV  GFIALLFTRF
58765                   ...MVEFAPL  FMPWERRLQT  LAVLQFVFSF  LALA.EICTV  GFIALLFTRF
```

TABLE 1-continued

Sequence alignment of human DGAT2 family members

```
112037                                                      ....LVKTAK
60489     WPFSVFYLVW LYVDWDTPNQ GGRRSEWIRN RAIWRQLRDY YPVKLVKTAE
DC2       LFLYIPYLMW LYFDWHTPER GGRRSSWIKN WTLWKHFKDY FPIHLIKTQD
112041    WPLAVLSLAW LTYDWNTHSQ GGRRSAWVRN WTLWKYFRNY FPVKLVKTHD
112024    WPVTVLILTW LAFDWKTPQR GGRRFTCVRH WRLWKHYSDY FPLKLLKTHD
112023    WPLPVLYFAW LFLDWKTPER GGRRSAWVRN WCVWTHIRDY FPITILKTKD
86606     WLIAVLYFTW LVFDWNTPKK GGRRSQWVRN WAVWRYFRDY FFIQLVKTHN
58765s    WLLTVLYAAW WYLDRDKPRQ GGRHIQAIRC WTIWKYMKDY FPISLVKTAE
58765     WLLTVLYAAW WYLDRDKPRQ GGRHIQAIRC WTIWKYMKDY FPISLVKTAE

112037    LGTSWNYLFD FHPHRVLVVG AFANFCTEPT GCSCLFPKLP PHLLMLPCWF
60489     LPPDRNYVLG AHPHGIMCTG FLCNFSTESM GFSQLFPGLR PWLAVLAGLF
DC2       LDPSHNYIFG FHPHGIMAVG AFGNFSVNYS DFKDLFPGFT SYLHVLPLWF
112041    LSPKHNYIIA NHPHGILSFG VPINFATEAT GIARIFPSIT PFVGTLERIF
112024    ICPSRNYILV CHPHGLFAHG WFGHFATEAS GFSKIFPGIT PYILTLGAFF
112023    LSPEHNYLMG VHPHGLLTFG AFCNFCTEAT GFSKTFPGIT PHLATLSWFF
86606     LLTTRNYIFG YHPHGIMGLG AFCNFSTEAT EVSKKFPGIR PYLATLAGNF
58765s    LDPSRNYIAG FHPHGVLAVG AFANLCTEST GFSSIFPGIR PHLMMPTLWF
58765     LDPSRNYIAG FHPHGVLAVG AFANLCTEST GFSSIFPGIR PHLMMLTLWF

112037    HLLFFQDYIM SGGLVSFVKA PLPQWWPGG. ...CP..GVG GPLQALEAKP
60489     YLPVYRDYIM SFGLCPVSRQ SLDFILSQPQ LGQAVVIMVG GAHEALYSVP
DC2       WCPVFREYVM SVGLVSVSKK SVSYMVSKEG GGNISVIVLG GAKESLDAHP
112041    WIPIVREYVM SMGVCPVSSS ALKYLLTQKG SGNAVVIVVG GAAEALLCRP
112024    WMPFLREYVM STGACSVSRS SIDFLLTHKG TGNMVIVVIG GLAECRYSLP
112023    KIPFVREYLM AKGVCSVSQP AINYLLSHG. TGNLVGIVVG GVGEALQSVP
86606     RMPVLREYLM SGGICPVSRD TIDYLLSKNG SGNAIIIVVG GAAESLSSMP
58765s    RAPFFRDYIM SAGLVTSEKE SAAHILNRKG GGNLLGIIVG GAQEALDARP
58765     RAPFFRDYIM SAGLVTSEKE SAAHILNRKG GGNLLGIIVG GAQEALDARP

112037    GQLSLPIRNQ KRLVKSALEL .......... GENELFQQFP NPQSSWVQRT
60489     GEHCLTLQKR KGFVRLALRH GASLVPVYSF GENDIFRLKA FATGSWQHWC
DC2       GKFTLFIRQR KGFVKIALTH GASLVPVVSF GENELFKQTD NPEGSWIRTV
112041    GASTLFLKQR KGFVKMALQT GAYLVPSYSF GENEVFNQET FPEGTWLRLF
112024    GSSTLVLKNR SGFVRMALQH GVPLIPAYAF GETDLYDQHI FTPGGFVNRF
112023    KTTTLILQKR KGFVRTALQH GAHLVPTFTF GETEVYDQVL FHKDSRMYKF
86606     GKNAVTLRNR KGFVKLALRH GADLVPIYSF GENEVYKQVI FEEGSWGRWV
58765s    GSFTLLLRNR KGFVRLALTH GYQASGKSTL G......SVG NWQG...FYF
58765     GSFTLLLRNR KGFVRLALTH GAPLVPIFSF GENDLFDQIP NSSGSWLRYI

112037    QEALRP.... LLSVALQLFL GRR......G LPLPFRAPIR TVVGSAIPVQ
60489     QLTFKK.... LMGFSPCIFW GRGLFSATSW GLLPFAVPIT TVVGRPIPVP
DC2       QNKLQK.... IMGFALPLFH ARG.VFQYNF GLMTYRKAIH TVVGRPIPVN
112041    QKTFQDTFKK ILGLNFCTFH GRG.FTRGSW GFLPFNRPIT TVVGEPLPIP
112024    QKWFQS.... MVHIYPCAFY GRG.FTKNSW GLLPYSRPVT TIVGEPLPMP
112023    QSCFRR.... IFGFYCCVFY GQS.FCQGST GLLPYSRPIV TVVGEPLPLP
86606     QKKFQK.... YIGFAPCIFH GRGLFSSDTW GLVPYSKPIT TVVGEPITIP
58765s    GGKMAE.... TNADSI.... .......... .LVEIFSPFT IKIIFWCLMP
58765     QNRLQK.... IMGISLPLFH GRG.VFQYSF GLIPYRRPIT TVVGKPIEVQ

112037    QSPPPSPAQV DTLQARYVGR LTQLFEEHQA RYGVPADRHL VLTEARPTAW PRLSAG
60489     QRLHPTEEEV NHYHALYMTA LEQLFEEHKE SCGVPASTCL TFI...... ......
DC2       QTLNPTQEQI EELHQTYMEE LRKLFEEHKG KYGIPEHETL VLK...... ......
112041    RIKRPNQKTV DKYHALYISA LRKLFDQHKV EYGLPETQEL TIT...... ......
112024    KIENPSQEIV AKYHTLYIDA LRKLFDQHKT KFGISETQEL EII...... ......
112023    QIEKPSQEMV DKYHALYMDA LDKLFDQHKT HYGCSETQKL FFL...... ......
86606     KLEHPTQQDI DLYHTMYMEA LVKLFDKHKT KFGLPETEVL EVN...... ......
58765s    KYLEKFP... ....QRRLSD LRN....... .......... .......... ......
58765     KTLHPSEEEV NQLHQRYIKE LCNLFEAHKL KFNIPADQHL EFC...... ......
```

The percent identity of the DGAT2 family members ranges from 33% identity (e.g., 112024 and 58765s share 33% identity) to 75% identity (e.g., 58765 short and long forms share 75% identity). The majority of the full length sequences share between 44% to 51% identity (e.g., 112041 and 60489; 112023 and 60489; as well as 86606 and 58765 share 44% identity; 112041 and 112024, 112041 and 112023, 112024 and 112023, 112023 and 86606 share 51% identy) over their entire lengths. The most closely related full length human family members are 58765 and DC2, which share 52% identity over their entire lengths.

In one embodiment, a DGAT2 family member protein includes at least one transmembrane domain. As used herein, the term "transmembrane domain" includes an amino acid sequence of about 15 amino acid residues in length that spans a phospholipid membrane. More preferably, a transmembrane domain includes about at least 16, 17, 18, 20, 21, 22, 23, or 24 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neuronsci.* 19: 235-63, the contents of which are incorporated herein by reference.

In a preferred embodiment, a DGAT2 family member polypeptide or protein has at least one transmembrane domain or a region which includes at least 16, 17, 18, 20, 21, 22, 23, or 24 amino acid residues and has at least about 60%, 70% 80% 90% 95%, 99%, or 100% homology with a "transmembrane domain," e.g., at least one transmembrane domain of human DGAT2 family member.

In another embodiment, a DGAT2 family member protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring DGAT2 family member, or DGAT2 family member-like protein.

In a preferred embodiment, a DGAT2 family member polypeptide or protein has a "non-transmembrane domain" or a region which includes at least about 1-100, preferably about 2-80, more preferably about 5-70, and even more preferably about 8-65 amino acid residues, and has at least about 60%, 70% 80% 90% 95%, 99% or 100% homology with a "non-transmembrane domain", e.g., a non-transmembrane domain of human DGAT2 family member. Preferably, a non-transmembrane domain is capable of catalytic activity.

As the DGAT2 family member polypeptides of the invention may modulate DGAT2 family member-mediated activities (e.g., triglyceride synthesis), they may be useful for developing novel diagnostic and therapeutic agents for DGAT2 family member-mediated or related disorders (e.g., obesity, triglyceride deficiency), as described below.

As used herein, a "DGAT2 family member activity", "biological activity of DGAT2 family member" or "functional activity of DGAT2 family member", refers to an activity exerted by a DGAT2 family member protein, polypeptide or nucleic acid molecule on e.g., a DGAT2 family member-responsive cell or on a DGAT2 family member substrate, e.g., a diacylglycerol substrate, as determined in vivo or in vitro. In one embodiment, a DGAT2 family member activity is a direct activity, such as an association with a DGAT2 family member target molecule. A "target molecule" or "binding partner" is a molecule with which a DGAT2 family member protein binds or interacts in nature (e.g., diacylglycerol, acyl-coA). A DGAT2 family member activity can also be an indirect activity, e.g., accumulation of fat stores as result of the DGAT2 family member activity.

The DGAT2 family member molecules of the present invention are predicted to have similar biological activities as DGAT2 family members. For example, the DGAT2 family member proteins of the present invention can have one or more of the following activities: (1) regulating, sensing and/or producing triglycerides in a cell, (for example, a fat cell (e.g., an adipocyte), a liver cell (e.g., a hepatocyte), a small intestine cell); (2) interacting with (e.g., binding to) a diglyceride molecule; (3) mobilizing an intracellular molecule that participates in a triglyceride biosynthesis (e.g., diacylglycerol or acyl-coA); (4) regulating diglyceride utilization; (5) altering the structure or components of a cell (e.g., and adipocyte); and (6) modulating cell proliferation; migration, cell differentiation; and cell survival. Thus, the DGAT2 family member molecules can act as novel diagnostic targets and therapeutic agents for controlling DGAT2 family member-related disorders (e.g., obesity and related disorders). Other activities, as described below, include the ability to modulate function, survival, morphology, proliferation and/or differentiation of cells of tissues in which DGAT2 family member molecules are expressed (e.g., adipocytes).

The response mediated by a DGAT2 family member receptor protein depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the protein, it is universal that the protein is a DGAT2 family member and interacts with substrate (e.g., acyl-coA, acylglycerol) to produce triacylglycerol in a cell. As used herein, a "triacylglycerol biosynthesis" or "triglyceride biosynthesis" refers to the modulation (e.g., stimulation or inhibition) of a cellular function/activity upon the binding of a substrate to the DGAT2 family member (DGAT2 family member protein). Examples of such functions include mobilization of lipid in adipocytes, production of fat stores.

Based on the above-described sequence similarities, the DGAT2 family member molecules of the present invention are predicted to have similar biological activities as diacylglycerol transferase family members. Thus, the DGAT2 family member molecules can act as novel diagnostic targets and therapeutic agents for controlling one or more of disorders associated with adipocyte differentiation and metabolism and metabolic disorders, cardiovascular disorders, liver disorders, cellular proliferative and/or differentiative disorders, or viral diseases.

The present invention is based, at least in part, on the discovery that the DGAT2 family member nucleic acid and polypeptide molecules are expressed at high levels in adipose, liver, small intestine tissue, are regulated during conditions which affect differentiation and metabolism of adipocytes, and are downregulated in genetic animal models of obesity (see Examples and Tables described herein). Without intending to be limited by mechanism, it is believed that DGAT2 family member molecules can modulate the metabolism by (directly or indirectly) affecting the rate of lipogenesis and/or lipolysis, and production and maintenance of fat storage in mammals.

As used herein, the term "metabolic disorder" includes a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of DGAT2 family member activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, diabetes (e.g., diabetes insipidus, diabetes mellitus (type I), diabetes mellitus (type II)), endocrine abnormalities, triglyceride storage disease, Bardet-Biedl syndrome, Lawrence-Moon syndrome, and Prader-Labhart-Willi syndrome. Obesity is defined as a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)). Additional metabolic disorders include lipid disorders (e.g., familial hypercholesteroliemia, polygenic hypercholesteroliemia, familial hypertriglyceridemia, familial lipoprotein lipase deficiency, combined hyperlipidemia, dysbetalipoproteinemia, sitosterolemia, Tangier disease, hypobetalipoproteinemia, lecithin:cholesterol acyltransferase (LCAT) deficiency, and cerebrotendinous xanthomatosis) and toxic and acquired metabolic diseases.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

As used herein, "liver disorders" which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, DGAT2 family member molecules can play an important role in the etiology of certain viral diseases, including but not limited to Hepatitis B, Hepatitis C and Herpes Simplex Virus (HSV). Modulators of DGAT2 family member activity could be used to control viral diseases. The modulators can be used in the treatment and/or diagnosis of viral infected tissue or virus-associated tissue fibrosis, especially liver and liver fibrosis. Also, DGAT2 family member modulators can be used in the treatment and/or diagnosis of virus-associated carcinoma, especially hepatocellular cancer.

As used interchangeably herein, "DGAT2 family member activity," "biological activity of DGAT2 family member" or "functional activity of DGAT2 family member," includes an activity exerted by a DGAT2 family member protein, polypeptide or nucleic acid molecule on a DGAT2 family member responsive cell or tissue, e.g., adipocytes, or on a DGAT2 family member protein substrate, e.g., diacylglycerol, as determined in vivo, or in vitro, according to standard techniques. DGAT2 family member-mediated function can include modulation of metabolism. Examples of such target molecules include proteins in the same biosynthetic path as the DGAT2 family member protein, e.g., proteins which may function upstream (including both stimulators and inhibitors of activity) or downstream of the DGAT2 family member protein in a pathway involving regulation of metabolism. The biological activities of DGAT2 family member proteins can have one or more of the following activities: 1) modulation of fat homeostasis; 2) modulation of lipogenesis (e.g., fat deposition necessary for heat insulation, mechanical cushion, and/or storage); 3) modulation of lipolysis (e.g., fat mobilization necessary as an energy source and/or for thermogenesis); and 4) modulation of adipocyte growth (e.g., hyperplastic and/or hypertrophic growth).

As used herein, "metabolic activity" includes an activity exerted by an adipose cell, or an activity that takes place in an adipose cell. For example, such activities include cellular processes that contribute to the physiological role of adipose cells, such as lipogenesis and lipolysis and include, but are not limited to, cell proliferation, differentiation, growth, migration, programmed cell death, uncoupled mitochondrial respiration, and thermogenesis.

The DGAT2 family member proteins, fragments thereof, and derivatives and other variants of the sequences in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62 are collectively referred to as "polypeptides or proteins of the invention" or "DGAT2 family member polypeptides or proteins". Nucleic acid molecules encoding such polypeptides or proteins are collectively referred to as "nucleic acids of the invention" or "DGAT2 family member nucleic acids." DGAT2 family member molecules refer to DGAT2 family member nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and non-aqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a DGAT2 family member protein, preferably a mammalian DGAT2 family member protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of DGAT2 family member protein having less than about 30%, 20%, 10% and more preferably 5% (by dry weight), of non-DGAT2 family member protein (also referred to herein as a "contaminating protein"), or of chemical precursors or non-DGAT2 family member chemicals. When the DGAT2 family member protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of DGAT2 family member(e.g., the sequence of SEQ ID NO:7, SEQ ID NO:19, or SEQ ID NO:61 without abolishing or more preferably, without substantially altering a biological activity, whereas an "essential" amino acid residue results in such a change. For example, amino acid residues that are conserved among the polypeptides of the present invention, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a DGAT2 family member protein is preferably replaced with another amino acid residue from the same side chain family. Alternatively, in another embodiment, mutations can be introduced randomly along all or part of a DGAT2 family member coding sequence, such as by saturation mutagenesis, and the resultant mutants can be screened for DGAT2 family member biological activity to identify mutants that retain activity. Following mutagenesis of a DGAT2 family member nucleotide sequence of the invention, the encoded protein can be expressed recombinantly and the activity of the protein can be determined.

As used herein, a "biologically active portion" of a DGAT2 family member protein includes a fragment of a DGAT2 family member protein which participates in an interaction between a DGAT2 family member molecule and a non-DGAT2 family member molecule. Biologically active portions of a DGAT2 family member protein include peptides comprising amino acid sequences sufficiently homologous to or derived from the amino acid sequence of the DGAT2 family member protein, e.g., the amino acid sequence shown in SEQ ID NO:8, SEQ ID NO:20, or SEQ ID NO:62 which include less amino acids than the full length DGAT2 family member proteins, and exhibit at least one activity of a DGAT2 family member protein. Typically, biologically active portions comprise a domain or motif with at least one activity of the DGAT2 family member protein, e.g., diacylglycerol acyltransferase activity. A biologically active portion of a DGAT2 family member protein can be a polypeptide which is, for example, 10, 25, 50, 100, 200 or more amino acids in length. Biologically active portions of a DGAT2 family member protein can be used as targets for developing agents which modulate a DGAT2 family member mediated activity, e.g., diacylglycerol acyltransferase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence amino acid residues are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990) *J. Mol. Biol.* 215:403-10. BLAST nucleotide searches can be performed with the NBLAST program, score=100, wordlength=12 to obtain nucleotide sequences homologous to DGAT2 family member nucleic acid molecules of the invention. BLAST protein searches can be performed with the XBLAST program, score=50, wordlength=3 to obtain amino acid sequences homologous to DGAT2 family member protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to an animal, e.g., a human, or a non-human mammal, e.g., a mouse, a rat, a primate, a horse, a cow, a goat, or other animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a DGAT2 family member polypeptide described herein, e.g., a full length DGAT2 family member protein or a fragment thereof, e.g., a biologically active portion of DGAT2 family member protein. Also included is a nucleic acid fragment suitable for use as a hybridization probe, which can be used, e.g., to a identify nucleic acid molecule encoding a polypeptide of the invention, DGAT2 family member mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:61 or a portion of any of these nucleotide sequences. In one embodiment, the nucleic acid molecule includes sequences encoding the DGAT2 family member protein (e.g., "the coding region", from nucleotides 154-1194 of SEQ ID NO:7, not including the terminal codon), as well as 5' untranslated sequences (nucleotides 1-153 of SEQ ID NO:7). Alternatively, the nucleic acid molecule can include only the coding region (e.g., nucleotides 154-1194 of SEQ ID NO:7) and, e.g., no flanking sequences which normally accompany the subject sequence. In another embodiment, the nucleic acid molecule encodes a sequence corresponding to the mature protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62.

In another embodiment, an isolated nucleic acid molecule of the invention includes a nucleic acid molecule which is a complement of the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61 or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, such that it can hybridize to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:61, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23 or SEQ ID NO:61. In the case of an isolated nucleic acid molecule which is longer than or equivalent in length to the reference sequence, e.g., SEQ ID NO:7, SEQ ID NO:19, the comparison is made with the full length of the reference sequence. Where the isolated nucleic acid molecule is shorter than the reference sequence (e.g., shorter than SEQ ID NO:7, SEQ ID NO:19, SEQ ID NO:61), the comparison is made to a segment of the reference sequence of the same length (excluding any loop required by the homology calculation).

DGAT2 Family Member Nucleic Acid Fragments

A nucleic acid molecule of the invention can include only a portion of the DGAT2 family member nucleic acid sequences of the invention (e.g., SEQ ID NO:7, SEQ ID NO:19, SEQ ID NO:61). For example, such a nucleic acid molecule can include a fragment which can be used as a probe or primer or a fragment encoding a portion of a DGAT2 family member protein, e.g., an immunogenic or biologically active portion of a DGAT2 family member protein. A fragment can comprise: nucleotides which encode a diacylglycerol acyltransferase domain of human DGAT2 family member. The nucleotide sequences determined from the cloning of the DGAT2 family member genes allows for the generation of probes and primers designed for use in identifying and/or cloning of additional DGAT2 family member family members, or fragments thereof, as well as additional DGAT2 family member homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include a diacylglycerol acyltransferase domain. In a preferred embodiment the fragment is at least, 50, 100, 200, 300, 400, 500, 600, 700, or 900 base pairs in length.

DGAT2 family member probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of the DGAT2 family member nucleic acid sequences of the invention (e.g., SEQ ID NO:7, SEQ ID NO:19, SEQ ID NO:61), or of a naturally occurring allelic variant or mutant of DGAT2 family member nucleic acid sequences of the invention (e.g., SEQ ID NO:7, SEQ ID NO:19, SEQ ID NO:61).

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes a diacylglycerol acyltransferase domain.

In another embodiment a set of primers is provided, e.g., primers suitable for use in a PCR, which can be used to amplify a selected region of a DGAT2 family member sequence, e.g., a region described herein. The primers should be at least 5, 10, or 50 base pairs in length and less than 100, or less than 200, base pairs in length. The primers should be identical, or differ by one base from a sequence disclosed herein or from a naturally occurring variant. E.g., primers suitable for amplifying all or a portion of any of the following regions or domains described herein are provided (e.g., a diacylglycerol acyltransferase domain).

A nucleic acid fragment can encode an epitope bearing region of a polypeptide described herein.

A nucleic acid fragment encoding a "biologically active portion of a DGAT2 family member polypeptide" can be prepared by isolating a portion of the nucleotide sequence of the DGAT2 family member sequences of the invention (e.g., SEQ ID NO:7, SEQ ID NO:19, SEQ ID NO:61), which encodes a polypeptide having a DGAT2 family member biological activity (e.g., the biological activities of the DGAT2 family member proteins as described herein), expressing the encoded portion of the DGAT2 family member protein (e.g., by recombinant expression in vitro) and assessing the activity of the encoded portion of the DGAT2 family member protein. For example, a nucleic acid fragment encoding a biologically active portion of DGAT2 family member includes a diacylglycerol acyltransferase domain. A nucleic acid fragment encoding a biologically active portion of a DGAT2 family member polypeptide, may comprise a nucleotide sequence which is greater than 300-1200 or more nucleotides in length.

In preferred embodiments, nucleic acids include a nucleotide sequence which is about 300, 400, 500, 600, 700, 800, 900, 1000, 1100, 1200, 1300, 1400 nucleotides in length and hybridizes under stringent hybridization conditions to a nucleic acid molecule of DGAT2 family member nucleic acid sequences of the invention (e.g., SEQ ID NO:7, SEQ ID NO:19, SEQ ID NO:61).

DGAT2 Family Member Nucleic Acid Variants

The invention further encompasses nucleic acid molecules that differ from the DGAT2 family member nucleotide sequences of the invention (e.g., SEQ ID NO:7, SEQ ID NO:19, SEQ ID NO:61). Such differences can be due to degeneracy of the genetic code (and result in a nucleic acid which encodes the same DGAT2 family member proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues of the DGAT2 family member protein sequences provided (e.g. SEQ ID NO:8, SEQ ID NO:20, SEQ ID NO:62). If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. E.g., the nucleic acid can be one in which at least one colon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of the nucleic acid sequences of the invention (e.g., SEQ ID NO:7, SEQ ID NO:19, SEQ ID NO:61), e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the amino acid sequences of the invention (e.g., SEQ ID NO:8, SEQ ID NO:20, SEQ ID NO:62) or a fragment of those sequences. Such nucleic acid molecules can readily be obtained as being able to hybridize under stringent conditions, to the nucleotide sequence shown in SEQ ID NO:7, SEQ ID NO:19, or SEQ ID NO:61 or a fragment of this sequence. Nucleic acid molecules corresponding to orthologs, homologs, and allelic variants of the DGAT2 family member cDNAs of the invention can further be isolated by mapping to the same chromosome or locus as the DGAT2 family member gene. Preferred variants include those that are correlated with diacylglycerol acyltransferase activity.

Allelic variants of DGAT2 family member, e.g., human DGAT2 family member, include both functional and non-functional proteins. Functional allelic variants are naturally occurring amino acid sequence variants of the DGAT2 family member protein within a population that maintain the ability to modulate the phosphorylation state of itself or another protein or polypeptide. Functional allelic variants will typically contain only conservative substitution of one or more amino acids of the DGAT2 family member amino acid sequences of the invention (e.g., SEQ ID NO:8 or SEQ ID NO:20 or SEQ ID NO:62), or substitution, deletion or insertion of non-critical residues in non-critical regions of the protein. Non-functional allelic variants are naturally-occurring amino acid sequence variants of the DGAT2 family member, e.g., human DGAT2 family member, protein within a population that do not have the ability to attach an acyl chain to a lipid precursor. Non-functional allelic variants will typically contain a non-conservative substitution, a deletion, or insertion, or premature truncation of the amino acid sequences of the invention (e.g., SEQ ID NO:8 or SEQ ID NO:20 or SEQ ID NO:62), or a substitution, insertion, or deletion in critical residues or critical regions of the protein.

Moreover, nucleic acid molecules encoding other DGAT2 family member family members and, thus, which have a nucleotide sequence which differs from the DGAT2 family member sequences of the invention (e.g., SEQ ID NO:7, SEQ ID NO:19 or SEQ ID NO:61) are intended to be within the scope of the invention.

Antisense Nucleic Acid Molecules, Ribozymes and Modified DGAT2 Family Member Nucleic Acid Molecules In another aspect, the invention features, an isolated nucleic acid molecule which is antisense to DGAT2 family member. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire DGAT2 family member coding strand, or to only a portion thereof (e.g., the coding region of human DGAT2 family member corresponding to DGAT2 family member sequences of the invention, e.g., SEQ ID NO:7 SEQ ID NO:19 or SEQ ID NO:61). In another embodiment, the antisense nucleic acid molecule is antisense to a "noncoding region" of the coding strand of a nucleotide sequence encoding DGAT2 family member (e.g., the 5' and 3' untranslated regions).

An antisense nucleic acid can be designed such that it is complementary to the entire coding region of DGAT2 family member mRNA, but more preferably is an oligonucleotide which is antisense to only a portion of the coding or noncoding region of DGAT2 family member mRNA. For example, the antisense oligonucleotide can be complementary to the region surrounding the translation start site of DGAT2 family member mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a DGAT2 family member protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) Nucleic Acids. Res. 15:6625-6641). The antisense nucleic acid molecule can also comprise a 2'-o-methylribonucleotide (Inoue et al., (1987) Nucleic Acids Res. 15:6131-6148) or a chimeric RNA-DNA analogue (Inoue et al., (1987) FEBS Lett. 215:327-330).

In still another embodiment, an antisense nucleic acid of the invention is a ribozyme. A ribozyme having specificity for a DGAT2 family member-encoding nucleic acid can include one or more sequences complementary to the nucleotide sequence of a DGAT2 family member cDNA disclosed herein (e.g., SEQ ID NO:7, SEQ ID NO:19 or SEQ ID NO:61), and a sequence having known catalytic sequence responsible for mRNA cleavage (see U.S. Pat. No. 5,093,246 or Haselhoff and Gerlach, (1988) Nature 334:585-591). For example, a derivative of a Tetrahymena L-19 IVS RNA can be constructed in which the nucleotide sequence of the active site is complementary to the nucleotide sequence to be cleaved in a DGAT2 family member-encoding mRNA. See, e.g., Cech et al. U.S. Pat. No. 4,987,071; and Cech et al. U.S. Pat. No. 5,116,742. Alternatively, DGAT2 family member mRNA can be used to select a catalytic RNA having a specific ribonuclease activity from a pool of RNA molecules. See, e.g., Bartel, D. and Szostak, J. W. (1993) Science 261:1411-1418.

DGAT2 family member gene expression can be inhibited by targeting nucleotide sequences complementary to the regulatory region of the DGAT2 family member (e.g., the DGAT2 family member promoter and/or enhancers) to form triple helical structures that prevent transcription of the DGAT2 family member gene in target cells. See generally, Helene, C., (1991) Anticancer Drug Des. 6(6):569-84; Helene, C. et al., (1992) Ann. N.Y. Acad. Sci. 660:27-36; and Maher, L. J., (1992) Bioassays 14(12):807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A DGAT2 family member nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., (1996) Bioorganic & Medicinal Chemistry 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al., (1996) supra; Perry-O'Keefe et al., Proc. Natl. Acad. Sci. 93: 14670-675.

PNAs of DGAT2 family member nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of DGAT2 family member nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., (1996) supra)); or as probes or primers for DNA sequencing or hybridization (Hyrup B. et al., (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al., (1989) *Proc. Natl. Acad. Sci. USA* 86:6553-6556; Lemaitre et al., (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., (1988) *Bio-Techniques* 6:958-976) or intercalating agents. (See, e.g., Zon, (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a DGAT2 family member nucleic acid of the invention, two complementary regions one having a fluorophore and one a quencher such that the molecular beacon is useful for quantitating the presence of the DGAT2 family member nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated DGAT2 Family Member Polypeptides

In another aspect, the invention features, an isolated DGAT2 family member protein, or fragment, e.g., a biologically active portion, for use as immunogens or antigens to raise or test (or more generally to bind) anti-DGAT2 family member antibodies. DGAT2 family member protein can be isolated from cells or tissue sources using standard protein purification techniques. DGAT2 family member protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, a DGAT2 family member polypeptide has one or more of the following characteristics:
it has the ability to regulate, sense and/or transmit an extracellular signal into a cell;
it has the ability to interact with (e.g., bind to) an extracellular signal or a cell surface receptor;
it has the ability to mobilize an intracellular molecule that participates in a signal transduction pathway (e.g., adenylate cyclase or phosphatidylinositol 4,5-bisphosphate (PIP$_2$), inositol 1,4,5-triphosphate (IP$_3$));
it has the ability to regulate polarization of the plasma membrane;
it has the ability to modulate cell proliferation, cell migration, differentiation and/or cell survival;
it has the ability to modulate function, survival, morphology, proliferation and/or differentiation of cells of tissues in which DGAT2 family member molecules are expressed;
it has a molecular weight (e.g., deduced molecular weight), amino acid composition or other physical characteristic of a DGAT2 family member protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or SEQ ID NO:62;
it has an overall sequence similarity (identity) of at least 60%, preferably at least 70%, more preferably at least 75, 80, 85, 86, 87, 88, 89, 90, 91, 92, 93, 94, 95, 96, 97, 98, 99% or more, with a polypeptide of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62;
it has an N-terminal domain which is preferably about 70%, 80%, 90%, 95%, 96%, 97%, 98%, 99% or higher, identical to a polypeptide of SEQ ID NO:2;
it has at least one transmembrane domains which is preferably about 70%, 80%, 90%, 95% or higher, identical to a polypeptide of SEQ ID NO:2;
it has a C-terminal domain which is preferably about 70%, 80%, 90%, 95%, 96%, 97%, 98%, 99% or higher, identical to a polypeptide of SEQ ID NO:2; or
it has an diacylglycerol acyltransferase domain which preferably has an overall sequence similarity of about 70%, 80%, 90% or 95% with amino acid residues 32-278 of SEQ ID NO:2.

In a preferred embodiment the DGAT2 family member protein, or fragment thereof, differs from the corresponding sequence in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the diacylglycerol acyltransferase domain. In another preferred embodiment one or more differences are in non-active site residues, e.g. outside of the diacylglycerol acyltransferase domain.

Other embodiments include a protein that contain one or more changes in amino acid sequence, e.g., a change in an amino acid residue which is not essential for activity. Such DGAT2 family member proteins differ in amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62, yet retain biological activity.

In one embodiment, a biologically active portion of a DGAT2 family member protein includes an diacylglycerol acyltransferase domain. In another embodiment, a biologically active portion of a DGAT2 family member protein includes a MttB family UPF0032 domain. Moreover, other biologically active portions, in which other regions of the protein are deleted, can be prepared by recombinant techniques and evaluated for one or more of the functional activities of a native DGAT2 family member protein.

In a preferred embodiment, the DGAT2 family member protein has an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62. In other embodiments, the DGAT2 family member protein is substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62 and retains the functional activity of the protein of SEQ ID NO:2, as described in detail above. Accordingly, in another embodiment, the DGAT2 family member protein is a protein which includes an amino acid sequence at least about 60%, 65%, 70%, 75%, 80%, 85%, 90%, 95%, 98% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:62.

DGAT2 Family Member Chimeric or Fusion Proteins

In another aspect, the invention provides DGAT2 family member chimeric or fusion proteins. As used herein, a DGAT2 family member "chimeric protein" or "fusion protein" includes a DGAT2 family member polypeptide linked to a non-DGAT2 family member polypeptide. A "non-DGAT2 family member polypeptide" refers to a polypeptide having an amino acid sequence corresponding to a protein which is not substantially homologous to the DGAT2 family member protein, e.g., a protein which is different from the DGAT2 family member protein and which is derived from the same or a different organism. The DGAT2 family member polypeptide of the fusion protein can correspond to all or a portion e.g., a fragment described herein of a DGAT2 family member amino acid sequence of the invention. In a preferred embodiment, a DGAT2 family member fusion protein includes at least one (or two) biologically active portion of a DGAT2 family member protein. The non-DGAT2 family member polypeptide can be fused to the N-terminus or C-terminus of the DGAT2 family member polypeptide.

The fusion protein can include a moiety which has a high affinity for a ligand. For example, the fusion protein can be a GST-DGAT2 family member fusion protein in which the DGAT2 family member sequences are fused to the C-terminus of the GST sequences. Such fusion proteins can facilitate the purification of a recombinant DGAT2 family member polypeptide. Alternatively, the fusion protein can be a DGAT2 family member protein containing a heterologous signal sequence at its N-terminus. In certain host cells (e.g., mammalian host cells), expression and/or secretion of DGAT2 family member can be increased through use of a heterologous signal sequence.

Fusion proteins can include all or a part of a serum protein, e.g., an IgG constant region, or human serum albumin.

The DGAT2 family member fusion proteins of the invention can be incorporated into pharmaceutical compositions and administered to a subject in vivo. The DGAT2 family member fusion proteins can be used to affect the bioavailability of a DGAT2 family member substrate. DGAT2 family member fusion proteins may be useful therapeutically for the treatment of disorders caused by, for example, (i) aberrant modification or mutation of a gene encoding a DGAT2 family member protein; (ii) mis-regulation of the DGAT2 family member gene; and (iii) aberrant post-translational modification of a DGAT2 family member protein.

Moreover, the DGAT2 family member-fusion proteins of the invention can be used as immunogens to produce anti-DGAT2 family member antibodies in a subject, to purify DGAT2 family member ligands and in screening assays to identify molecules which inhibit the interaction of DGAT2 family member with a DGAT2 family member substrate.

Expression vectors are commercially available that already encode a fusion moiety (e.g., a GST polypeptide). A DGAT2 family member-encoding nucleic acid can be cloned into such an expression vector such that the fusion moiety is linked in-frame to the DGAT2 family member protein.

Variants of DGAT2 Family Member Proteins

In another aspect, the invention also features a variant of a DGAT2 family member polypeptide, e.g., which functions as an agonist (mimetics) or as an antagonist. Variants of the DGAT2 family member proteins can be generated by mutagenesis, e.g., discrete point mutation, the insertion or deletion of sequences or the truncation of a DGAT2 family member protein. An agonist of the DGAT2 family member proteins can retain substantially the same, or a subset, of the biological activities of the naturally occurring form of a DGAT2 family member protein (e.g., diacylglycerol acyltransferase activity). An antagonist of a DGAT2 family member protein can inhibit one or more of the activities of the naturally occurring form of the DGAT2 family member protein by, for example, competitively modulating a DGAT2 family member-mediated activity of a DGAT2 family member protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the DGAT2 family member protein.

Variants of a DGAT2 family member protein can be identified by screening combinatorial libraries of mutants, e.g., truncation mutants, of a DGAT2 family member protein for agonist or antagonist activity.

Libraries of fragments e.g., N terminal, C terminal, or internal fragments, of a DGAT2 family member protein coding sequence can be used to generate a variegated population of fragments for screening and subsequent selection of variants of a DGAT2 family member protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a technique which enhances the frequency of functional mutants in the libraries, can be used in combination with the screening assays to identify DGAT2 family member variants (Arkin and Yourvan, (1992) *Proc. Natl. Acad. Sci. USA* 89:7811-7815; Delgrave et al., (1993) *Protein Engineering* 6(3):327-331).

Cell based assays can be exploited to analyze a variegated DGAT2 family member library. For example, a library of expression vectors can be transfected into a cell line, e.g., a cell line, which ordinarily responds to DGAT2 family member in a substrate-dependent manner. The transfected cells are then contacted with DGAT2 family member and the effect of the expression of the mutant on signaling by the DGAT2 family member substrate can be detected, e.g., by measuring diacylglycerol acyltransferase activity. Plasmid DNA can then be recovered from the cells which score for inhibition, or alternatively, potentiation of signaling by the DGAT2 family member substrate, and the individual clones further characterized.

In another aspect, the invention features a method of making a DGAT2 family member polypeptide, e.g., a peptide having a non-wild type activity, e.g., an antagonist, agonist, or super agonist of a naturally occurring DGAT2 family member polypeptide, e.g., a naturally occurring DGAT2 family member polypeptide. The method includes: altering the sequence of a DGAT2 family member polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a DGAT2 family member polypeptide having a biological activity of a naturally occurring DGAT2 family member polypeptide. The method includes: altering the sequence, e.g., by substitution or deletion of one or more residues, of a DGAT2 family member polypeptide, e.g., altering the sequence of a non-conserved region, or a domain or residue described herein, and testing the altered polypeptide for the desired activity.

Anti-DGAT2 Family Member Antibodies

In another aspect, the invention provides an anti-DGAT2 family member antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length DGAT2 family member protein or, antigenic peptide fragment of DGAT2 family member can be used as an immunogen or can be used to identify anti-DGAT2 family member antibodies made with other immunogens, e.g., cells, membrane preparations, and the like. The antigenic peptide of DGAT2 family member should include at least 8 amino acid residues of a DGAT2 family member amino acid sequence of the invention (e.g., the amino acid sequence shown in SEQ ID NO:8 or SEQ ID NO:20 or SEQ ID NO:62) and encompasses an epitope of DGAT2 family member. Preferably, the antigenic peptide includes at least 10 amino acid residues, more preferably at least 15 amino acid residues, even more preferably at least 20 amino acid residues, and most preferably at least 30 amino acid residues.

Fragments of DGAT2 family member polypeptides of the invention can be, e.g., as immunogens, or used to characterize the specificity of an antibody or antibodies against what are believed to be hydrophilic regions of the DGAT2 family member protein. Similarly, a fragment of DGAT2 family member proteins of the invention can be used to make an antibody against what is believed to be a hydrophobic region of the DGAT2 family member protein; a fragment of DGAT2 family can be used to make an antibody against a diacylglycerol acyltransferase region of the DGAT2 family member protein.

Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of DGAT2 family member are located on the surface of the protein, e.g., hydrophilic regions, as well as regions with high antigenicity. For example, an Emini surface probability analysis of the human DGAT2 family member protein sequence can be used to indicate the regions that have a particularly high probability of being localized to the surface of the DGAT2 family member protein and are thus likely to constitute surface residues useful for targeting antibody production. Methods to determine Emini surface probability analysis or other methods to determine immunogenic peptides of the DGAT2 family member amino acid sequences of the invention are known in the art.

In a preferred embodiment an antibody binds an epitope on any domain or region of any of the DGAT2 family member proteins described herein.

Chimeric, humanized, but most preferably, completely human antibodies are desirable for applications which include repeated administration, e.g., therapeutic treatment (and some diagnostic applications) of human patients.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

The anti-DGAT2 family member antibody can be a single chain antibody. A single-chain antibody (scFV) may be engineered (see, for example, Colcher, D. et al., *Ann. NY Acad. Sci.* 1999 Jun. 30;880:263-80; and Reiter, Y., *Clin. Cancer Res.* 1996 February; 2(2):245-52). The single chain antibody can be dimerized or multimerized to generate multivalent antibodies having specificities for different epitopes of the same target DGAT2 family member protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An anti-DGAT2 family member antibody (e.g., monoclonal antibody) can be used to isolate DGAT2 family member proteins or complexes by standard techniques, such as affinity chromatography or immunoprecipitation. Moreover, an anti-DGAT2 family member antibody can be used to detect DGAT2 family member protein (e.g., in a cellular lysate or cell supernatant) in order to evaluate the abundance and pattern of expression of the protein. Anti-DGAT2 family member antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a DGAT2 family member nucleic acid of the invention in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., DGAT2 family member proteins, mutant forms of DGAT2 family member proteins, fusion proteins, and the like).

The recombinant expression vectors of the invention can be designed for expression of DGAT2 family member proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S., (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in DGAT2 family member activity assays, (e.g., direct assays or competitive assays described in detail below), or to generate antibodies specific for DGAT2 family member protein(s). In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in E. coli is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The DGAT2 family member expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., (1987) *Genes Dev.* 1:268-277), lymphoid-specific promoters (Calame and Eaton, (1988) *Adv. Immunol.* 43:235-275), in particular promoters of T cell receptors (Winoto and Baltimore, (1989) *EMBO J.* 8:729-733) and immunoglobulins (Banerji et al., (1983) *Cell* 33:729-740; Queen and Baltimore, (1983) *Cell* 33:741-748), neuron-specific promoters (e.g., the neurofilament promoter; Byrne and Ruddle, (1989) *Proc. Natl. Acad. Sci. USA* 86:5473-5477), pancreas-specific promoters (Edlund et al., (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, (1990) *Science* 249:374-379) and the α-fetoprotein promoter (Campes and Tilghman, (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect the invention provides a host cell which includes a nucleic acid molecule described herein, e.g., a DGAT2 family member nucleic acid molecule within a recombinant expression vector or a DGAT2 family member nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a DGAT2 family member protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a DGAT2 family member protein. Accordingly, the invention further provides methods for producing a DGAT2 family member protein using the host cells of the invention. In one embodiment, the method includes culturing the host cell of the invention (into which a recombinant expression vector encoding a DGAT2 family member protein has been introduced) in a suitable medium such that a DGAT2 family member protein is produced. In another embodiment, the method further includes isolating a DGAT2 family member protein from the medium or the host cell.

In another aspect, the invention features, a cell or purified preparation of cells which include a DGAT2 family member transgene, or which otherwise misexpress one or more DGAT2 family member molecules. The cell preparation can consist of human or non-human cells, e.g., rodent cells, e.g., mouse or rat cells, rabbit cells, or pig cells. In preferred embodiments, the cell or cells include a DGAT2 family member transgene, e.g., a heterologous form of a DGAT2 family member, e.g., a gene derived from humans (in the case of a non-human cell). The DGAT2 family member transgene can be misexpressed, e.g., overexpressed or underexpressed. In other preferred embodiments, the cell or cells include a gene which misexpress an endogenous DGAT2 family member, e.g., a gene the expression of which is disrupted, e.g., a knockout. Such cells can serve as a model for studying disorders which are related to mutated or mis-expressed DGAT2 family member alleles or for use in drug screening.

In another aspect, the invention features, a human cell, e.g., a hematopoietic stem cell, transformed with nucleic acid which encodes a subject DGAT2 family member polypeptide.

Also provided are cells or a purified preparation thereof, e.g., human cells, in which an endogenous DGAT2 family member is under the control of a regulatory sequence that does not normally control the expression of the endogenous DGAT2 family member gene. The expression characteristics of an endogenous gene within a cell, e.g., a cell line or microorganism, can be modified by inserting a heterologous DNA regulatory element into the genome of the cell such that the inserted regulatory element is operably linked to the endogenous DGAT2 family member gene. For example, an endogenous DGAT2 family member gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published on May 16, 1991.

Transgenic Animals

The invention provides non-human transgenic animals. Such animals are useful for studying the function and/or activity of a DGAT2 family member protein and for identifying and/or evaluating modulators of DGAT2 family member activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous DGAT2 family member gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a DGAT2 family member protein to particular cells. A transgenic founder animal can be identified based upon the presence of a DGAT2 family member transgene in its genome and/or expression of DGAT2 family member mRNA in tissues or cells of the animals. A transgenic founder animal can then be used to breed additional animals carrying the transgene. Moreover, transgenic animals carrying a transgene encoding a DGAT2 family member protein can further be bred to other transgenic animals carrying other transgenes.

DGAT2 family member proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). In particularly preferred embodiments, the compositions provided herein are used in conjunction with methods of diagnosis and treatment of metabolic disorders (e.g., obesity, hyperlipidemia, diabetes), as well as cardiovascular and liver disorders.

The isolated nucleic acid molecules of the invention can be used, for example, to express a DGAT2 family member protein (e.g., via a recombinant expression vector in a host cell in gene therapy applications), to detect a DGAT2 family member mRNA (e.g., in a biological sample such as adipose tissue) or a genetic alteration in a DGAT2 family member gene, and to modulate DGAT2 family member activity, as described further below. The DGAT2 family member proteins can be used to treat disorders characterized by insufficient or excessive production of a DGAT2 family member substrate or production of DGAT2 family member inhibitors (e.g., an obesity disorder). In addition, the DGAT2 family member proteins can be used to screen for naturally occurring DGAT2 family member substrates, to screen for drugs or compounds which modulate DGAT2 family member activity, as well as to treat disorders characterized by insufficient or excessive production of DGAT2 family member protein or production of DGAT2 family member protein forms which have decreased, aberrant or unwanted activity compared to DGAT2 family member wild-type protein. Such disorders include those characterized by aberrant signaling or aberrant, e.g., hyperproliferative, cell growth. Moreover, the anti-DGAT2 family member antibodies of the invention can be used to detect and isolate DGAT2 family member proteins, regulate the bioavailability of DGAT2 family member proteins, and modulate DGAT2 family member activity.

A method of evaluating a compound for the ability to interact with, e.g., bind, a subject DGAT2 family member polypeptide is provided. The method includes: contacting the compound with the subject DGAT2 family member polypeptide; and evaluating ability of the compound to interact with, e.g., to bind or form a complex with the subject DGAT2 family member polypeptide. This method can be performed in vitro, e.g., in a cell free system, or in vivo, e.g., in a two-hybrid interaction trap assay. This method can be used to identify naturally occurring molecules which interact with subject DGAT2 family member polypeptide. It can also be used to find natural or synthetic inhibitors of subject DGAT2 family member polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to DGAT2 family member proteins, have a stimulatory or inhibitory effect on, for example, DGAT2 family member expression or DGAT2 family member activity, or have a stimulatory or inhibitory effect on, for example, the expression or activity of a DGAT2 family member substrate. Compounds thus identified can be used to modulate the activity of target gene products (e.g., DGAT2 family member genes) in a therapeutic protocol, to elaborate the biological function of the target gene product, or to identify compounds that disrupt normal target gene interactions.

The enzyme reaction catalyzed by (DGATs) involves the coupling of an acyl-CoA to a preformed diacylglycerol producing one equivalent of Coenzyme A (CoA) and triacylglycerol. Assays for DGAT activity are known in the art and can include, but are not limited to, direct detection of the products (Coenzyme A or triacylglycerol) or detection in the consumption of the substrates (diacylglycerol or acyl-CoA). Previous DGAT assays have focused on generation of a radiolabeled triacylglycerol using either a radiolabeled diacylglycerol or acyl-CoA starting material. (Lardizabal, K. K., Mai, J. T., Wagner, N. W., Wyrick, A., Voelker, T., and Hawkins, D. J. *J. Biol. Chem.* 276 (2001) 38862-38869; Cases, S., Stone, S. J., Zhou, P., Yen, E., Tow, B., Lardizabal, K. D., Voelker, T., and Farese Jr., R. V. *J. Biol. Chem.* 276 (2001) 38870-38876). This is a laborious procedure involving organic extractions and separations that are not rigorously quantitative for accurate kinetic characterization of the enzyme. This procedure can be extended to a more quantitative assay wherein an aqueous reaction with radiolabeled substrate (either acyl- CoA or diacylglycerol) is followed by separation and detection using radiometric HPLC. This will allow for separation and detection of the various reaction components (as TLC does) but allow for accurate quantitation of the various reaction species. However, this approach is not amenable to high-throughput screening.

Matrix-assisted laser desorption/ionization time-of-flight mass spectrometry (MALDI-TOF) and liquid chromatography/mass spectrometry (LC/MS) are very sensitive techniques that do not require the use of radiolabled substrates. This has been previously employed for detection of triacylglycerols. (Hlongwane, C., Delves, I. G., Wan, L. W., and Ayorinde, F. O. *Rapid Commun. Mass Spectrom.* 15 (2001) 2027-2034; Ayorinde, F. O., Keith Jr. Q. L., and Wan, L. W. *Rapid Commun. Mass Spectrom.* 13 (199) 1762-1769; Byrdwell, W. C., Emken, E. A., Neff, W. E., Adlof, R. O. *Lipids.* 31 (1996) 919-935). These and related techniques will allow for quantitation of every component in the DGAT reaction.

In one aspect, a high-throughput assay for monitoring the DGAT assay relies on detection of the free thiol generated in the form of CoA. Dithiobis-(2-nitro-5-thiobenzoic acid) (DTNB) has been employed for monitoring the reaction of numerous acyltransferases including monoacylglycerol acyltransferases (MGATs). (Bierbach, H. *Digestion.* 28 (1983) 138-147). Alternatively, fluorescent thiol substrates may be utilized in assays and detected using standard fluorescent detection methods known in the art. One example of detection includes using ThioGlo (NovaBiochem). Storey, B. T., et al. 1998. Mol. Reprod. Dev. 49, 400; Wright, S. K., and Viola, R. E. 1998. Anal. Biochem. 265, 8; and Langmuir, M. E., et al. 1996. in Fluorescence Microscopy and Fluorescent Probes (Slavic, J., ed.) pp. 229-233, Plenum Press, New York.

In yet another aspect, a high throughput assay for monitoring the DGAT assay relies on detection of product generated using fluorescence resonance energy transfer (FRET) analysis. In this method, substrates (acyl coA and diacylglycerol) are each measured with an appropriate fluorophore. Formation of the resulting triglyceride may be monitored using standard FRET analysis procedures. See, e.g., Stryer L, Haugland R P. Proc Natl Acad Sci USA 58, 719-726 (1967); and Selvin P R. Methods Enzymol 246, 300-334 (1995).

These approaches would be amenable to high-throughput screening as well as continuous assays for kinetic characterization and determination of inhibitory activity by small molecule inhibitors.

In another aspect, a high-throughput assay for monitoring the DGAT assay relies on detection of triacylglycerol product generated as a result of DGAT enzyme activity. In this method, scintillation proximity assay (SPA) technology may be utilized to monitor the acyltransferase reaction. In this method, one substrate is biotinylated (e.g., a biotinylated fatty-acyl-CoA) and combined in the reaction with radiolabeled second substrate (e.g., radiolabeled diacylglyceride, e.g., Diolein). In one aspect the biotinylated substrate can be a donor fatty acyl coA, and the radiolabeled substrate can be a radiolabeled acceptor diacylglycerol. In another aspect, the biotinylated substrate can be a biotinylated acceptor diacylglycerol and the radiolabeled second substrate can be a radiolabeled donor fatty acyl coA. Either combination may be used, and optimized to suit conditions. Either combination of substrates result in generation of a biotinylated, radiolabeled product triacylglycerol. Upon completion of the enzyme assay, product triacylglycerol generation can be determined using standard techniques for collection of biotinylated product and detection of fluorescence (e.g., SPA technology; avidin coated plates and traditional radiometric detection). The SPA beads are a preferred method of detection in many instances, as the SPA bead (Amersham) has both avidin and a scintillant covalently attached such that when radiolabeled biotinylated substrate attaches to the beads, the isotope is already in close proximity to the scintillant, thus making the addition of scintillation fluid unnecessary. This also means that only those molecules bound to the beads represent the radioactivity of the resulting product.

As described above, this assay can be utilized to monitor an acyltransferase reaction where either the donor acyl-CoA is biotinylated and the acceptor is radiolabeled; or a reaction where the donor is radiolabeled and the acceptor is biotinylated. Thus, the present assay may be useful to monitor any acyltransferase activity in which substrates are amenable to labeling in a similar manner. Thus the present assay is applicable to each of the DGAT2 family members described herein, and may also be applied to other acyltransferase enzymes (e.g., DGAT1). The present assay has advantages over art recognized methods of detection: the product can be captured through utilization of the biotin label (e.g., on a SPA bead) rather than laborious organic extractions; radiolabel sensitivity assay is much higher than detection of the fluorescent free CoA released; and the present methods are adaptable to high throughput screening as well as continuous assays for kinetic characterization and determination of inhibitory activity by small molecule inhibitors. Examples of the substrates and product reaction include:

Biotinylated Donor with Radiolabeled Acceptor

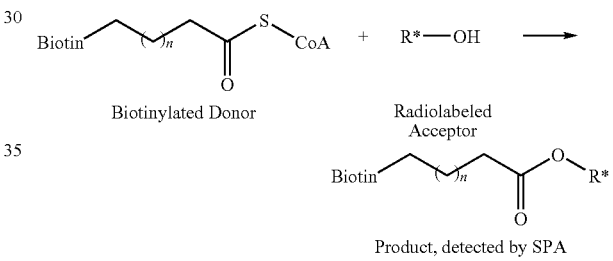

Biotinylated Acceptor with Radiolabeled Donor

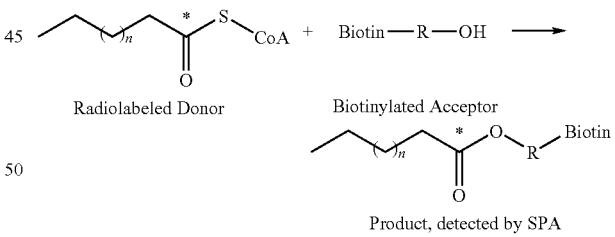

In one embodiment, the invention provides assays for screening candidate or test compounds which are substrates of a DGAT2 family member protein or polypeptide or a biologically active portion thereof. In another embodiment, the invention provides assays for screening candidate or test compounds which bind to or modulate the activity of a DGAT2 family member protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al., *J. Med. Chem.* 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al., (1994) *Proc. Natl. Acad. Sci. USA* 91:11422; Zuckermann et al., (1994). *J. Med. Chem.* 37:2678; Cho et al., (1993) *Science* 261:1303; Carrell et al., (1994) *Angew. Chem. Int. Ed. Engl.* 33:2059; Carell et al., (1994) *Angew. Chem. Int. Ed. Engl.* 33:2061; and in Gallop et al., (1994) *J. Med. Chem.* 37:1233.

Libraries of compounds may be presented in solution (e.g., Houghten, (1992) *Biotechniques* 13:412-421), or on beads (Lam, (1991) *Nature* 354:82-84), chips (Fodor, (1993) *Nature* 364:555-556), bacteria or spores (Ladner, U.S. Pat. No. 5,223,409), plasmids (Cull et al., (1992) *Proc. Natl. Acad. Sci. USA* 89:1865-1869) or on phage (Scott and Smith, (1990) *Science* 249:386-390); (Devlin, (1990) *Science* 249:404-406); (Cwirla et al., (1990) *Proc. Natl. Acad. Sci.* 87:6378-6382); (Felici, (1991) *J. Mol. Biol.* 222:301-310); (Ladner supra.).

Preferred libraries of compounds for the screening methods of the invention include small molecule compounds based on natural substrates for the DGAT2 family members of the invention (e.g., acyl-CoA, diacylglycerol). Generation of small molecules and analogs based on the substrates can be produced using methods described in the references cited above, in combination with additional methods and skills known to one in the art.

In one embodiment, an assay is a cell-based assay in which a cell which expresses a DGAT2 family member protein or biologically active portion thereof is contacted with a test compound, and the ability of the test compound to modulate DGAT2 family member activity is determined. Determining the ability of the test compound to modulate DGAT2 family member activity can be accomplished by monitoring, for example, diacylglycerol acyltransferase activity. The cell, for example, can be of mammalian origin, e.g., human. Cell homogenates, or fractions, preferably membrane containing fractions, including microsomes, can also be tested.

The ability of the test compound to modulate DGAT2 family member binding to a compound, e.g., a DGAT2 family member substrate, or to bind to DGAT2 family member can also be evaluated. This can be accomplished, for example, by coupling the compound, e.g., the substrate, with a radioisotope or enzymatic label such that binding of the compound, e.g., the substrate, to DGAT2 family member can be determined by detecting the labeled compound, e.g., substrate, in a complex. Alternatively, DGAT2 family member could be coupled with a radioisotope or enzymatic label to monitor the ability of a test compound to modulate DGAT2 family member binding to a DGAT2 family member substrate in a complex. For example, compounds (e.g., DGAT2 family member substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a DGAT2 family member substrate) to interact with DGAT2 family member with or without the labeling of any of the interactants can be evaluated. For example, interaction of a compound with DGAT2 family member without the labeling of either the compound or the DGAT2 family member can be measured by the change in the amount of triacylglycerol synthesis in response to contact of a compound. Changes in this triacylglycerol synthesis rate can be used as an indicator of the interaction between a compound and DGAT2 family member.

In yet another embodiment, a cell-free assay is provided in which a DGAT2 family member protein or biologically active portion thereof is contacted with a test compound and the ability of the test compound to bind to the DGAT2 family member protein or biologically active portion thereof is evaluated. Preferred biologically active portions of the DGAT2 family member proteins to be used in assays of the present invention include fragments which participate in interactions with non-DGAT2 family member molecules, e.g., fragments with high surface probability scores, fragments which interact with substrates of DGAT2 family members.

Soluble and/or membrane-bound forms of isolated proteins (e.g., DGAT2 family member proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block diacylglycerol acyltransferase activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the DGAT2 family member protein to bind to a target molecule can be accomplished using real-time Biomolecular Interaction Analysis (BIA) (see, e.g., Sjolander, S. and Urbaniczky, C., (1991) *Anal. Chem.* 63:2338-2345 and Szabo et al., (1995) *Curr. Opin. Struct. Biol.* 5:699-705). "Surface plasmon resonance" or "BIA" detects biospecific interactions in real time, without labeling any of the interactants (e.g., BIA-core). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either DGAT2 family member, an anti-DGAT2 family member antibody or its target molecule to facilitate separation of complexed from uncomplexed forms of one or both of the proteins, as well as to accommodate automation of the assay. Binding of a test compound to a DGAT2 family member protein, or interaction of a DGAT2 family member protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/DGAT2 family member fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or DGAT2 family member protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of DGAT2 family member binding or activity determined using standard techniques.

Other techniques for immobilizing either a DGAT2 family member protein or a target molecule on matrices include using conjugation of biotin and streptavidin. Biotinylated DGAT2 family member protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with DGAT2 family member protein or target molecules but which do not interfere with binding of the DGAT2 family member protein to its target molecule. Such antibodies can be derivatized to the wells of the plate, and unbound target or DGAT2 family member protein trapped in the wells by antibody conjugation. Methods for detecting such complexes, in addition to those described above for the GST-immobilized complexes, include immunodetection of complexes using antibodies reactive with the DGAT2 family member protein or target molecule, as well as enzyme-linked assays which rely on detecting an enzymatic activity associated with the DGAT2 family member protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 August; 18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J. Mol. Recognit.* 1998 Winter; 11(16):141-8; Hage, D. S., and Tweed, S. A., *J. Chromatogr. B Biomed. Sci. Appl.* 1997 Oct. 10;699(1-2):499-525). Further, fluorescence energy transfer may also be conveniently utilized, as described herein, to detect binding without further purification of the complex from solution.

In a preferred embodiment, the assay includes contacting the DGAT2 family member protein or biologically active portion thereof with a known compound which binds DGAT2 family member (e.g., substrate, e.g., acyl-coA, diacylglycerol) to form an assay mixture, contacting the assay mixture with a test compound, and determining the ability of the test compound to interact with a DGAT2 family member protein, wherein determining the ability of the test compound to interact with a DGAT2 family member protein includes determining the ability of the test compound to preferentially bind to DGAT2 family member or biologically active portion thereof, or to modulate the activity of a target molecule, as compared to the known compound (e.g., acyl-coA, diacylglycerol).

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the DGAT2 family member genes herein identified. In an alternative embodiment, the invention provides methods for determining the ability of the test compound to modulate the activity of a DGAT2 family member protein through modulation of the activity of a downstream effector of a DGAT2 family member target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, e.g., acyl-coA, diacylglycerol, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the DGAT2 family member proteins can be used as "bait proteins" in a two-hybrid assay or three-hybrid assay (see, e.g., U.S. Pat. No. 5,283,317; Zervos et al., (1993) *Cell* 72:223-232; Madura et al., (1993) *J. Biol. Chem.* 268:12046-12054; Bartel et al., (1993) *Biotechniques* 14:920-924; Iwabuchi et al., (1993) *Oncogene* 8:1693-1696; and Brent WO94/10300), to identify other proteins, which bind to or interact with DGAT2 family member ("DGAT2 family member-binding proteins" or "DGAT2 family member-bp") and are involved in DGAT2 family member activity. Such DGAT2 family member-bps can be activators or inhibitors of signals by the DGAT2 family member proteins or DGAT2 family member targets as, for example, downstream elements of a DGAT2 family member-mediated signaling pathway.

The two-hybrid system is based on the modular nature of most transcription factors, which consist of separable DNA-binding and activation domains. Briefly, the assay utilizes two different DNA constructs. In one construct, the gene that codes for a DGAT2 family member protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: DGAT2 family member protein can be the fused to the activator domain.) If the "bait" and the "prey" proteins are able to interact, in vivo, forming a DGAT2 family member-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the DGAT2 family member protein.

In another embodiment, modulators of DGAT2 family member expression are identified. For example, a cell or cell free mixture is contacted with a candidate compound and the expression of DGAT2 family member mRNA or protein evaluated relative to the level of expression of DGAT2 family member mRNA or protein in the absence of the candidate compound. When expression of DGAT2 family member mRNA or protein is greater in the presence of the candidate compound than in its absence, the candidate compound is identified as a stimulator of DGAT2 family member mRNA or protein expression. Alternatively, when expression of DGAT2 family member mRNA or protein is less (statistically significantly less) in the presence of the candidate compound than in its absence, the candidate compound is identified as an inhibitor of DGAT2 family member mRNA or protein expression. The level of DGAT2 family member mRNA or protein expression can be determined by methods described herein for detecting DGAT2 family member mRNA or protein.

In another aspect, the invention pertains to a combination of two or more of the assays described herein. For example, a modulating agent can be identified using a cell-based or a cell free assay, and the ability of the agent to modulate the activity of a DGAT2 family member protein can be confirmed in vivo, e.g., in an animal.

In another aspect, the methods may be combined and/or a single method may be used comparatively with various DGAT2 family members of the invention in order to identify selective inhibitors of one or more DGAT2 family members of the invention. Utilization of such combination/comparative assays will allow for the identification of selective inhibition of particular DGAT2 family member function which may be uniquely affected in one or more tissues and or disease states.

This invention further pertains to novel agents identified by the above-described screening assays. Accordingly, it is within the scope of this invention to further use an agent identified as described herein (e.g., a DGAT2 family member modulating agent, an antisense DGAT2 family member nucleic acid molecule, a DGAT2 family member-specific antibody, or a DGAT2 family member-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate one or more DGAT2 family member family members with a disease; (ii) identify an individual from a minute biological sample (tissue typing); and (iii) aid in forensic identification of a biological sample. These applications are described in the subsections below.

Chromosome Mapping

The DGAT2 family member nucleotide sequences or portions thereof can be used to map the location of the DGAT2 family member genes on a chromosome. This process is called chromosome mapping. Chromosome mapping is useful in correlating the DGAT2 family member sequences with genes associated with disease.

Briefly, DGAT2 family member genes can be mapped to chromosomes by preparing PCR primers (preferably 15-25 bp in length) from the DGAT2 family member nucleotide sequences. These primers can then be used for PCR screening of somatic cell hybrids containing individual human chromosomes. Only those hybrids containing the human gene corresponding to the DGAT2 family member sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al., (1983) *Science* 220:919-924).

Other mapping strategies e.g., in situ hybridization (described in Fan, Y. et al., (1990) *Proc. Natl. Acad. Sci. USA*, 87:6223-27), pre-screening with labeled flow-sorted chromosomes, and pre-selection by hybridization to chromosome specific cDNA libraries can be used to map DGAT2 family member to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al., (1987) *Nature*, 325:783-787.

Moreover, differences in the DNA sequences between individuals affected and unaffected with a disease associated with the DGAT2 family member gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

DGAT2 family member sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the DGAT2 family member nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:7 or SEQ ID NO:19 or SEQ ID NO:61 can provide positive individual identification with a panel of perhaps 10 to 1,000 primers which each yield a noncoding amplified sequence of 100 bases. If predicted coding sequences, such as those in SEQ ID NO:7 or SEQ ID NO:19 or SEQ ID NO:61 are used, a more appropriate number of primers for positive individual identification would be 500-2,000.

If a panel of reagents from DGAT2 family member nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial DGAT2 Family Member Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of DGAT2 family member sequence (e.g., SEQ ID NO:7, SEQ ID NO:19, or SEQ ID NO:61 (e.g., fragments derived from the noncoding regions of SEQ ID NO:7 or SEQ ID NO:19 or SEQ ID NO:61 having a length of at least 20 bases, preferably at least 30 bases)) are particularly appropriate for this use.

The DGAT2 family member nucleotide sequences described herein can further be used to provide polynucleotide reagents, e.g., labeled or labelable probes which can be used in, for example, an in situ hybridization technique, to identify a specific tissue, e.g., a tissue containing one or more DGAT2 family member activities. This can be very useful in cases where a forensic pathologist is presented with a tissue of unknown origin. Panels of such DGAT2 family member probes can be used to identify tissue by species and/or by organ type.

In a similar fashion, these reagents, e.g., DGAT2 family member primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of one or more genes which encode a DGAT2 family member.

Such disorders include, e.g., a disorder associated with the misexpression of DGAT2 family member, or lipid metabolism related disorder.

The method includes one or more of the following:

detecting, in a tissue of the subject, the presence or absence of a mutation which affects the expression of one or more DGAT2 family member genes, or detecting the presence or absence of a mutation in a region which controls the expression of the gene, e.g., a mutation in the 5' control region;

detecting, in a tissue of the subject, the presence or absence of a mutation which alters the structure of one or more DGAT2 family member genes;

detecting, in a tissue of the subject, the misexpression of one or more DGAT2 family member genes, at the mRNA level, e.g., detecting a non-wild type level of a mRNA;

detecting, in a tissue of the subject, the misexpression of the gene, at the protein level, e.g., detecting a non-wild type level of a DGAT2 family member polypeptide.

In preferred embodiments the method includes: ascertaining the existence of at least one of: a deletion of one or more nucleotides from a DGAT2 family member gene; an insertion of one or more nucleotides into a DGAT2 family member gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:7, SEQ ID NO:19 or SEQ ID NO:61 or naturally occurring mutants thereof or 5' or 3' flanking sequences naturally associated with a DGAT2 family member gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of a DGAT2 family member gene; the presence of a non-wild type splicing pattern of a messenger RNA transcript of the gene; or a non-wild type level of DGAT2 family member expression.

Methods of the invention can be used prenatally or to determine if a subject's offspring will be at risk for a disorder.

In preferred embodiments the method includes determining the structure of a DGAT2 family member gene, an abnormal structure being indicative of risk for the disorder.

In preferred embodiments the method includes contacting a sample from the subject with an antibody to a DGAT2 family member protein or a nucleic acid, which hybridizes specifically with a DGAT2 family member gene. These and other embodiments are discussed below.

Diagnostic and Prognostic Assays

The presence, level, or absence of a DGAT2 family member protein or nucleic acid in a biological sample can be evaluated by obtaining a biological sample from a test subject and contacting the biological sample with a compound or an agent capable of detecting a DGAT2 family member protein or nucleic acid (e.g., mRNA, genomic DNA) that encodes a DGAT2 family member protein such that the presence of a DGAT2 family member protein or nucleic acid is detected in the biological sample. The term "biological sample" includes tissues, cells and biological fluids isolated from a subject, as well as tissues, cells and fluids present within a subject. A preferred biological sample is serum. The level of expression of the DGAT2 family member gene can be measured in a number of ways, including, but not limited to: measuring the mRNA encoded by the DGAT2 family member genes; measuring the amount of protein encoded by the DGAT2 family member genes; or measuring the activity of the protein encoded by the DGAT2 family member genes.

The level of mRNA corresponding to the DGAT2 family member gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length DGAT2 family member nucleic acid, such as the nucleic acid of SEQ ID NO:7, SEQ ID NO:19, or SEQ ID NO:61 or a portion thereof, such as an oligonucleotide of at least 7, 15, 30, 50, 100, 250 or 500 nucleotides in length and sufficient to specifically hybridize under stringent conditions to DGAT2 family member mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the DGAT2 family member genes.

The level of mRNA in a sample that is encoded by one of DGAT2 family member can be evaluated with nucleic acid amplification, e.g., by rtPCR (Mullis, 1987, U.S. Pat. No. 4,683,202), ligase chain reaction (Barany, 1991, *Proc. Natl. Acad. Sci. USA* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the DGAT2 family member gene being analyzed.

In another embodiment, the methods further contacting a control sample with a compound or agent capable of detecting DGAT2 family member mRNA, or genomic DNA, and comparing the presence of DGAT2 family member mRNA or genomic DNA in the control sample with the presence of DGAT2 family member mRNA or genomic DNA in the test sample.

A variety of methods can be used to determine the level of protein encoded by DGAT2 family member. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect DGAT2 family member protein in a biological sample in vitro as well as in vivo. In vitro techniques for detection of DGAT2 family member protein include enzyme linked immunosorbent assays (ELISAs), immunoprecipitations, immunofluorescence, enzyme immunoassay (EIA), radioimmunoassay (RIA), and Western blot analysis. In vivo techniques for detection of DGAT2 family member protein include introducing into a subject a labeled anti-DGAT2 family member antibody. For example, the antibody can be labeled with a radioactive marker whose presence and location in a subject can be detected by standard imaging techniques.

In another embodiment, the methods further include contacting the control sample with a compound or agent capable of detecting DGAT2 family member protein, and comparing the presence of DGAT2 family member protein in the control sample with the presence of DGAT2 family member protein in the test sample.

The invention also includes kits for detecting the presence of DGAT2 family member in a biological sample. For example, the kit can include a compound or agent capable of detecting DGAT2 family member protein or mRNA in a biological sample; and a standard. The compound or agent can be packaged in a suitable container. The kit-can further comprise instructions for using the kit to detect DGAT2 family member protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted DGAT2 family member expression or activity. As used herein, the term "unwanted" includes an unwanted phenomenon involved in a biological response such as pain or deregulated cell proliferation.

In one embodiment, a disease or disorder associated with aberrant or unwanted DGAT2 family member expression or activity is identified. A test sample is obtained from a subject and DGAT2 family member protein or nucleic acid (e.g., mRNA or genomic DNA) is evaluated, wherein the level, e.g., the presence or absence, of DGAT2 family member protein or nucleic acid is diagnostic for a subject having or at risk of developing a disease or disorder associated with aberrant or unwanted DGAT2 family member expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted DGAT2 family member expression or activity. For example, such methods can be used to determine whether a subject can be effectively treated with an agent for a cellular growth related disorder.

The methods of the invention can also be used to detect genetic alterations in a DGAT2 family member gene, thereby determining if a subject with the altered gene is at risk for a disorder characterized by misregulation in DGAT2 family member protein activity or nucleic acid expression, such as a cellular growth related disorder. In preferred embodiments, the methods include detecting, in a sample from the subject, the presence or absence of a genetic alteration characterized by at least one of an alteration affecting the integrity of a gene encoding a DGAT2 family member-protein, or the mis-expression of the DGAT2 family member gene. For example, such genetic -alterations can be detected by ascertaining the existence of at least one of 1) a deletion of one or more nucleotides from a DGAT2 family member gene; 2) an addition of one or more nucleotides to a DGAT2 family member gene; 3) a substitution of one or more nucleotides of a DGAT2 family member gene, 4) a chromosomal rearrangement of a DGAT2 family member gene; 5) an alteration in the level of a messenger RNA transcript of a DGAT2 family member gene, 6) aberrant modification of a DGAT2 family member gene, such as of the methylation pattern of the genomic DNA, 7) the presence of a non-wild type splicing pattern of a messenger RNA transcript of a DGAT2 family member gene, 8) a non-wild type level of a DGAT2 family member-protein, 9) allelic loss of a DGAT2 family member gene, and 10) inappropriate post-translational modification of a DGAT2 family member-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the DGAT2 family member-gene. This method can include the steps of collecting a sample of cells from a subject, isolating nucleic acid (e.g., genomic, mRNA or both) from the sample, contacting the nucleic acid sample with one or more primers which specifically hybridize to a DGAT2 family member gene under conditions such that hybridization and amplification of the DGAT2 family member-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al., (1988) *Bio-Technology* 6:1197), or other nucleic acid amplification methods, followed by the detection of the amplified molecules using techniques known to those of skill in the art.

In another embodiment, mutations in a DGAT2 family member gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498, 531) can be used to score for the presence of specific mutations by development or loss of a ribozyme cleavage site.

In other embodiments, genetic mutations in DGAT2 family member can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al., (1996) *Human Mutation* 7: 244-255; Kozal, M. J. et al., (1996) *Nature Medicine* 2:753-759). For example, genetic mutations in DGAT2 family member can be identified in two dimensional arrays containing light-generated DNA probes as described in Cronin, M. T. et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DGAT2 family member gene and detect mutations by comparing the sequence of the sample DGAT2 family member with the corresponding wild-type (control) sequence. Automated sequencing procedures can be utilized when performing the diagnostic assays ((1995) *Biotechniques* 19:448), including sequencing by mass spectrometry.

Other methods for detecting mutations in the DGAT2 family member gene include methods in which protection from cleavage agents is used to detect mismatched bases in RNA/RNA or RNA/DNA heteroduplexes (Myers et al., (1985) *Science* 230:1242; Cotton et al., (1988) *Proc. Natl. Acad. Sci. USA* 85:4397; Saleeba et al., (1992) *Methods Enzymol.* 217: 286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in DGAT2 family member cDNAs obtained from samples of cells. For example, the mutY enzyme of *E. coli* cleaves A at G/A mismatches and the thymidine DNA glycosylase from HeLa cells cleaves T at G/T mismatches (Hsu et al., (1994) *Carcinogenesis* 15:1657-1662; U.S. Pat. No. 5,459,039).

In other embodiments, alterations in electrophoretic mobility will be used to identify mutations in DGAT2 family member genes. For example, single strand conformation polymorphism (SSCP) may be used to detect differences in electrophoretic mobility between mutant and wild type nucleic acids (Orita et al., (1989) *Proc. Natl. Acad. Sci. USA:* 86:2766, see also Cotton, (1993) *Mutat. Res.* 285:125-144; and Hayashi, (1992) *Genet. Anal. Tech. Appl.* 9:73-79). Single-stranded DNA fragments of sample and control DGAT2 family member nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al., (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, (1987) *Biophys. Chem.* 265:12753).

Examples of other techniques for detecting point mutations include, but are not limited to, selective oligonucleotide hybridization, selective amplification, or selective primer extension (Saiki et al., (1986) *Nature* 324:163); Saiki et al., (1989) *Proc. Natl. Acad. Sci. USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., (1989) *Nucleic Acids Res.* 17:2437-2448) or at the extreme 3' end of one primer where, under appropriate conditions, mismatch can prevent, or reduce polymerase extension (Prossner, (1993) *Tibtech* 11:238). In addition it may be desirable to introduce a novel restriction site in the region of the mutation to create cleavage-based detection (Gasparini et al., (1992) *Mol. Cell Probes* 6:1). It is anticipated that in certain embodiments amplification may also be performed using Taq ligase for amplification (Barany, (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DGAT2 family member gene.

Use of DGAT2 Family Member Molecules as Surrogate Markers

The DGAT2 family member molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the DGAT2 family member molecules of the invention may be detected, and may be correlated with one or more biological states in vivo. For example, the DGAT2 family member molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The DGAT2 family member molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a DGAT2 family member marker) transcription or expression, the amplified marker may be in a quantity which is more readily detectable than the drug itself. Also, the marker may be more easily detected due to the nature of the marker itself; for example, using the methods described herein, anti-DGAT2 family member antibodies may be employed in an immune-based detection system for a DGAT2 family member protein marker, or DGAT2 family member-specific radiolabeled probes may be used to detect a DGAT2 family member mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The DGAT2 family member molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., DGAT2 family member protein or RNA) for specific tumor markers in a subject, a drug or course of treatment may be selected that is optimized for the treatment of the specific tumor likely to be present in the subject. Similarly, the presence or absence of a specific sequence mutation in DGAT2 family member DNA may correlate DGAT2 family member drug response. The use of pharmacogenomic markers therefore permits the application of the most appropriate treatment for each subject without having to administer the therapy.

Pharmaceutical Compositions

The nucleic acid and polypeptides, fragments thereof, as well as anti-DGAT2 family member antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted DGAT2 family member expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the DGAT2 family member molecules of the present invention or DGAT2 family member modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted DGAT2 family member expression or activity, by administering to the subject a DGAT2 family member or an agent which modulates expression of DGAT2 family member or at least one DGAT2 family member activity. Subjects at risk for a disease which is caused or contributed to by aberrant or unwanted DGAT2 family member expression or activity can be identified by, for example, any or a combination of diagnostic or prognostic assays as described herein. Administration of a prophylactic agent can occur prior to the manifestation of symptoms characteristic of the DGAT2 family member aberrance, such that a disease or disorder is prevented or, alternatively, delayed in its progression. Depending on the type of DGAT2 family member aberrance, for example, a DGAT2 family member, DGAT2 family member agonist or DGAT2 family member antagonist agent can be used for treating the subject. The appropriate agent can be determined based on screening assays described herein.

It is possible that some DGAT2 family member disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of DGAT2 family member disorders can be brought about by techniques that serve to inhibit the expression or activity of target gene products. For example, compounds, e.g., an agent identified using one or more assays described above, that proves to exhibit negative modulatory activity, can be used in accordance with the invention to prevent and/or ameliorate symptoms of DGAT2 family member related disorders (e.g., obesity, diabetes, triglyceride storage disorders). Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by DGAT2 family member expression is through the use of aptamer molecules specific for DGAT2 family member protein. Aptamers are nucleic acid molecules having a tertiary structure which permits them to specifically bind to protein ligands (see, e.g., Osborne, et al., *Curr. Opin. Chem. Biol.* 1997, 1(1): 5-9; and Patel, D. J., *Curr. Opin. Chem. Biol.* 1997 June; 1(1):32-46). Since nucleic acid molecules may in many cases be more conveniently introduced into target cells than therapeutic protein molecules may be, aptamers offer a method by which DGAT2 family member protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of DGAT2 family member disorders. For a description of antibodies, see the Antibody section above.

In circumstances wherein injection of an animal or a human subject with a DGAT2 family member protein or epitope for stimulating antibody production is harmful to the subject, it is possible to generate an immune response against DGAT2 family member through the use of anti-idiotypic antibodies (see, for example, Herlyn, D., *Ann. Med.* 1999; 31(1):66-78; and Bhattacharya-Chatteijee, M., and Foon, K. A., *Cancer Treat. Res.* 1998; 94:51-68). If an anti-idiotypic antibody is introduced into a mammal or human subject, it should stimulate the production of anti-anti-idiotypic antibodies, which should be specific to the DGAT2 family member protein. Vaccines directed to a disease characterized by DGAT2 family member expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., (1993, *Proc. Natl. Acad. Sci. USA* 90:7889-7893).

The identified compounds that inhibit target gene expression, synthesis and/or activity can be administered to a patient at therapeutically effective doses to prevent, treat or ameliorate DGAT2 family member disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate DGAT2 family member activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al., (1996) *Current*

*Opinion in Biotechnology* 7:89-94 and in Shea, K. J., (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al., (1993) *Nature* 361:645-647. Through the use of isotope-labeling, the "free" concentration of compound which modulates the expression or activity of DGAT2 family member can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al., (1995) *Analytical Chemistry* 67:2142-2144.

Another aspect of the invention pertains to methods of modulating DGAT2 family member expression or activity for therapeutic purposes. Accordingly, in an exemplary embodiment, the modulatory method of the invention involves contacting a cell with a DGAT2 family member or agent that modulates one or more of the activities of DGAT2 family member protein activity associated with the cell. An agent that modulates DGAT2 family member protein activity can be an agent as described herein, such as a nucleic acid or a protein, a naturally-occurring target molecule of a DGAT2 family member protein (e.g., a DGAT2 family member substrate or receptor), a DGAT2 family member antibody, a DGAT2 family member agonist or antagonist, a peptidomimetic of a DGAT2 family member agonist or antagonist, or other small molecule.

In one embodiment, the agent stimulates one or more DGAT2 family member activities. Examples of such stimulatory agents include active DGAT2 family member protein and a nucleic acid molecule encoding DGAT2 family member. In another embodiment, the agent inhibits one or more DGAT2 family member activities. Examples of such inhibitory agents include antisense DGAT2 family member nucleic acid molecules, anti-DGAT2 family member antibodies, and DGAT2 family member inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a DGAT2 family member protein or nucleic acid molecule. In one embodiment, the method involves administering an agent (e.g., an agent identified by a screening assay described herein), or combination of agents that modulates (e.g., upregulates or downregulates) DGAT2 family member expression or activity. In another embodiment, the method involves administering a DGAT2 family member protein or nucleic acid molecule as therapy to compensate for reduced, aberrant, or unwanted DGAT2 family member expression or activity.

Stimulation of DGAT2 family member activity is desirable in situations in which DGAT2 family member is abnormally downregulated and/or in which increased DGAT2 family member activity is likely to have a beneficial effect. For example, stimulation of DGAT2 family member activity is desirable in situations in which a DGAT2 family member is downregulated and/or in which increased DGAT2 family member activity is likely to have a beneficial effect. Likewise, inhibition of DGAT2 family member activity is desirable in situations in which DGAT2 family member is abnormally upregulated and/or in which decreased DGAT2 family member activity is likely to have a beneficial effect.

The DGAT2 family member molecules can act as novel diagnostic targets and therapeutic agents for controlling one or more of metabolic disorders, liver disorders, cellular proliferative and/or differentiative disorders, cardiovascular disorders, as described above.

Diseases of metabolic imbalance include, but are not limited to, obesity, lipid disorders including hyperlipidemia, and diabetes.

Pharmacogenomics

The DGAT2 family member molecules of the present invention, as well as agents, or modulators which have a stimulatory or inhibitory effect on DGAT2 family member activity (e.g., DGAT2 family member gene expression) as identified by a screening assay described herein can be administered to individuals to treat (prophylactically or therapeutically) DGAT2 family member associated disorders (e.g., cellular growth related disorders) associated with aberrant or unwanted DGAT2 family member activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DGAT2 family member molecule or DGAT2 family member modulator as well as tailoring the dosage and/or therapeutic regimen of treatment with a DGAT2 family member molecule or DGAT2 family member modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a DGAT2 family member protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a DGAT2 family member molecule or DGAT2 family member modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a DGAT2 family member molecule or DGAT2 family member modulator, such as a modulator identified by one of the exemplary screening assays described herein.

The present invention further provides methods for identifying new agents, or combinations, that are based on identifying agents that modulate the activity of one or more of the gene products encoded by one or more of the DGAT2 family member genes of the present invention, wherein these products may be associated with resistance of the cells to a therapeutic agent. Specifically, the activity of the proteins encoded by the DGAT2 family member genes of the present invention can be used as a basis for identifying agents for overcoming agent resistance. By blocking the activity of one or more of the resistance proteins, target cells, e.g., adipocytes, will become sensitive to treatment with an agent that the unmodified target cells were resistant to.

Monitoring the influence of agents (e.g., drugs) on the expression or activity of a DGAT2 family member protein can be applied in clinical trials. For example, the effectiveness of an agent determined by a screening assay as described herein to increase DGAT2 family member gene expression, protein levels, or upregulate DGAT2 family member activity, can be monitored in clinical trials of subjects exhibiting decreased DGAT2 family member gene expression, protein levels, or downregulated DGAT2 family member activity. Alternatively, the effectiveness of an agent determined by a screening assay to decrease DGAT2 family member gene expression, protein levels, or downregulate DGAT2 family member activity, can be monitored in clinical trials of subjects exhibiting increased DGAT2 family member gene expression, protein levels, or upregulated DGAT2 family member activity. In such clinical trials, the expression or activity of a DGAT2 family member gene, and preferably, other genes that have been implicated in, for example, a DGAT2 family member-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a DGAT2 family member, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to one or more DGAT2 family member nucleic acids, polypeptides, or antibodies.

The capture probes can be a set of nucleic acids from a selected sample, e.g., a sample of nucleic acids derived from a control or non-stimulated tissue or cell.

The method can include contacting the DGAT2 family member nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a DGAT2 family member molecule. Such methods can be used to diagnose a subject, e.g., to evaluate risk for a disease or disorder, to evaluate suitability of a selected treatment for a subject, to evaluate whether a subject has a disease or disorder. DGAT2 family member is associated with triglyceride biosynthesis or activity, thus it is useful for disorders associated with abnormal lipid metabolism.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express one or more DGAT2 family member molecules of the invention or from a cell or subject in which a DGAT2 family member mediated response has been elicited, e.g., by contact of the cell with one or more DGAT2 family member nucleic acids or proteins, or administration to the cell or subject DGAT2 family member nucleic acids or proteins; contacting the array with one or more inquiry probe, wherein an inquiry probe can be a nucleic acid, polypeptide, or antibody (which is preferably other than DGAT2 family member nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express DGAT2 family member (or does not express as highly as in the case of the DGAT2 family member positive plurality of capture probes) or from a cell or subject which in which a DGAT2 family member mediated response has not been elicited (or has been elicited to a lesser extent than in the first sample); contacting the array with one or more inquiry probes (which is preferably other than a DGAT2 family member nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing a DGAT2 family member, e.g., analyzing structure, function, or relatedness to other nucleic acid or amino acid sequences. The method includes: providing a DGAT2 family member nucleic acid or amino acid sequence; comparing the DGAT2 family member sequence with one or more preferably a plurality of sequences from a collection of sequences, e.g., a nucleic acid or protein sequence database; to thereby analyze DGAT2 family member.

Preferred databases include GenBank™. The method can include evaluating the sequence identity between a DGAT2 family member sequence and a database sequence. The method can be performed by accessing the database at a second site, e.g., over the internet.

In another aspect, the invention features, a set of oligonucleotides, useful, e.g., for identifying SNP's, or identifying specific alleles of DGAT2 family members. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples, which should not be construed as limiting. The contents of all references, patents and published patent applications cited throughout this application are incorporated herein by reference.

EXAMPLES

Example 1

Identification and Characterization of Human DGAT2 Family Member cDNAs and Proteins A number of gene sequences were identified which have homology to the DGAT2 sequences. The human DGAT2, (herein referred to as 86606) sequence is depicted in SEQ ID NO:9, which is approximately 2428 nucleotides long including untranslated regions, contains a predicted methionine-initiated coding sequence of about 1166 nucleotides (nucleotides 220-1386 of SEQ ID NO:9). The coding sequence encodes a 388 amino acid protein (SEQ ID NO:10).

The human DGAT2 family member sequence 60489 (SEQ ID NO:7), which is approximately 1255 nucleotides long including untranslated regions, contains a predicted methionine-initiated coding sequence of about 1025 nucleotides (nucleotides 170-1195 of SEQ ID NO:7) The coding sequence encodes a 341 amino acid protein (SEQ ID NO:8).

The DGAT2 family member sequence 112041 (SEQ ID NO:19), which is approximately 1716 nucleotides long including untranslated regions, contains a predicted methionine-initiated coding sequence of about 1013 nucleotides (nucleotides 101-1114 of SEQ ID NO:19) The coding sequence encodes a 337 amino acid protein (SEQ ID NO:20).

The DGAT2 family member sequence 112037 (SEQ ID NO:61), which is approximately 712 nucleotides long, is a predicted partial coding sequence. The sequence encodes a 236 amino acid protein (SEQ ID NO:62).

The DGAT2 family member sequence of 58765 identified two splice variant sequences including 58765 (SEQ ID NO:1), which is approximately 1005 nucleotides long, encodes a 334 amino acid protein (SEQ ID NO:2). Additionally, 58765short (SEQ ID NO:3), which is approximately 855 nucleotides long, encodes a 284 amino acid protein (SEQ ID NO:4).

The DGAT2 family member sequence 112023 (SEQ ID NO:13), which is approximately 1279 nucleotides long including untranslated regions, contains a predicted methionine-initiated coding sequence of about 986 nucleotides (nucleotides 42-1028 of SEQ ID NO:13) The coding sequence encodes a 328 amino acid protein (SEQ ID NO:14).

The DGAT2 family member sequence 112024 (SEQ ID NO:17), which is approximately 1720 nucleotides long including untranslated regions, contains a predicted methionine-initiated coding sequence of about 1001 nucleotides (nucleotides 1-1002 of SEQ ID NO:17) The coding sequence encodes a 333 amino acid protein (SEQ ID NO:18).

The DGAT2 family member sequence hDC2 (SEQ ID NO:21), which is approximately 1093 nucleotides long including untranslated regions, contains a predicted methionine-initiated coding sequence of about 1004 nucleotides (nucleotides 49-1053 of SEQ ID NO:21) The coding sequence encodes a 334 amino acid protein (SEQ ID NO:22).

Example 2

Identification and Characterization of Murine DGAT2 Family Member cDNAs and Proteins A number of murine gene sequences were also identified which are related to DGAT2 sequences. The murine DGAT2 sequence (m86606) is depicted in SEQ ID NO:11, which is approximately 2262 nucleotides long including untranslated regions, contains a predicted methionine-initiated coding sequence of about 1166 nucleotides (nucleotides 207-1373 of SEQ ID NO:11). The coding sequence encodes a 388 amino acid protein (SEQ ID NO:12).

The murine DGAT2 family member sequence m58765 sequence (SEQ ID NO:5), which is approximately 1748 nucleotides long including untranslated regions, contains a predicted methionine-initiated coding sequence of about 758 nucleotides (nucleotides 254-1012 of SEQ ID NO:5). The coding sequence encodes a 252 amino acid protein (SEQ ID NO:6).

The DGAT2 family member sequence m112023 (SEQ ID NO:15), which is approximately 1255 nucleotides long including untranslated regions, contains a predicted methionine-initiated coding sequence of about 1124 nucleotides (nucleotides 27-1151 of SEQ ID NO:15) The coding sequence encodes a 374 amino acid protein (SEQ ID NO:16).

The DGAT2 family member cDNA sequence mDC2 (SEQ ID NO:23), which is approximately 1008 nucleotides encodes a 335 amino acid protein (SEQ ID NO:24).

Example 3

DGAT2 Family Member Gene Expression in Human and Mouse Tissues RNA Samples

Human tissue samples were either purchased from Invitrogen or were prepared from samples available at Millennium. Total RNA samples from various mouse tissues were extracted from 8 week old female mice. All mice were purchased from Jackson Labs. To investigate tissue distribution of these genes, cDNAs were prepared from RNA samples prior to Taqman analysis.

RNA was prepared using the trizol method and treated with DNAse to remove contaminating genomic DNA. cDNA was synthesized using random hexamer primers. Mock cDNA synthesis in the absence of reverse transcriptase resulted in samples with no detectable PCR amplification of the control 18S gene confirming efficient removal of genomic DNA contamination. Taqman analysis was performed following the manufacturer's directions.

PCR probes were designed by PrimerExpress software (PE Biosystems) based on the respective sequences of murine and human genes. The following probes and primers were used:

```
86606 forward primer:
                                         (SEQ ID NO:25)
CAAGCCCCTTTATTGCCACTAC 86606 reverse primer:
                                         (SEQ ID NO:26)
TCCCCTTGGCAGAGAAACTG 86606 Probe:
                                         (SEQ ID NO:27)
CCACGCTCGTCTAGTCCTGAAACTGCAG m86606 forward primer:
                                         (SEQ ID NO:28)
TTCCCCAGACGACAGACACTT m86606 reverse primer:
                                         (SEQ ID NO:29)
CTCTCAAGAATCCCTGGAGTCACT m86606 Probe:
                                         (SEQ ID NO:30)
ACTGCCCTTGCCCAGCTAGCCAGTACTGCCCTTGCCCAGCTAGCCAG hDC2 forward primer:
                                         (SEQ ID NO:31)
CTATAGGAAAGCCATCCACACTGTT hDC2 reverse primer:
                                         (SEQ ID NO:32)
GGGTCGGGTTCAGAGTCTGA hDC2 Probe:
                                         (SEQ ID NO:33)
TTGGCCGCCCGATCCCTGT mDC2 forward primer:
                                         (SEQ ID NO:34)
GGCTCACCCAGGAACATTCA mDC2 reverse primer:
                                         (SEQ ID NO:35)
GGTCAAGGCCATCTTAACAAACC mDC2 Probe:
                                         (SEQ ID NO:36)
CTGTGCATCCGCCAGCGCAA 112023 forward primer:
                                         (SEQ ID NO:37)
GCGGCCACAAGGATGTAAA 112023 reverse primer:
                                         (SEQ ID NO:38)
GAGCTACCTTGCCATCTTTTGG 112023 Probe:
                                         (SEQ ID NO:39)
AGCAGGTAGACGAACAATGGCTGCAAGATCTTGCAGCCATTGTTCGTCTA
CCTGCT m112023 forward primer:
                                         (SEQ ID NO:40)
CGTTGCCATGTTTTGGATTG m112023 reverse primer:
                                         (SEQ ID NO:41)
TGTTGGTAGCGGCCACAA m112023 Probe:
                                         (SEQ ID NO:42)
CAGCCATTGTTAATTTGCCTATTGTTTCACACC 112024 forward primer:
                                         (SEQ ID NO:43)
TCAATGCTGGCACCAAAGTG 112024 reverse primer:
                                         (SEQ ID NO:44)
TGGTGAGATAGTCCCAAGAAACAG 112024 Probe:
                                         (SEQ ID NO:45)
AGGCCCGTCTCCCCTAGGCTCTTC m58765 forward primer:
                                         (SEQ ID NO:46)
GGTGAGTGCCGATCACATTCT m58765 reverse primer:
                                         (SEQ ID NO:47)
CAACGATGATGGCAAGCAAGT m58765 Probe:
                                         (SEQ ID NO:48)
TCCAGGAAGGGCGGCGGGCCCGCCGCCCTTCCTGGA 58765 forward primer:
                                         (SEQ ID NO:49)
TGACCGCGCCATTTCCTA 58765 reverse primer:
                                         (SEQ ID NO:50)
GATTCAGACTGGTCCAAACCCTAT 58765 Probe:
                                         (SEQ ID NO:51)
TCCTTCCATGACCCTCCATTGCTCCTAG 58765s forward primer:
                                         (SEQ ID NO:52)
CCTGGATCCTTCACGCTGTTAC 58765s reverse primer:
                                         (SEQ ID NO:53)
AGGCTTGATACCCGTGTGTCA 58765s Probe:
                                         (SEQ ID NO:54)
CGGAACCGAAAGGGCTTCGTCAGCTGACGAAGCCCTTTCGGTTCCG
```

```
60489 forward primer:
                                               (SEQ ID NO:55)
CGAGGAGGAAGTCAATCACTATCA 60489 reverse primer:
                                               (SEQ ID NO:56)
TTTCCTTGTGCTCCTCGAAGA 60489 Probe:
                                               (SEQ ID NO:57)
CCCTCTACATGACGGACCTGGAGCAG 112041 forward primer:
                                               (SEQ ID NO:58)
GAGACCCAAGAGCTGACAATTACA 112041 reverse primer:
                                               (SEQ ID NO:59)
TGGATCCCTCATGGCTTTG 112041 Probe:
                                               (SEQ ID NO:60)
AACAGGAGCCACATTCCCCATTGATCA 112037 forward primer:
                                               (SEQ ID NO:63)
CCTGCCTCTTCCCCAAACTC 112037 reverse primer:
                                               (SEQ ID NO:64)
GAAGAAGAGGAGATGGAACCAACA 112037 probe:
                                               (SEQ ID NO:65)
CGCCACACCTGCTCATGCTGC
```

To allow standardization between different tissues, each sample contained two probes distinguished by different fluorescent labels, a probe for the gene of interest (e.g. 86606) as well as a probe for 18S RNA as an internal control. The threshold values at which the PCR amplification started were determined using the manufacturer's software.

The following method was used to quantitatively calculate gene expression in the tissue samples, relative to the 18S RNA expression in the same tissue. The threshold values at which the PCR amplification started were determined using the manufacturer's software. PCR cycle number at threshold value was designated as CT. Relative expression was calculated as $2^{-((CTtest-CT18S)\ tissue\ of\ interest - (CTtest-CT18S)\ lowest\ expressing\ tissue\ in\ panel)}$. Samples were run in duplicate and the averages of 2 relative expression levels that were linear to the amount of template cDNA with a slope similar to the slope for the internal control 18S were used. The resulting relative expression levels for each gene of interest were compiled and calculated in separate experiments.

The results of expression of 86606 in human tissues by Taqman analysis showed highest levels of expression in adipose and medium level in liver and lower levels in brain, heart, kidney and small intestine, among the nine human tissues that we have investigated. hDC2 is expressed at highest levels in liver and kidney, and at a lower level in adipose, brain and heart in human tissues tested. The expression of 112024 is very low in all the human tissues that we examined. 58765 has two splicing variants, the short form (58765short) lacks part of the C-terminus compared with the long form (58765). Both forms of 58765 are highly expressed in small intestine, as well as the liver, and at lower levels in kidney and adipose tissue. 60489 is expressed highly in small intestine as well as the kidney, and at lower levels in liver and adipose tissues. 112041 is expressed at higher levels in small intestine and adipose tissues compared with other tissues that we have investigated in human. 112037 is expressed in the small intestine, and at lower levels in adipose and kidney.

In addition to the initial nine human tissues tested, we examined expression of 58765short and 60489 in an additional panel of human tissues (Table 3). 58765short and 60489 demonstrated highest expression in small intestine (as seen in Table 2 above), as well as significant expression in colon, with lower expression in liver which is upregulated in liver fibrosis (Table 3). Tissues also tested which did not demonstrate significant expression levels include erythroid, megakaryocytes, neutrophils, activated PBMCs, hematopoietic progenitor cells (erythroid, megakaryocyte, neutrophil), synovium, macrophages, lymph node, spleen, lung (normal, COPD, and tumor), prostate (normal and tumor), breast (normal and tumor), ovary tumor, dorsal root ganglion, pancreas, nerve, hypothalamus, pituitary gland, brain cortex, spinal cord, skin, adrenal cortex, bladder, primary osteoblast, adipose, skeletal muscle, heart (normal and CHF), hemangioma, HUVEC, coronary SMC, and vessel (artery, vein, and diseased aorta) tissue.

TaqMan analysis was also performed in mouse tissues as indicated above. The mouse orthologue of 86606, m86606 is expressed highly in both white and brown adipose tissues in mouse, with lower levels of expression in liver, heart, small intestine and kidney; mDC2 is expressed at highest levels in both brown and white adipose tissues as well as kidney in mouse; m112023 is low in all tissues that we examined. Among these tissues, the relative expression level is lung>spleen>w fat, b fat>other tissues; and m58765, similar to human 58765, is highly expressed in small intestine, with lower levels of expression in kidney and adipose tissue in mouse (Table 4).

TABLE 2

| DGAT2 family member expression in human tissues | | | | | | | |
|---|---|---|---|---|---|---|---|
| tissue | 86606 | hDC2 | 112024 | 58765 | 58765 s | 60489 | 112041 | 112037 |
| adipose | 1005 | 2642 | 2.124 | 347.0 | 183.7 | 136.5 | 404.8 | 6.801 |
| brain | 24.86 | 1146 | 1.218 | 8.503 | 28.45 | 6.013 | 235.7 | 3.866 |
| heart | 19.90 | 1389 | 1.266 | 23.37 | 8.462 | 3.451 | 103.4 | 1.431 |
| kidney | 13.38 | 8975 | 0.918 | 3399 | 1660 | 9950 | 214.6 | 5.684 |
| liver | 349.8 | 13827 | 1.307 | 30902 | 19076 | 2445 | 56.00 | 3.599 |
| pancreas | 1.014 | 125.4 | 1.219 | 9.563 | 2.629 | 1.091 | 31.04 | 2.464 |
| spleen | 9.242 | 1.086 | 1.390 | 39.34 | 18.71 | 6.291 | 141.1 | 4.114 |
| s. intestine | 22.99 | 48.77 | 2.045 | 1773348 | 60400 | 65083 | 685.2 | 56.54 |
| sk. muscle | 1.894 | 104.06 | 1.124 | 8.800 | 7.425 | 2.836 | 5.257 | 1.838 |

TABLE 3

DGAT2 family member expression in human tissues

| Tissue Type | 58765short | 60489 |
|---|---|---|
| Kidney | 0.086 | 0.2681 |
| Small intestine normal | 4.1721 | 7.2641 |
| Ovary normal | 0.3739 | 1.6198 |
| Colon normal | 2.4466 | 6.1936 |
| Colon Tumor | 1.6827 | 6.8248 |
| Colon IBD | 0.2375 | 3.14 |
| Liver normal | 0.674 | 0.9868 |
| Liver fibrosis | 1.5919 | 4.3493 |
| Tonsil normal | 0.0309 | 0 |

TABLE 4

DGAT2 family member expression in mouse tissues

| tissue | m86606 | mDC2 | m112023 | m58765 |
|---|---|---|---|---|
| brain | 16.9188 | 4.9502 | 1.1598 | 5.0109 |
| hypothalamus | 9.71379 | 18.1208 | 1.4636 | — |
| heart | 78.0162 | 0.5721 | 1.4056 | 233.2449 |
| kidney | 32.197 | 304.62 | 1.1728 | 588.3001 |
| liver | 89.0194 | 3.8243 | 1.2581 | 4.18738 |
| lung | 11.1751 | 9.003 | 111.3496 | 7.8561 |
| spleen | 1.07834 | 4.2266 | 26.6539 | 3.0421 |
| s. intestine | 60.3415 | 1.3351 | 5.7179 | 10903.28 |
| muscle | 9.37499 | 2.8787 | 1.1487 | 33.5309 |
| adipose | — | — | — | 0.9569 |
| w fat | 943.759 | 207.577 | 6.0579 | 242.4002 |
| b fat | 537.813 | 189.39 | 1.3619 | 137.4226 |

In addition to the initial nine murine tissues tested, we examined expression of m58765 in an additional panel of mouse tissues (Table 5). m58765 demonstrated highest expression in intestine and kidney (as seen in Table 4 above), (Table 5). Tissues also tested which did not demonstrate significant expression levels (0.0001 or below) include Salivary Gland/Normal/MPI1197, Hypothalamus/Normal/MET237, Spinal Cord/Normal/MET238, Lung/Normal/MET148, Esophagus/Normal/MET143, Liver/Normal/MPI149, Brain/Normal/MPI1195, Skin/Normal/MET067, Spleen/Normal/MET063, Pancreas/Normal/MET192, Primary Osteoblast/Normal/MET198, ST2-0/Normal/MET199, ST2-4/Normal/MET200, Muscle/Normal/MPI1266, and Prostate/Normal/MPI1203

TABLE 5

DGAT2 family member expression in mouse tissues

| Tissue Type | m58765 | Tissue Type | m58765 |
|---|---|---|---|
| Intestine/Normal/MET145 | 0.0749 | E13/Normal/MPI1229 | 0.0019 |
| E10/Normal/MPI1232 | 0.0164 | E15.5/Normal/MPI1056 | 0.0019 |
| Kidney/Normal/MET146 | 0.0126 | E16.5/Normal/MPI1017 | 0.0019 |
| Placenta/Normal/MPI1228 | 0.0062 | E13.5/Normal/MPI1039 | 0.0017 |
| Heart/Normal/MET142 | 0.0036 | Colon/Normal/MET191 | 0.0010 |
| Testes/Normal/MET069 | 0.0053 | Ovary/Normal/MPI1202 | 0.0009 |
| E17.5/Normal/MPI1020 | 0.0049 | Calveolar/Normal/MET201 | 0.0009 |
| E18.5/Normal/MPI1024 | 0.0042 | Uterus/Normal/MET236 | 0.0008 |
| E19.5/Normal/MPI1067 | 0.0037 | Stomach/Normal/MET160 | 0.0007 |
| P1.5/Normal/MPI1062 | 0.0032 | Bladder/Normal/MET139 | 0.0003 |
| E8.5 with yolk sac/Normal/MPI1249 | 0.0058 | Adrenal Gland/Normal/MPI1192 | 0.0003 |
| Diaphysis/Normal/MET202 | 0.0028 | Breast/Normal/MPI1226 | 0.0002 |
| Metaphysis/Normal/MET203 | 0.0021 | Aorta/Normal/MET064 | 0.0002 |
| Brown Fat/Normal/MET138 | 0.0017 | White Fat/Normal/MET162 | 0.0002 |

Examples 4-7

Regulation of DGAT2 Family Member Expression

To determine whether DGAT2 family member expression is regulated under conditions that affect adipocyte differentiation or white adipocyte metabolism, expression of DGAT2 family member was measured in cells or tissues of mice exposed to various conditions. For analyses, TaqMan analysis was performed as indicated above.

Example 4

Regulation of DGAT2 Family Members during Adipocyte Differentiation

DGAT2 Family Member Expression During 3T3-F442A Differentiation

We tested expression of m86606 during differentiation of the preadipocyte cell line 3T3-F442A. 3T3-F442A preadipocytes were grown in DMEM containing 10% Calf Serum. Once they reached confluency (designed as day 0), they were induced to differentiate by culturing in DMEM containing 10 µ/ml insulin, 0.5 mM isobutyl-methylxanthine, 1 µM Dexamethasone and 10% FBS in DMEM. Forty-eight hours post-induction, cells were maintained in 10% FBS in DMEM with 2.5 µg/ml insulin. Medium was replaced every two days. Cells were harvested at day 0 and day 10 post-induction of differentiation. Total RNA was extracted and cDNAs were made from these samples and subjected to Taqman analysis.

m86606 was expressed at very low levels in preadipocytes and was dramatically upregulated during adipocyte differentiation, consistent with expression of 86606 in adipocytes rather than other cell types in the adipose tissue (Table 6).

TABLE 6

DGAT2 family member expression during 3T3-F442A differentiation

| DAY | m86606 |
|---|---|
| 0 | 1.0434 |
| 13 | 139.5925 |

DGAT2 Family Member Expression in Human Preadipocytes and Primary Adipocytes

Expression of 86606 and hDC2 were assessed in human preadipocytes and differentiated human adipocytes. Total RNAs of human primary adipocytes (HPA) and human subcutaneous preadipocytes (HSPA) were purchased from Zen-Bio, Inc. cDNAs were made from these samples and subjected to Taqman analysis. 86606 was expressed at very low levels in preadipocytes and dramatically upregulated during the differentiation of human primary adipocytes. hDC2 was expressed at similar levels in both pre- and primary adipocytes and did not demonstrate upregulation upon differentiation (Table 7).

TABLE 7

DGAT2 family member expression in human preadipocytes and adipocytes

| tissue | 86606 | hDC2 |
|---|---|---|
| HPA | 1792.1694 | 142.5415 |
| HSPA | 3.9581 | 234.6578 |

Example 5

Regulation of DGAT2 Family Member in Diet Induced Obese Mice

To examine the regulation of these genes in a diet induced obesity mouse model, 6 week old C57 BL/6 male mice were fed with either a high-fat diet or a chow-diet for 24 weeks. White adipose tissues were collected from these mice for Taqman analysis. m86606 and mDC2 mRNA are down regulated in WAT from mice fed with a high fat (HF)-diet compared with mice fed with a chow-diet (Table 8).

TABLE 8

DGAT2 family member expression in WAT from mice fed varied diets

| Diet | m86606 | mDC2 |
|---|---|---|
| High Fat | 1.0664 | 1.0396 |
| Chow | 1.627 | 2.3457 |

Example 6

Regulation of DGAT2 Family Members in Genetically Obese Mice

To investigate the regulation of these genes in genetic obese mouse model, white adipose tissue were collected from male, 8 week old ob/ob mice and their lean littermates for Taqman analysis. White adipose tissues were collected from these mice for Taqman analysis. mDC2 expression was considerably lower in ob/ob mice compared to wild-type control mice (Table 9). m86606 expression did not change considerably in ob/ob mice when compared to wild-type control mice.

TABLE 9

DGAT2 family member expression in WAT from ob/ob and WT mice

| genotype | mDC2 | m86606 |
|---|---|---|
| WT | 9132.42 | 319.58 |
| ob/ob | 407.32 | 280.46 |

Example 7

Regulation of DGAT2 Family Member During Fasting and Refeeding

Stimulation of lipolysis is believed to be an effective strategy for decreasing body weight. To examine a possible role of DGAT2 family member in lipolysis we examined its expression in white adipose tissues of mice which had been fasted for 3 days. Under those conditions, lipolysis is maximally stimulated and mice rely on fatty acids released from adipose tissue as an energy source. Fasting mice for 3 days decreased m86606 and mDC2 expression in white adipose tissue. Refeeding for 1 and 2 days caused an increase compared to fasted animals (Table 10).

TABLE 10

DGAT2 family member expression in WAT during fasting and refeeding

| treatment | m86606 | mDC2 |
|---|---|---|
| control | 6.065 | 3.9457 |
| 3d starvation | 1.0625 | 1.0396 |
| 1d refeeding | 16.1175 | 3.5233 |
| 2d refeeding | 18.1614 | 4.0593 |

Example 8

Recombinant Expression of DGAT2 Family Members in Bacterial Cells

For expression of recombinant DGAT2 family member, a glutathione-S-transferase (GST) fusion polypeptide of a DGAT2 family member protein is expressed in E. coli, isolated and characterized. Specifically, a DGAT2 family member polypeptide is genetically fused to GST and this fusion polypeptide is expressed in E. coli, e.g., strain PEB199. Expression of the GST-DGAT2 family member fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 9

Expression of Recombinant DGAT2 Family Members Protein in Mammalian Cells

To express a DGAT2 family member gene in mammalian cells, for example COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire DGAT2 family member protein of interest and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the DGAT2 family member DNA sequence is amplified by PCR using two primers. The 5' primer contains the restriction site of interest followed by approximately twenty nucleotides of the DGAT2 family member coding sequence starting from the initiation codon; the 3' end sequence contains complementary sequences to the other restriction site of interest, a translation stop codon, the HA tag or FLAG tag and the last 20 nucleotides of the DGAT2 family member coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the DGAT2 family member gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the DGAT2 family member-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the DGAT2 family member polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the DGAT2 family member coding sequence is cloned directly into the polylinker of the pcDNA/Amp vector using the appropriate restriction sites. The resulting plasmid is transfected into COS cells in the manner described above, and the expression of the DGAT2 family member polypeptide is detected by radiolabelling and immunoprecipitation using a DGAT2 family member specific monoclonal antibody.

Example 10

Regulation of DGAT2 Family Members During Enterocyte Differentiation

Caco-2 is a human intestinal cell line. Upon reach confluence, the cells express characteristics of enterocytic differentiation. During Caco-2 differentiation, triglyceride synthesis is increased (Pamela J et al Journal of Lipid Research, 1991, 32:293-304). To determine whether the expression of 58765 and 60489 are also elevated, we examined the expression of 58765 and 60489 in Caco-2 cells during differentiation.

Caco-2 cells were purchased from ATCC. They were cultured in DMEM containing 15% fetal bovine serum. The medium was changed 2-3 times per week. At day 3, the cells were at subconfluence. They reached confluence and started differentiating at day 7. At day 25, they were fully differentiated. The cells were harvested for RNA extraction at day 3 and day 25 after they were seeded. Taqman analysis was performed as described above to determine relative expression levels of 58765 and 60489 (Table 11).

Taqman data demonstrate that both 58765 and 60489 are upregulated during differentiation which correlates well with triglyceride synthesis in these cells (Table 11). This is consistent with playing a role in triglyceride biosynthesis in the small intestine.

TABLE 10

| DGAT2 family member expression during enterocyte differentiation | | |
|---|---|---|
| day | 58765 | 60489 |
| 3-1 | 1.86 | 1.22 |
| 3-2 | 1.13 | 1.11 |
| 25-1 | 98.36 | 2.79 |
| 25-2 | 91.13 | 4.02 |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid selected from the group consisting of:
   a) a nucleic acid comprising the nucleotide sequence of SEQ ID NO:7; and
   b) a nucleic acid encoding a polypeptide comprising the amino acid sequence of SEQ ID NO:8.

2. The nucleic acid of claim 1, wherein the nucleic acid comprises the nucleotide sequence of SEQ ID NO:7.

3. The nucleic acid of claim 1, wherein the nucleic acid encodes a polypeptide comprising the amino acid sequence of SEQ ID NO:8.

4. The nucleic acid of claim 1, wherein the nucleic acid consists of the nucleotide sequence of SEQ ID NO:7.

5. The nucleic acid of claim 1, wherein the nucleic acid consists of a nucleotide sequence encoding the amino acid sequence of SEQ ID NO:8.

6. A vector comprising the nucleic acid of claim 1.

7. A vector comprising the nucleic acid of claim 2.

8. A vector comprising the nucleic acid of claim 3.

9. A vector comprising the nucleic acid of claim 4.

10. A vector comprising the nucleic acid of claim 5.

11. An isolated host cell comprising the nucleic acid of claim 1.

12. An isolated host cell comprising the nucleic acid of claim 2.

13. An isolated host cell comprising the nucleic acid of claim 3.

14. An isolated host cell comprising the nucleic acid of claim 4.

15. An isolated host cell comprising the nucleic acid of claim 5.

* * * * *